(12) United States Patent
Kooij et al.

(10) Patent No.: US 11,633,561 B2
(45) Date of Patent: Apr. 25, 2023

(54) ADJUSTABLE HEADGEAR THAT IS EASY TO DON AND DOFF

(71) Applicant: RESMED PTY LTD, Bella Vista (AU)

(72) Inventors: Michiel Kooij, Sydney (AU); Iain McNicol Finlay, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 0 days.

(21) Appl. No.: 17/623,551

(22) PCT Filed: Jun. 24, 2020

(86) PCT No.: PCT/IB2020/055966
§ 371 (c)(1),
(2) Date: Dec. 28, 2021

(87) PCT Pub. No.: WO2020/261138
PCT Pub. Date: Dec. 30, 2020

(65) Prior Publication Data
US 2022/0249792 A1     Aug. 11, 2022

(30) Foreign Application Priority Data

Jun. 28, 2019    (AU) ................................ 2019902270

(51) Int. Cl.
    *A61M 16/06*        (2006.01)
    *A61M 16/08*        (2006.01)
    *A61M 16/20*        (2006.01)

(52) U.S. Cl.
CPC .... *A61M 16/0605* (2014.02); *A61M 16/0683* (2013.01); *A61M 16/0825* (2014.02);
(Continued)

(58) Field of Classification Search
CPC ......... A61B 5/087; A61B 5/4809; A61F 5/56; A61M 16/0057; A61M 16/0066;
(Continued)

(56) References Cited

U.S. PATENT DOCUMENTS 4,782,832 A    11/1988   Trimble et al.
4,944,310 A     7/1990   Sullivan
(Continued)

FOREIGN PATENT DOCUMENTS

WO    WO 98/004310 A1    2/1998
WO    WO 98/034665 A1    8/1998
(Continued)

OTHER PUBLICATIONS

International Preliminary Report on Patentability dated Dec. 28, 2021 issued in PCT/IB2020/055966 (7 pages).
(Continued)

*Primary Examiner* — Annette Dixon
(74) *Attorney, Agent, or Firm* — Nixon & Vanderhye P.C.

(57) ABSTRACT

A patient interface includes a plenum chamber, a seal-forming structure, and a positioning and stabilising structure to provide a force to hold the seal-forming structure in a therapeutically effective position on a patient's head. The positioning and stabilizing structure includes a superior strap portion, an inferior strap portion, and a posterior connecting strap portion connected to or formed integrally with the superior strap portion and the inferior strap portion. The posterior connecting strap portion is constructed from a mesh material that is different than the material used to construct the superior strap portion and the inferior strap portion. The posterior connecting strap portion has a greater stretch capability than the superior strap portion and a lesser stretch capability than the inferior strap portion. The stretch capabilities allow the positioning and stabilizing structure to be removable from the patient's head when the loop engages the connection portion.

30 Claims, 36 Drawing Sheets

(52) U.S. Cl.
CPC ...... *A61M 16/0875* (2013.01); *A61M 16/208* (2013.01); *A61M 2202/0225* (2013.01); *A61M 2205/0216* (2013.01); *A61M 2205/583* (2013.01)

(58) Field of Classification Search
CPC ............ A61M 16/0069; A61M 16/024; A61M 16/06; A61M 16/0605; A61M 16/0633; A61M 16/0683; A61M 16/0694; A61M 16/10; A61M 2016/0027; A61M 2016/0039; A61M 2016/0661; A61M 2021/0016; A61M 2021/0027; A61M 2021/0044; A61M 21/02; A61M 2205/3375; A61M 2205/3561; A61M 2205/3584; A61M 2205/3592; A61M 2205/502; A61M 2205/583; A61M 2205/8206; A61M 2207/00; A61M 2209/086; A61M 2210/06; A61M 2210/0618; A61N 2005/0648; A61N 5/06; A61N 5/0618; A62B 18/084; G01L 5/06; Y10T 29/49826
See application file for complete search history.

(56) References Cited

U.S. PATENT DOCUMENTS

| | | | |
|---|---|---|---|
| 6,123,082 | A | 9/2000 | Berthon-Jones |
| 6,532,959 | B1 | 3/2003 | Berthon-Jones |
| 6,581,594 | B1 | 6/2003 | Drew et al. |
| 7,225,811 | B2 * | 6/2007 | Ruiz ................ A61M 16/0683 2/171.2 |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 10,369,319 | B2 | 8/2019 | Formica et al. |
| 10,576,234 | B2 * | 3/2020 | Brown .............. A61M 16/0683 |
| 2009/0044808 | A1 | 2/2009 | Guney Memduh et al. |
| 2009/0050156 | A1 | 2/2009 | Ng et al. |
| 2010/0000534 | A1 | 1/2010 | Kooij et al. |
| 2012/0037161 | A1 | 2/2012 | Ging et al. |
| 2012/0199131 | A1 * | 8/2012 | Sofranko ............. A61M 16/06 128/206.21 |
| 2013/0324788 | A1 * | 12/2013 | Holley ................ A61M 16/06 128/202.16 |
| 2014/0305439 | A1 * | 10/2014 | Chodkowski ..... A61M 16/0605 128/207.11 |
| 2016/0038708 | A1 | 2/2016 | Amarasinghe et al. |
| 2016/0067441 | A1 | 3/2016 | Bearne et al. |
| 2016/0144144 | A1 | 5/2016 | Smith et al. |
| 2016/0250426 | A1 | 9/2016 | Morrison |
| 2016/0250436 | A1 | 9/2016 | Brown et al. |
| 2016/0367780 | A1 | 12/2016 | Ging et al. |
| 2017/0209661 | A1 | 7/2017 | Amarasinghe |
| 2017/0304576 | A1 | 10/2017 | Lawrenson et al. |
| 2017/0304577 | A1 | 10/2017 | Bearne et al. |
| 2018/0161535 | A1 | 6/2018 | Henry |
| 2018/0214655 | A1 | 8/2018 | Kooij et al. |
| 2018/0243522 | A1 | 8/2018 | Ng et al. |
| 2019/0105455 | A1 | 4/2019 | Ng et al. |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | 2011/121466 A1 | 10/2011 |
| WO | 2012/040791 A1 | 4/2012 |
| WO | 2012/045127 A1 | 4/2012 |
| WO | WO 2012/171072 A1 | 12/2012 |
| WO | WO 2013/020167 A1 | 2/2013 |
| WO | WO 2014/110626 A1 | 7/2014 |
| WO | 2015/079396 A1 | 6/2015 |
| WO | WO 2016/082001 A1 | 6/2016 |
| WO | WO 2017/158476 A2 | 9/2017 |
| WO | 2019/111135 A1 | 6/2019 |

OTHER PUBLICATIONS

International Preliminary Report on Patentability dated Dec. 28, 2021 issued in PCT/IB2020/055965 (7 pages).
"*Respiratory Physiology*", by John B. West, Lippincott Williams & Wilkins, 9$^{th}$ edition published 2012 (8 pages).
International Search Report dated Aug. 21, 2020 issued in International Application No. PCT/IB2020/055966 (9 pages).
Written Opinion dated Aug. 21, 2020 issued in International Application No. PCT/IB2020/055966 (6 pages).
International Search Report dated Sep. 4, 2020 issued in International Application No. PCT/IB2020/055965 (10 pages).
Written Opinion dated Sep. 4, 2020 issued in International Application No. PCT/IB2020/055965 (6 pages).
Supplementary Search Report dated Aug. 3, 2022 in corresponding EP Patent Application 20831746.1 (10 pages).

* cited by examiner

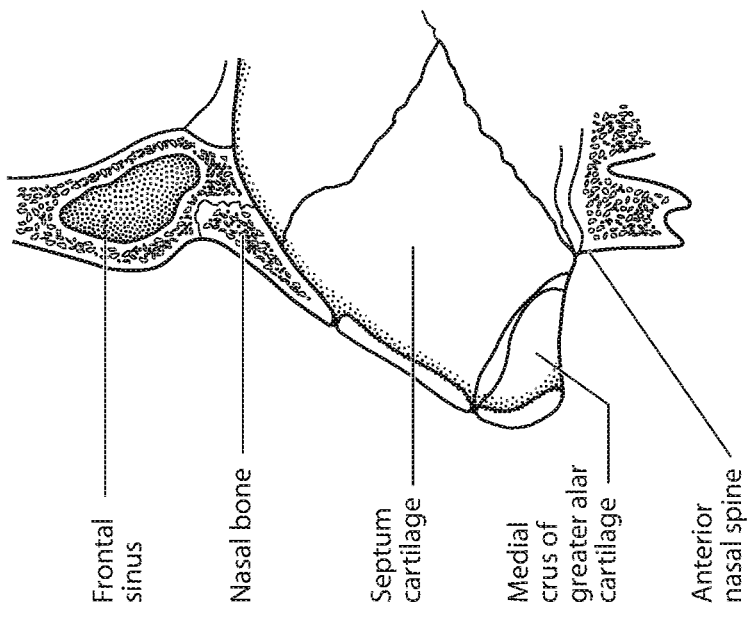
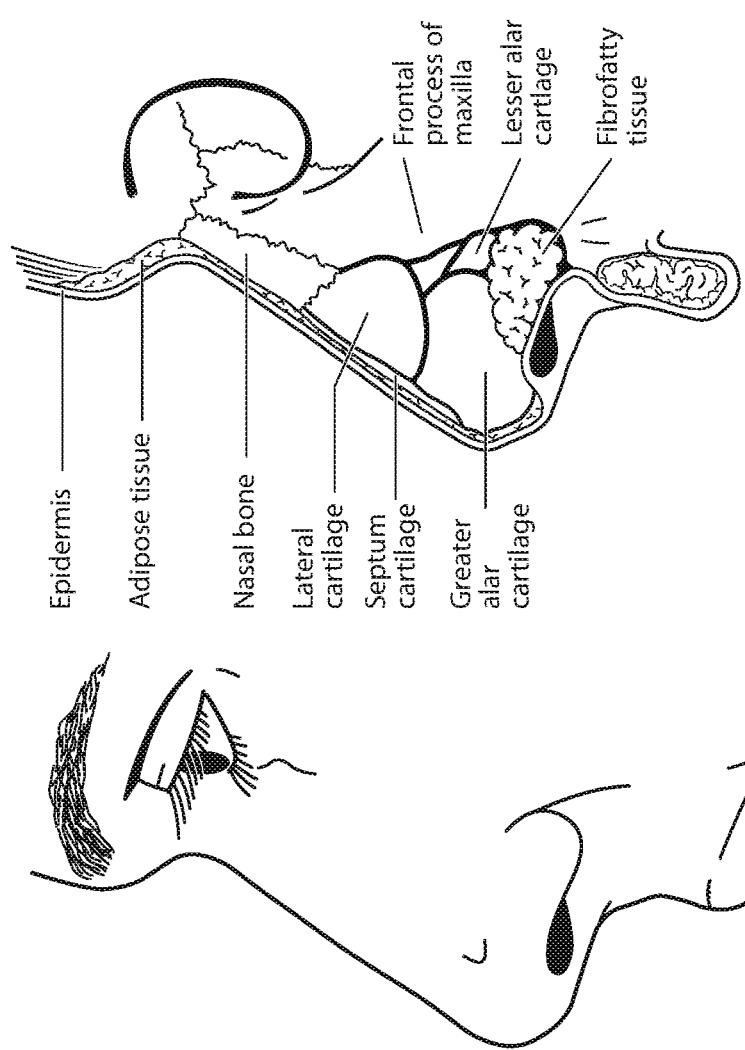
FIG. 2I
FIG. 2H
FIG. 2G

Relatively Large Positive Curvature

Relatively Small Positive Curvature

Zero Curvature

Relatively Small Negative Curvature

Relatively Large Negative Curvature

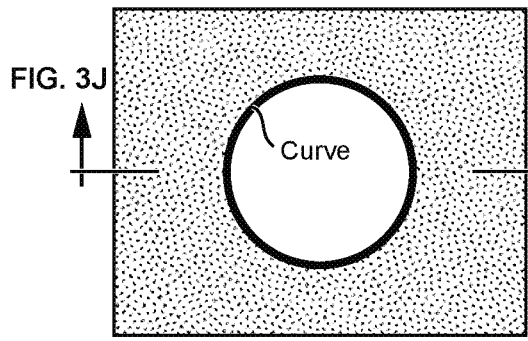
FIG. 3I
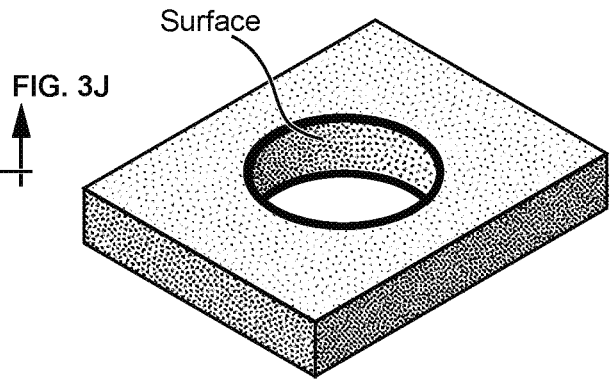
FIG. 3K
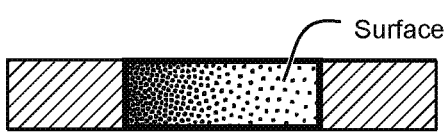
FIG. 3J
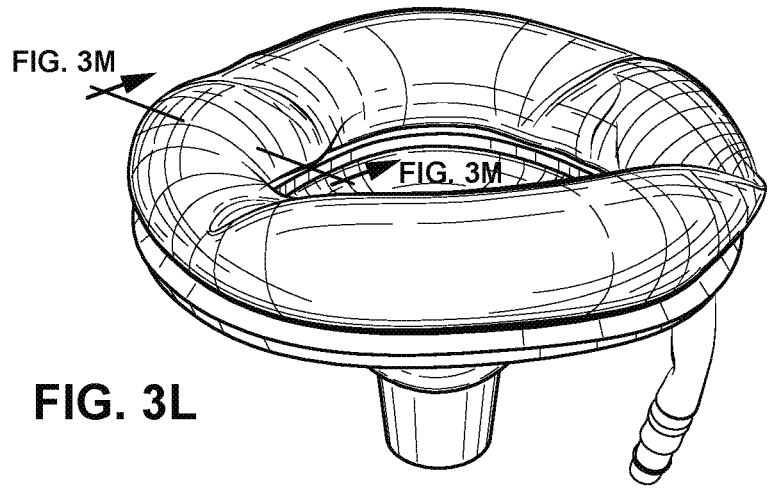
FIG. 3L
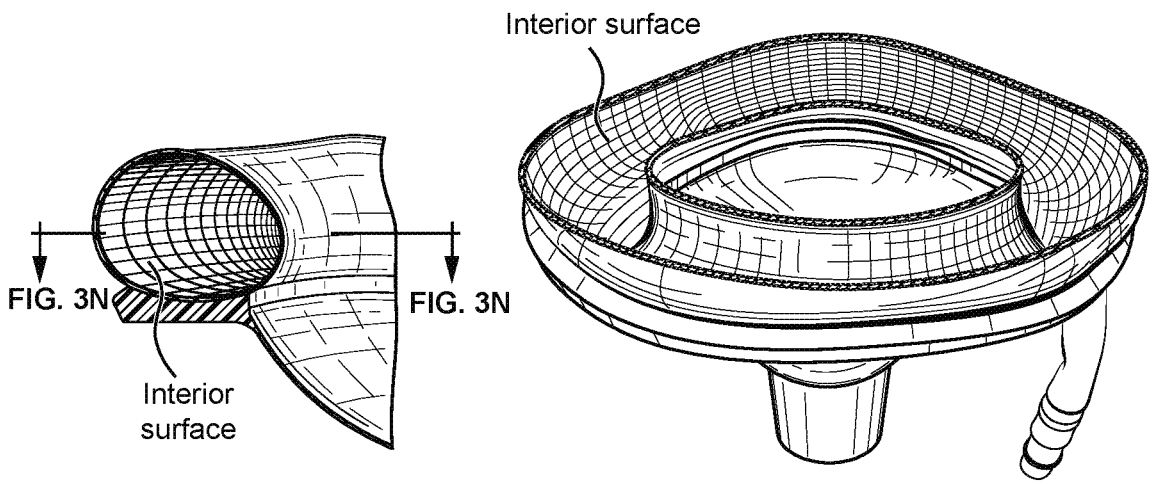
FIG. 3M    FIG. 3N

Left-hand rule
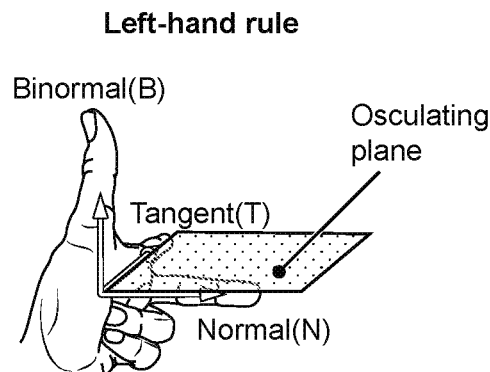
FIG. 3O
Right-hand rule
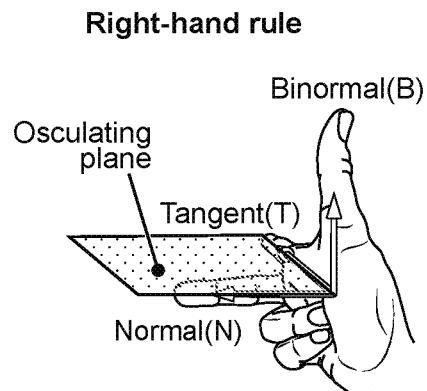
FIG. 3P
Left ear helix
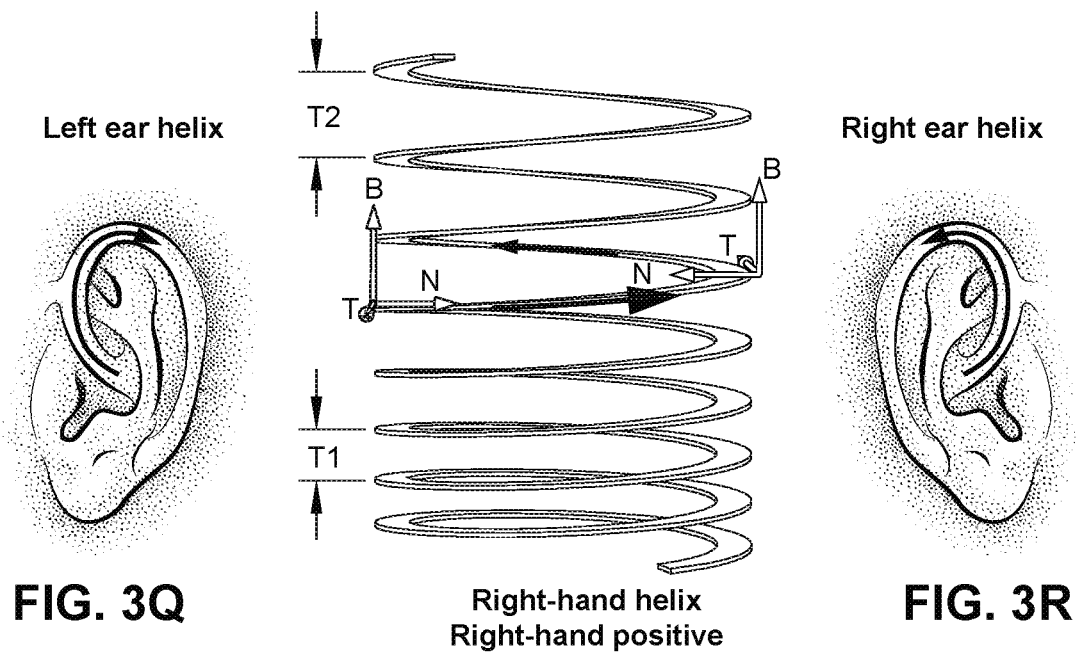
FIG. 3Q
Right ear helix
FIG. 3R
Right-hand helix
Right-hand positive
FIG. 3S
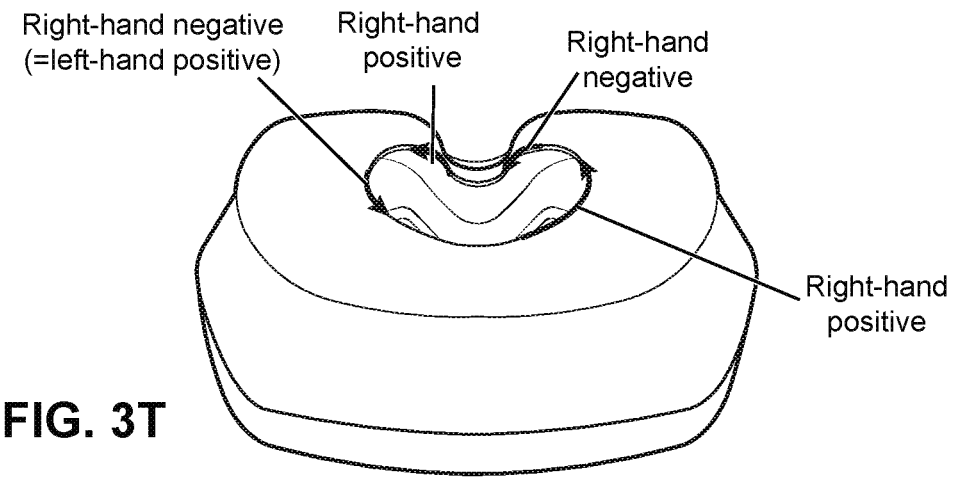
FIG. 3T

ADJUSTABLE HEADGEAR THAT IS EASY TO DON AND DOFF

1 CROSS-REFERENCE TO RELATED APPLICATIONS

This application is the U.S. national phase of International Application No. PCT/IB2020/055966 filed Jun. 24, 2020 which designated the U.S. and claims priority to Australian Provisional Patent Application No. 2019902270 filed Jun. 28, 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

An aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a positioning and stabilising structure for a full-face mask or ultra-compact full face mask of a patient interface, the positioning and stabilising structure comprising:

a superior strap portion;

an inferior strap portion; and an anterior strap portion connected to or formed integrally with the superior strap portion and inferior strap portion, wherein the anterior strap portion is connected or connectable to a connection portion which engages an interfacing portion of the patient interface, and wherein the superior strap portion and the inferior strap portion join the anterior strap portion anterior to the patient's ear, in use.

Another form of the present technology comprises a patient interface comprising a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure for a full-face, the positioning and stabilising structure comprising:
  a superior strap portion;
  an inferior strap portion; and
  anterior strap portions, each having a generally triangular surface with a first width and a second width being less than the first width and disposed more anterior while in use, the superior strap portion and the inferior strap portion each connected to or formed integrally with each anterior strap portion at a respective corner of the generally triangular surface, the anterior strap portion connected or connectable to a connection portion which engages the plenum chamber, the connection portion being permanently fixed to the plenum chamber; and
  wherein the superior strap portion and the inferior strap portion join the anterior strap portions anterior to the patient's ears, in use; and
  wherein the anterior strap portion forms a loop when connected with the connection portion, the loop is adjustable to adjust the direction and magnitude of a headgear force.

In examples: a) the superior strap portion is configured to overlie an upper cheek region of the patient's face; b) the inferior strap portion is configured to overlie a region of the patient's head below and behind one of the patient's ears; and/or c) an anterior strap portion is provided on each side of the positioning and stabilising structure, each anterior strap portion connected to a respective inferior strap portion and anterior strap portion.

Another form of the present technology comprises a positioning and stabilising structure for a patient interface, the positioning and stabilising structure comprising:
  a superior strap portion;
  an inferior strap portion; and
  an anterior strap portion connected to or formed integrally with the superior strap portion and the inferior strap portion;
    the anterior strap portion comprising a strap receiving portion and a strap attachment portion which is releasably connectable to the strap receiving portion such that the anterior strap portion forms a loop, wherein in use the loop engages a connection portion which engages an interfacing portion of the patient interface;
    wherein the strap receiving portion is configured to engage the strap attachment portion in a selected one of a plurality of possible positions, wherein the plurality of possible positions comprises a plurality of possible angular positions of the strap attachment portion relative to the strap receiving portion.

Another form of the present technology is a patient interface that comprises a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure for a patient interface, the positioning and stabilising structure comprising:
  a superior strap portion;
  an inferior strap portion;
  at least one anterior strap portion connected to or formed integrally with the superior strap portion and the inferior strap portion;
  the anterior strap portion comprising a strap receiving portion and a strap attachment portion which is releasably connectable to the strap receiving portion such that the anterior strap portion forms a loop, wherein in use the loop engages a connection portion which engages the plenum chamber, the connection portion being permanently coupled to the plenum chamber;
  wherein the strap receiving portion is configured to engage the strap attachment portion in a selected one of a plurality of possible positions, wherein the plurality of possible positions comprises a plurality of possible angular positions of the strap attachment portion relative to the strap receiving portion, and wherein the strap attachment portion is connected completely within the boundary of the strap receiving portion in any one of the plurality of possible positions, and wherein the angle between the strap attachment portion and the strap receiving portion when connected is configured to cause pivotable movement in the plenum chamber and/or the seal forming structure.

In examples: a) the superior strap portion and the inferior strap portion join the anterior strap portion anterior to the patient's ear, in use; b) the superior strap portion is configured to overlie an upper cheek region of the patient's face; c) the inferior strap portion is configured to overlie a region of the patient's head below and behind one of the patient's ears and/or d) an anterior strap portion is provided on each side of the positioning and stabilising structure, each anterior strap portion connected to a respective inferior strap portion and anterior strap portion.

Another form of the present technology comprises a positioning and stabilising structure for a patient interface, the positioning and stabilising structure comprising:
  a superior strap portion;
  an inferior strap portion; and
  an anterior strap portion connected to or formed integrally with the superior strap portion and the inferior strap portion;
    the anterior strap portion comprising a strap receiving portion and a strap attachment portion which is releasably connectable to the strap receiving portion such that the anterior strap portion forms a loop, wherein in use the loop engages a connection portion which engages an interfacing portion of the patient interface;

wherein the strap receiving portion is configured to engage the strap attachment portion in a selected one of a plurality of possible positions to adjust the direction and magnitude of the headgear vector.

Another form of the present technology is a patient interface that comprises a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure for a patient interface, the positioning and stabilising structure comprising:
  a superior strap portion;
  an inferior strap portion;
  at least one anterior strap portion connected to or formed integrally with the superior strap portion and the inferior strap portion;
  the anterior strap portion comprising a strap receiving portion and a strap attachment portion which is permanently coupled to the strap receiving portion such that the anterior strap portion forms a loop, wherein in use the loop engages a connection portion which engages the plenum chamber;
  wherein the strap receiving portion is configured to engage the strap attachment portion in a selected one of a plurality of possible positions to adjust the direction and magnitude of the headgear vector, and wherein the headgear vector is configured to cause pivotable movement in the plenum chamber and/or seal forming structure.

In examples: a) the superior strap portion and the inferior strap portion join the anterior strap portion anterior to the patient's ear, in use; b) the superior strap portion is configured to overlie an upper cheek region of the patient's face; c) the inferior strap portion is configured to overlie a region of the patient's head below and behind one of the patient's ears; d) the width of the strap receiving portion decreases from a posterior end to an anterior end thereof, and wherein the width of the strap receiving portion is not narrower than the strap attachment portion between the posterior end and the anterior end; e) the strap attachment portion comprises a hook material; f) the strap receiving portion comprises a patient facing surface and an opposite non-patient facing surface, wherein the non-patient facing surface is provided with an unbroken loop material to engage the hook material of the strap attachment portion; g) wherein a maximum width of the strap receiving portion is approximately two to approximately four times wider than the maximum width of the strap attachment portion; h) the anterior strap portion passes through a slot of the connection portion; i) the connection portion attaches to a frame which connects to a cushion module of the plenum chamber; j) the connection portion attaches directly to a cushion module of the plenum chamber; k) at least a part of the anterior strap portion is configured to overlie the cheek region of the patient's face; l) the superior strap portion, inferior strap portion and anterior strap portions are integrally formed from a single piece of material; m) the superior strap portion is joined to the inferior strap portion by a posterior connecting strap portion; n) the superior strap portion connects to a crown strap portion; o) the inferior strap connects to a back strap portion; p) the anterior strap portion comprises less stretchability compared to other portions of the positioning and stabilising structure; q) the superior strap portion comprises less stretchability compared to other portions of the positioning and stabilising structure; r) the inferior strap portion comprises a greater stretchability compared to other portions of the positioning and stabilising structure; s) the posterior connecting strap portion comprises a greater stretchability than the superior strap portion and a lesser stretchability than the inferior strap portion; t) a plurality of holes in a region of the positioning and stabilising structure increases the stretchability of that region; u) the positioning and stabilising structure comprises an anterior strap portion provided on each side of the positioning and stabilising structure, each anterior strap portion connected to a respective inferior strap portion and anterior strap portion and/or (v) the greatest stretch capability is between the posterior connecting strap portion and the inferior strap portion.

Another form of the present technology comprises patient interface comprising:

a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure to provide a force to hold the seal-forming structure in a therapeutically effective position on a patient's head, the positioning and stabilising structure comprising:
  a superior strap portion;
  an inferior strap portion;
  a posterior connecting strap portion connected to or formed integrally with the superior strap portion and the inferior strap portion;
  an anterior strap portion connected to or formed integrally with the superior strap portion and the inferior strap portion, and spaced apart from the posterior connecting strap portion;
    wherein the anterior strap portion comprises:
      a strap receiving portion; and
      a strap attachment portion which is releasably connectable to the strap receiving portion such that the anterior strap portion forms a loop, wherein in use the loop engages a connection portion which engages the plenum chamber;

wherein the strap receiving portion is configured to engage the strap attachment portion in a selected one of a plurality of possible positions, wherein the posterior connecting strap portion is constructed from a mesh material different than the material used to construct the superior strap portion and the inferior strap portion; and wherein the posterior connecting strap portion has a greater stretch capability than the superior strap portion and a lesser stretch capability than the inferior strap portion, the stretch capabilities allowing the positioning and stabilizing structure to be removable from the patient's head when the loop engages the connection portion.

In examples a) the positioning and stabilizing structure further comprises a back strap connected to or formed integrally with the posterior connecting strap portion, the back strap having a stretch capability greater than the superior strap portion; b) the inferior strap portion having a greater stretch capability than the back strap; c) the inferior strap portion includes indicator lines, which act as a visual cue to indicate stretch capability; d) the mesh material is flush with the textile material; e) the mesh material is recessed with respect to the textile material; f) the superior strap portion is constructed from a foam within the textile material in order to increase the rigidity of the positioning and stabilizing structure; g) the positioning and stabilizing structure further comprises a crown strap portion connected to or formed integrally with the posterior connecting strap portion, the crown strap portion having a stretch capability less than the posterior connecting strap portion; h) the crown strap portion and the superior strap portion are inextensible; i) the strap receiving portion is configured to engage the strap attachment portion in order to adjust the direction and magnitude of a headgear vector, which is configured to cause pivotable movement in the plenum chamber and/or the seal-forming structure; j) the plurality of possible positions comprises a plurality of possible angular positions of the strap attachment portion relative to the strap receiving portion; k) a selected angular position of the plurality of possible angular positions does not change when the positioning and stabilizing structure is removed from the patient's head; l) the strap attachment portion includes a tab configured to allow engagement with the connection portion, and limit disengagement from the connection portion; m) the crown strap portion comprises a left crown strap portion and a right crown strap portion, wherein one of the left and right crown strap portions has a buckle through which the end of the other of the left and right crown strap portions can pass and be looped back and secured onto itself in order to couple the left crown strap portion to the right crown strap portion; and/or n) the positioning and stabilizing structure is configured to be removed from the patient's head by decoupling the left crown strap portion and the right crown strap portion, and without disengaging the strap attachment portion from the strap receiving portion.

Another form of the present technology comprises a patient interface comprising:

a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure to provide a force to hold the seal-forming structure in a therapeutically effective position on a patient's head, the positioning and stabilising structure comprising:

a superior strap portion;

an inferior strap portion;

an anterior strap portion connected to or formed integrally with the superior strap portion and the inferior strap portion;

wherein the anterior strap portion comprises:

a strap receiving portion; and a strap attachment portion which is releasably connectable to the strap receiving portion such that the anterior strap portion forms a loop, wherein in use the loop engages a connection portion which engages the plenum chamber;

a tab coupled to the anterior strap and inclined with respect to the anterior strap portion;

wherein the strap receiving portion is configured to engage the strap attachment portion in a selected one of a plurality of possible positions to adjust the direction and magnitude of a headgear vector;

wherein the connection portion includes a slot and the tab is configured to permit the strap attachment portion to pass through the slot in a first direction prior to connecting to the strap receiving portion; and wherein the tab is configured to limit the strap attachment portion from passing through the slot in a second direction opposite to the first direction in order to retain the loop.

In examples a) the tab is formed from the same material as the strap attachment portion; b) the tab forms an obtuse angle with respect to the strap attachment portion in a relaxed position; c) the tab and the strap attachment portion are disposed adjacent to the strap attachment portion; d) the tab includes a hook material configured to engage with a loop material of the strap receiving portion; e) the tab is a one-way hinge and is limited in its movement toward the strap attachment position past the relaxed position; f) the strap attachment portion is permitted to pass through the slot in the second direction when the patient applies a force to the tab directed toward the strap receiving portion the connection portion is permanently coupled to the plenum chamber; g) the slot is fully formed within the connection member; h) the positioning and stabilizing structure is removable from the patient's head without moving the strap attachment portion through the slot in the second direction; i) the positioning and stabilizing structure is removable from the patient's head while the strap attachment portion is connected to the strap receiving portion; j) the posterior connecting strap portion includes a plurality of holes configured to provide increased stretchability to the posterior connecting strap portion; k) the holes are arranged proximate to the inferior strap portion; l) the holes are arranged in a pattern on the posterior connecting strap portion; m) the posterior connecting strap portion includes a mesh material having the holes; and/or n) the mesh material is different than the material used to construct the superior strap portion and the inferior strap portion.

Another form of the present technology comprises a patient interface comprising a plenum chamber pressurisable to a therapeutic pressure of at least 6 cmH$_2$O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure to provide a force to hold the seal-forming structure in a therapeutically effective position on a patient's head, the positioning and stabilising structure comprising:

a frame coupled to the plenum chamber, the frame comprises
a tab including at least one groove, and
a movable portion having a slot and a projection, the projection selectively engagable with the at least one groove; and
an anterior strap portion that comprises:
a strap receiving portion; and
a strap attachment portion which is releasably connectable to the strap receiving portion such that the anterior strap portion forms a loop, wherein in use the loop engages the slot;

wherein the tab and the at least one groove form a ratchet system, the ratchet system configured to move the anterior strap portion, in use.

In examples a) the at least one groove includes three spaced apart grooves, the projection selectively engagable with any of the three grooves; b) the tab is movable between a relaxed position where the projection is configured to engage the at least one groove, and a flexed position where the projection and the at least one groove are configured to be disengaged; c) the tab is biased toward the relaxed position; d) the frame further includes a central portion, the movable portion being movable relative to the central portion; e) the tab is coupled to the central portion; f) the movable portion is slidable relative to the central portion; g) movement of the movable portion is locked when the projection engages the at least one groove; and/or h) movement of the movable portion is configured to cause the seal-forming structure to rotate in the mid-sagittal plane.

Another form of the present technology comprises a patient interface comprising:

a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure to provide a force to hold the seal-forming structure in a therapeutically effective position on a patient's head, the positioning and stabilising structure comprising:

a superior strap portion;
an inferior strap portion;
a posterior connecting strap portion connected to the superior strap portion;
a lower back strap connected to the inferior strap portion; and
an upper back strap connected between the posterior connecting strap portion and the lower back strap.

In examples a) the posterior connecting strap portion and the upper back strap are integrally formed as a one-piece construction; b) the lower back strap is spaced apart from the posterior connecting strap portion; c) the lower back strap is constructed from a material having a greater stretchability than the upper back strap; and/or d) the posterior connecting strap portion has a greater length than the upper back strap.

Another form of the present technology comprises a patient interface comprising a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure to provide a force to hold the seal-forming structure in a therapeutically effective position on a patient's head.

Another form of the present disclosure is a positioning and stabilising structure to provide a force to hold the seal-forming structure in a therapeutically effective position on a patient's head, the positioning and stabilising structure comprising:

a superior strap portion;
an inferior strap portion;
a posterior connecting strap portion connected to or formed integrally with the superior strap portion and the inferior strap portion;
an anterior strap portion connected to or formed integrally with the superior strap portion and the inferior strap portion, and spaced apart from the posterior connecting strap portion;
wherein the anterior strap portion comprises:
a strap receiving portion; and
a strap attachment portion which is releasably connectable to the strap receiving portion such that the anterior strap portion forms a loop, wherein in use the loop engages a connection portion which engages the plenum chamber;
wherein the strap receiving portion is configured to engage the strap attachment portion in a selected one of a plurality of possible positions, wherein the posterior connecting strap portion is constructed from a mesh material different than the material used to construct the superior strap portion and the inferior strap portion; and wherein the posterior connecting strap portion has a greater stretch capability than the superior strap portion and a lesser stretch capability than the inferior strap portion, the stretch capabilities allowing the positioning and stabilizing structure to be removable from the patient's head when the loop engages the connection portion.

Another form of the present disclosure is a positioning and stabilising structure to provide a force to hold the seal-forming structure in a therapeutically effective position on a patient's head, the positioning and stabilising structure comprising:
 a superior strap portion;
 an inferior strap portion;
 an anterior strap portion connected to or formed integrally with the superior strap portion and the inferior strap portion;
  wherein the anterior strap portion comprises:
   a strap receiving portion; and
   a strap attachment portion which is releasably connectable to the strap receiving portion such that the anterior strap portion forms a loop, wherein in use the loop engages a connection portion which engages the plenum chamber;
  a tab coupled to the anterior strap portion and inclined with respect to the anterior strap portion;
  wherein the strap receiving portion is configured to engage the strap attachment portion in a selected one of a plurality of possible positions to adjust the direction and magnitude of a headgear vector;
  wherein the connection portion includes a slot and the tab is configured to permit the strap attachment portion to pass through the slot in a first direction prior to connecting to the strap receiving portion; and
  wherein the tab is configured to limit the strap attachment portion from passing through the slot in a second direction opposite to the first direction in order to retain the loop.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
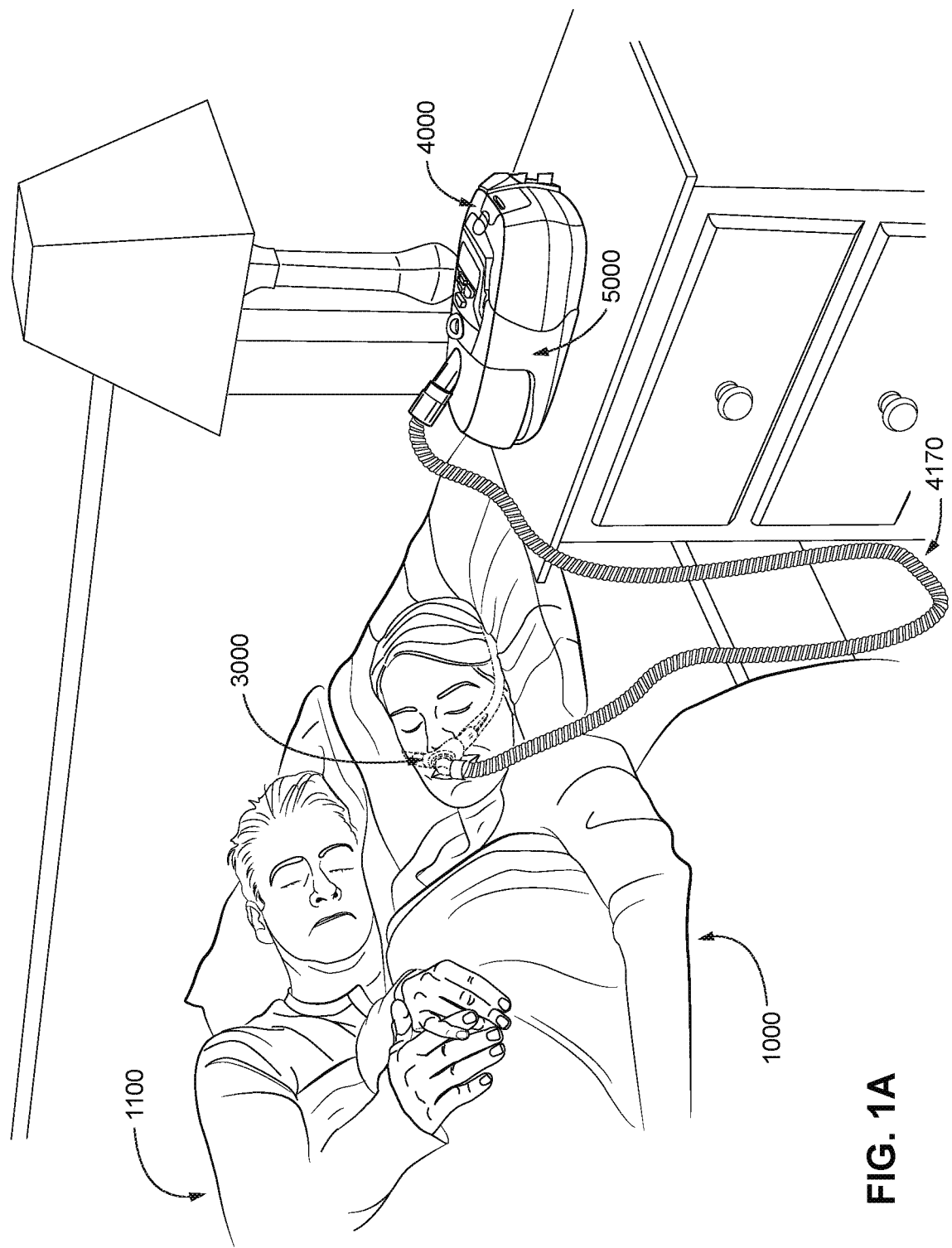
Figure 1B:
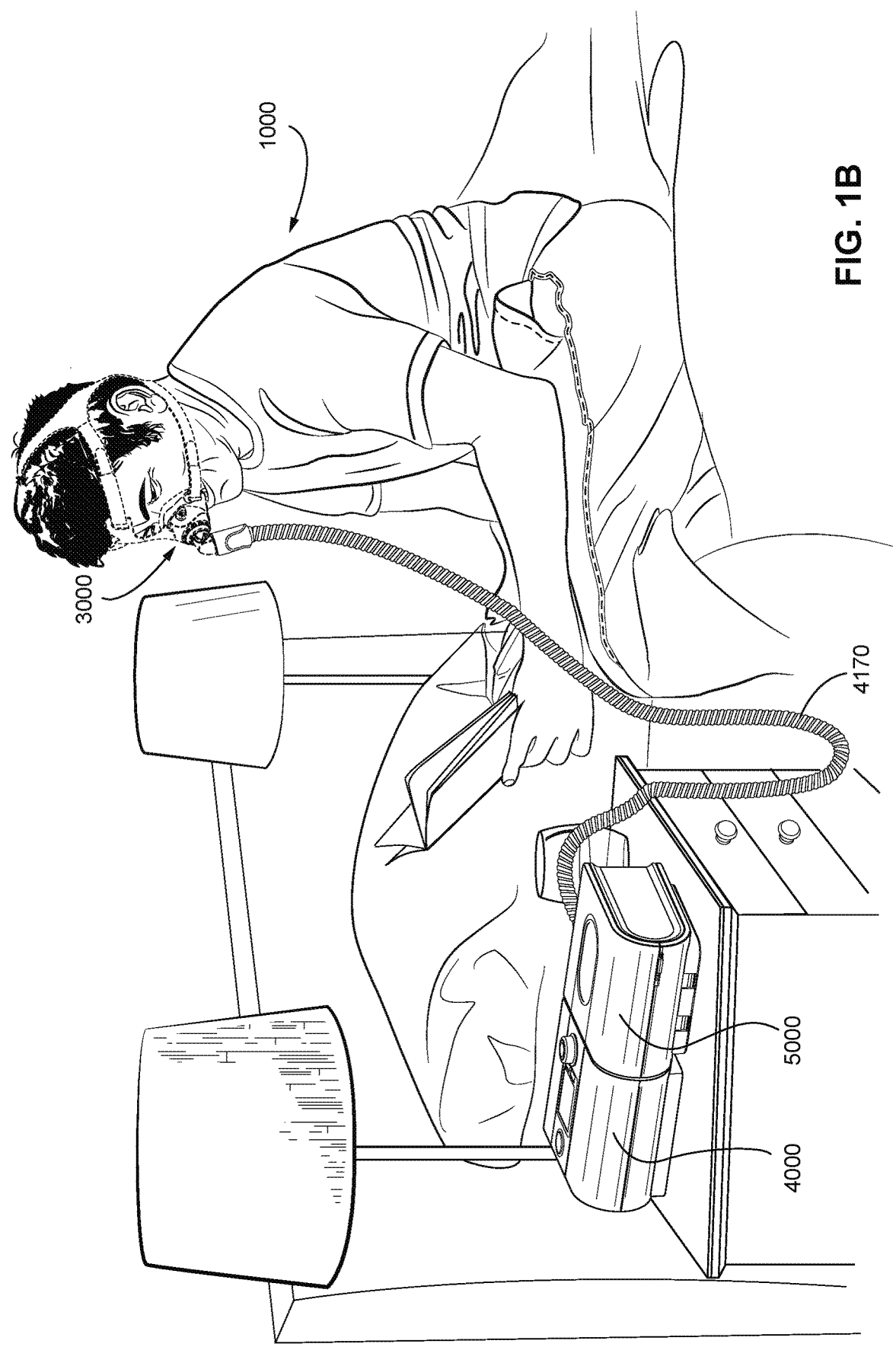
Figure 1C:
Figure 2A:
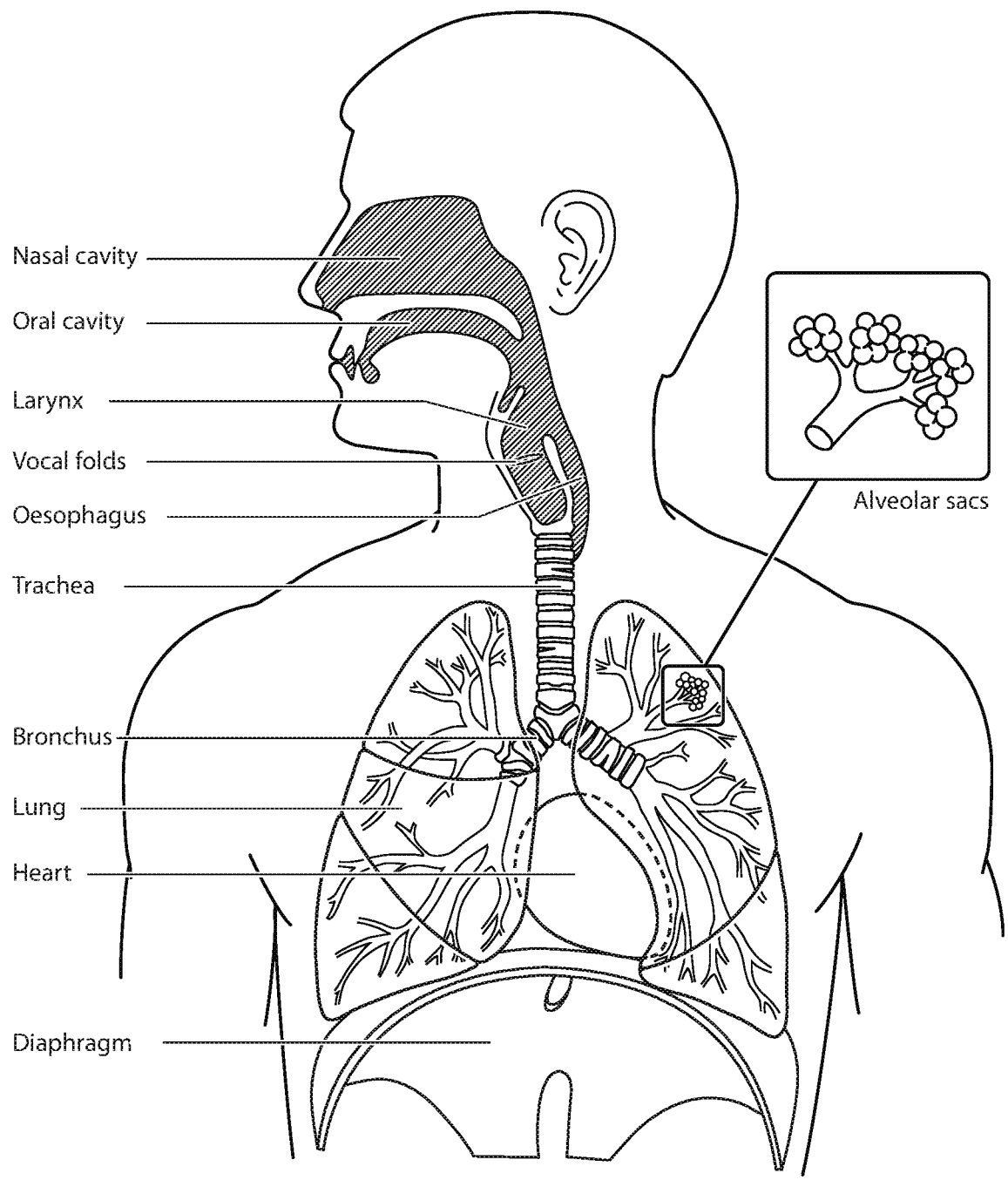
FIG. 2A shows an overview of a human respiratory system including the nasal and oral cavities, the larynx, vocal folds, oesophagus, trachea, bronchus, lung, alveolar sacs, heart and diaphragm.
Figure 2B:
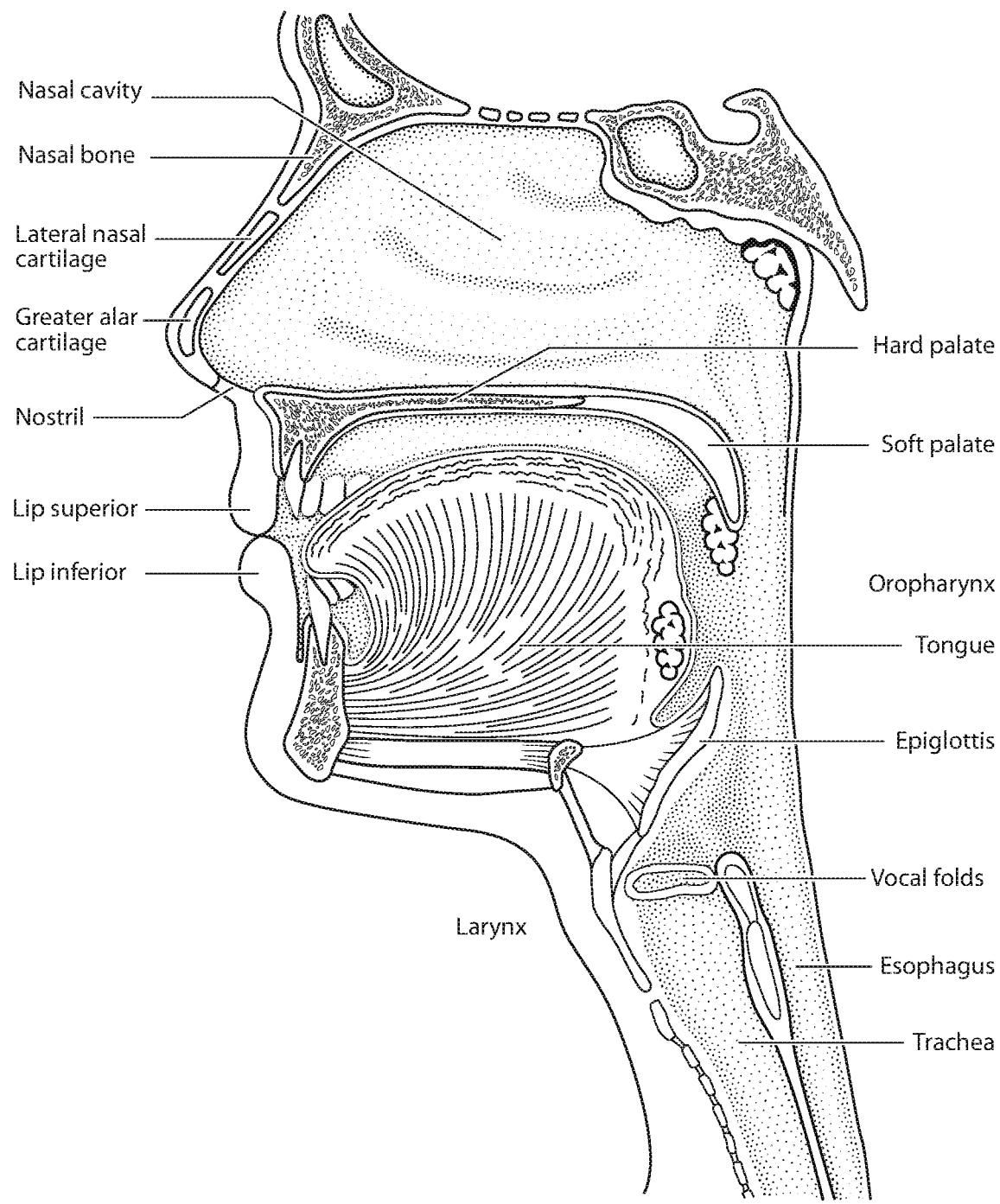
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
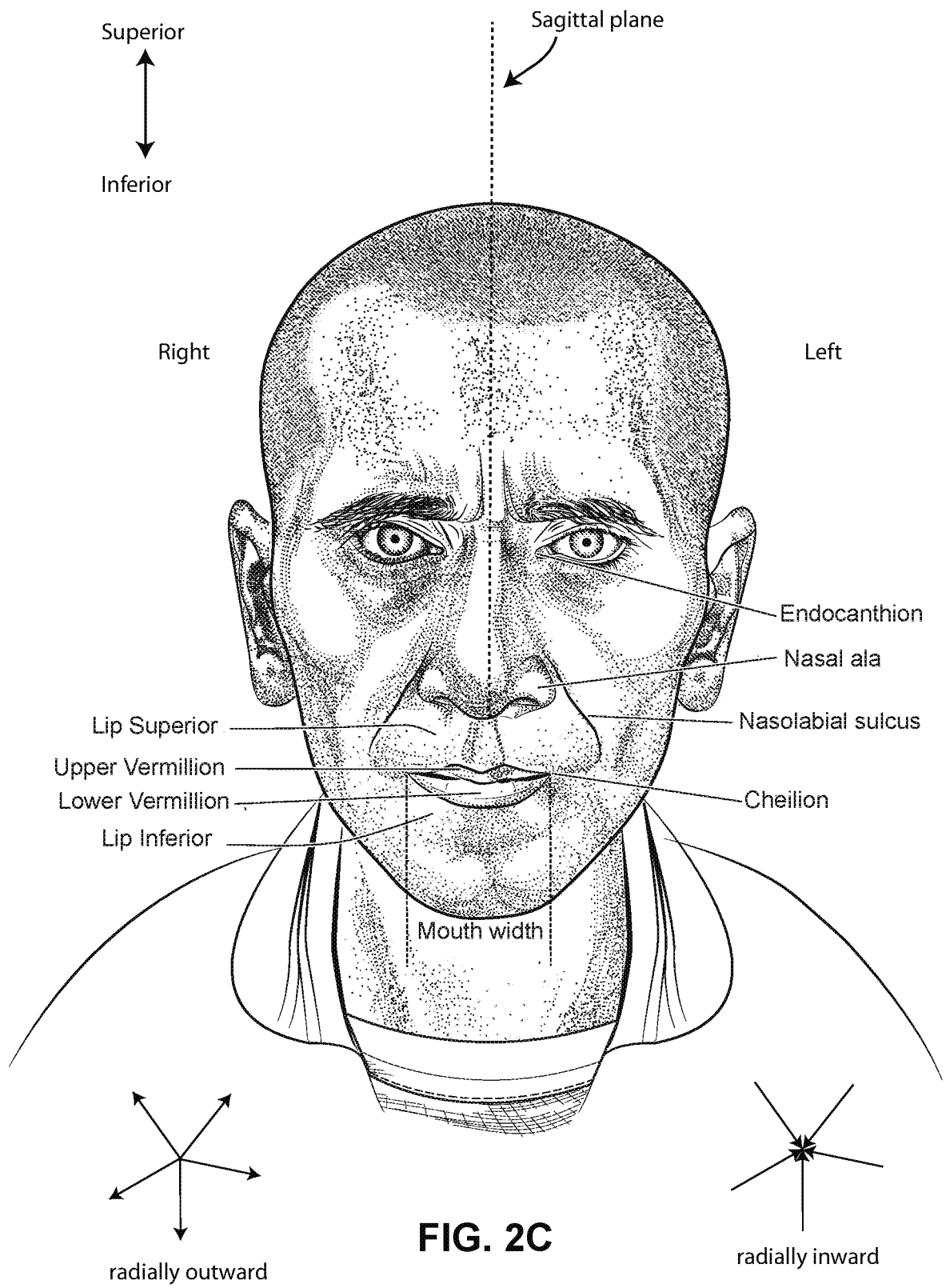
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
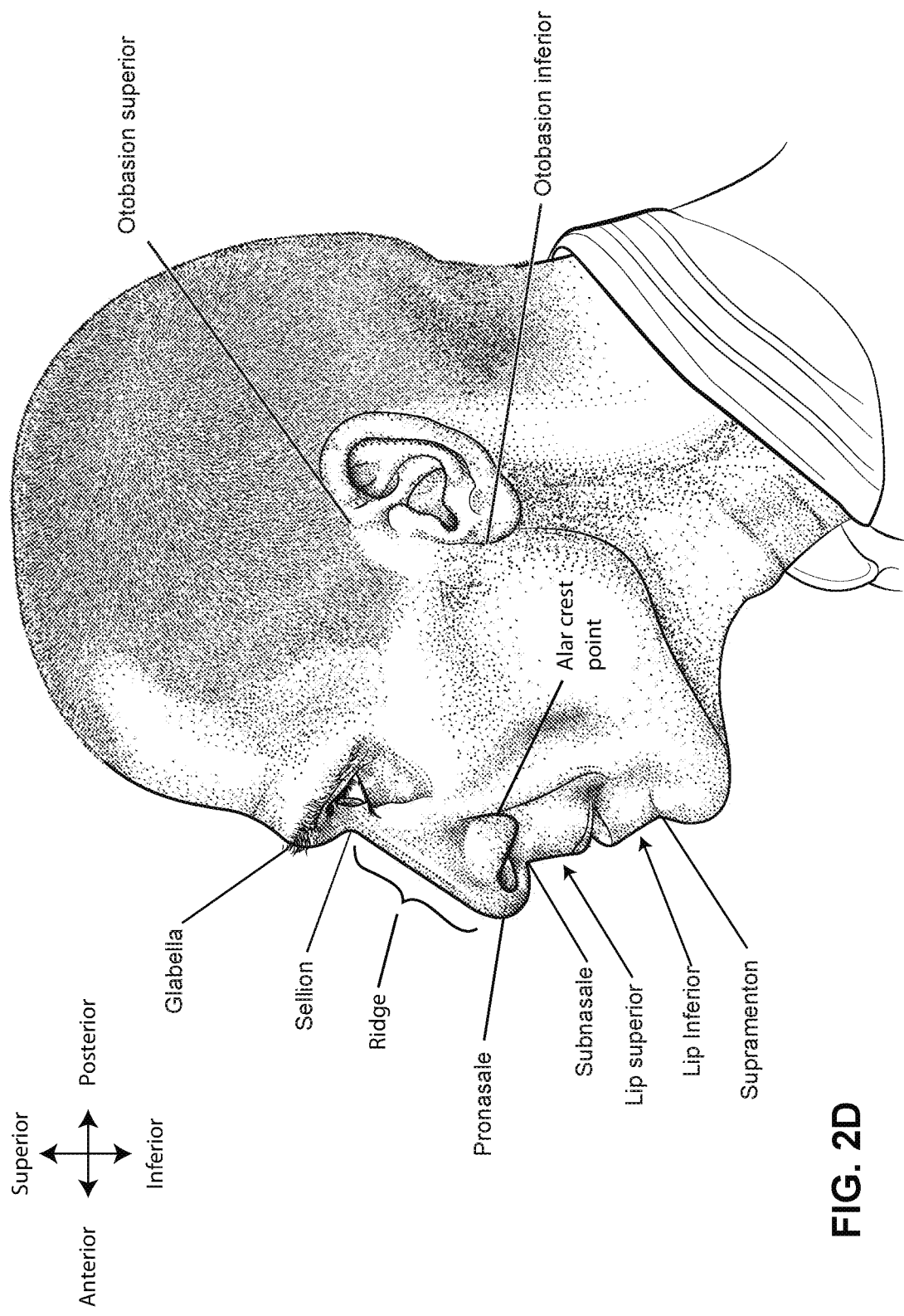
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
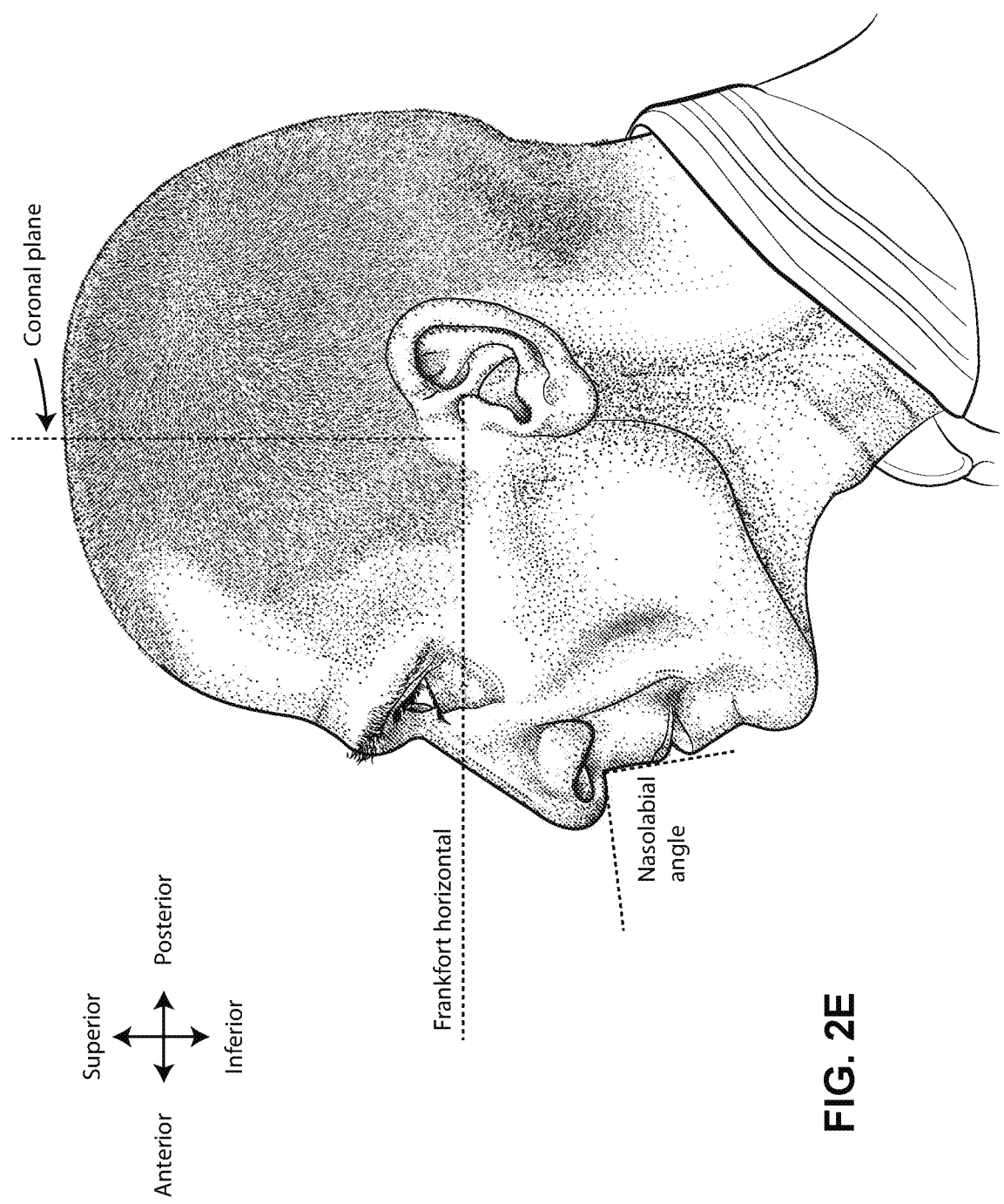

FIG. 2E is a further side view of a head. The approximate locations of the Frankfort horizontal and nasolabial angle are indicated. The coronal plane is also indicated.

Figure 2F:
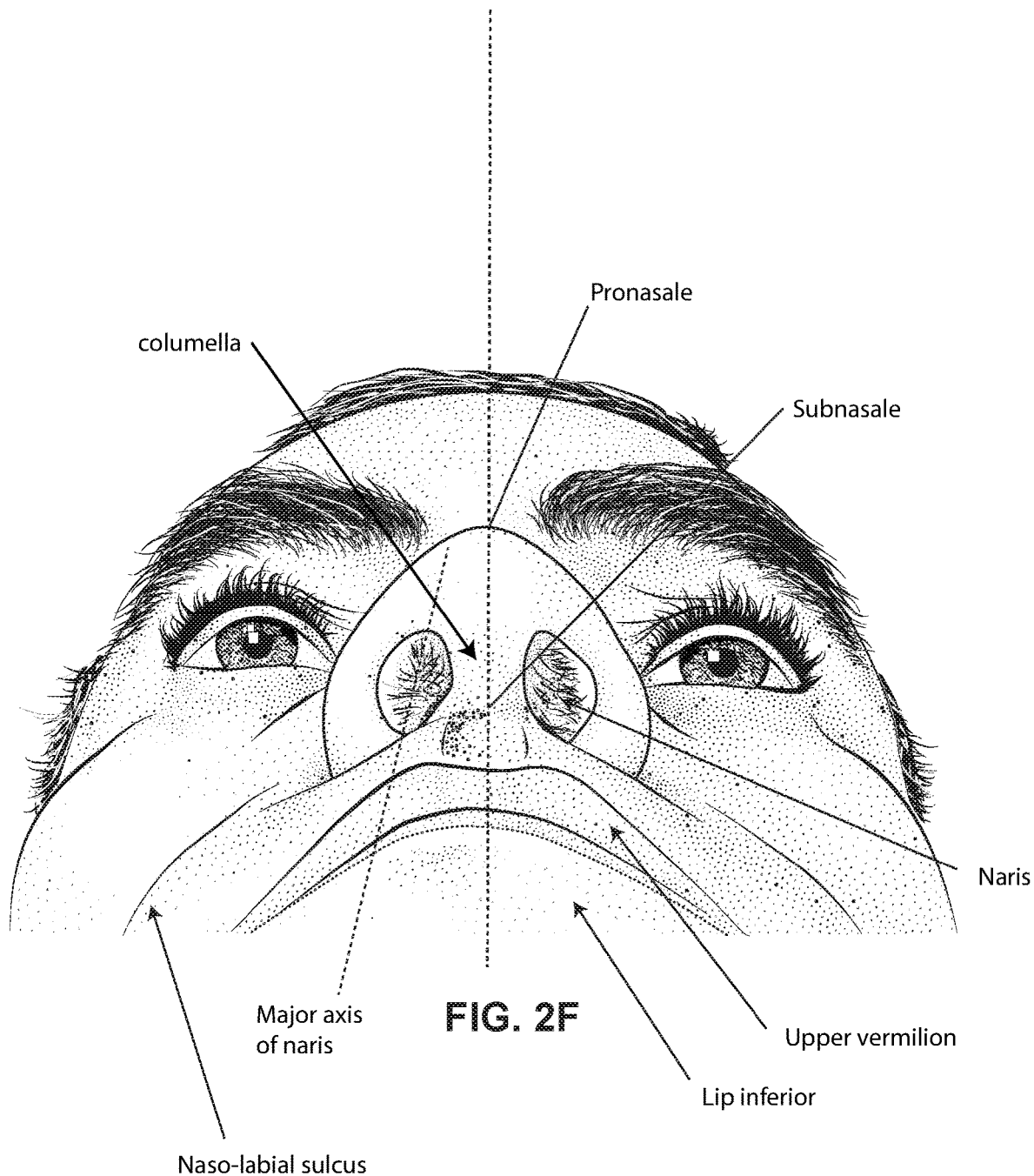

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
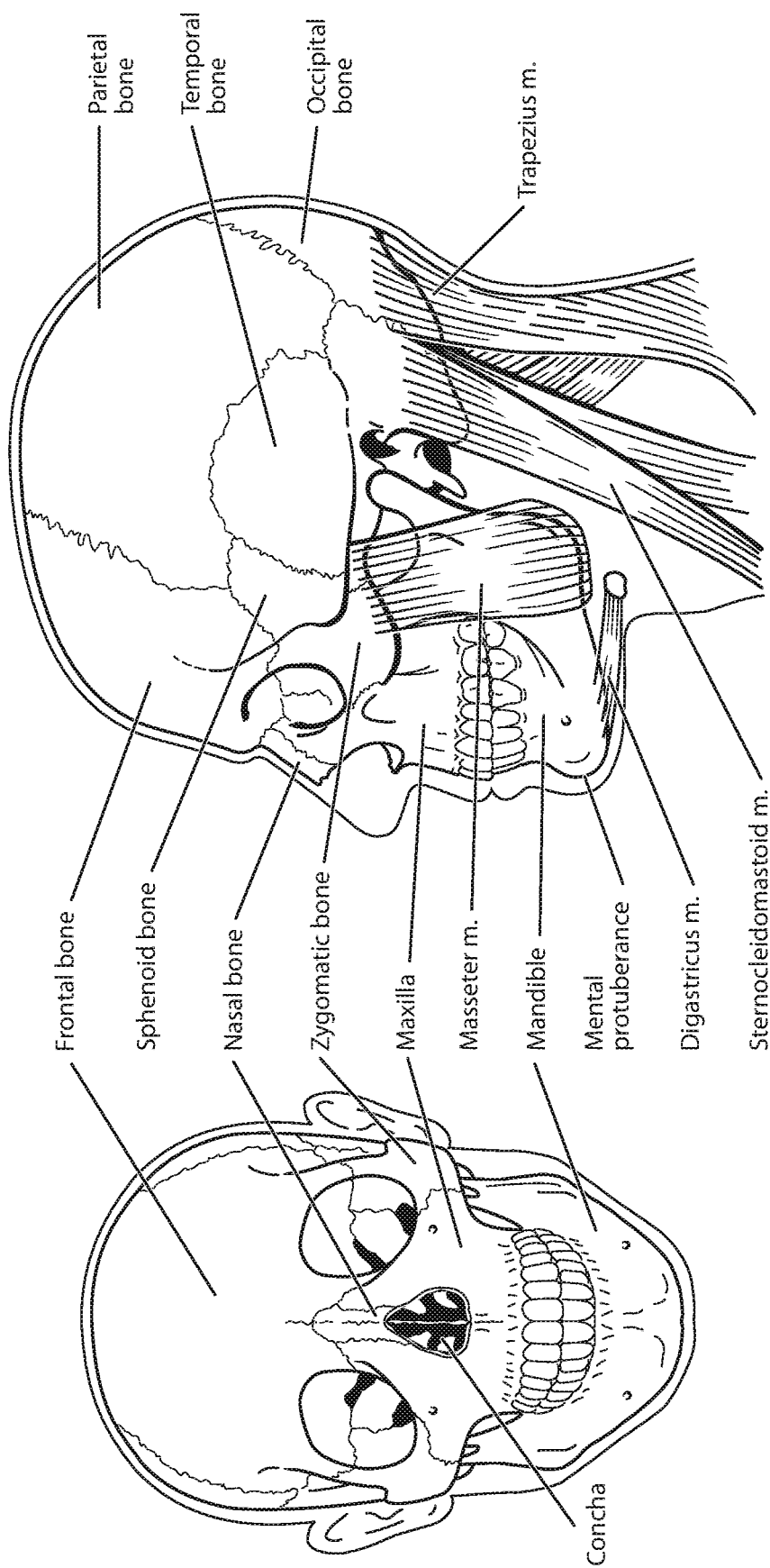

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
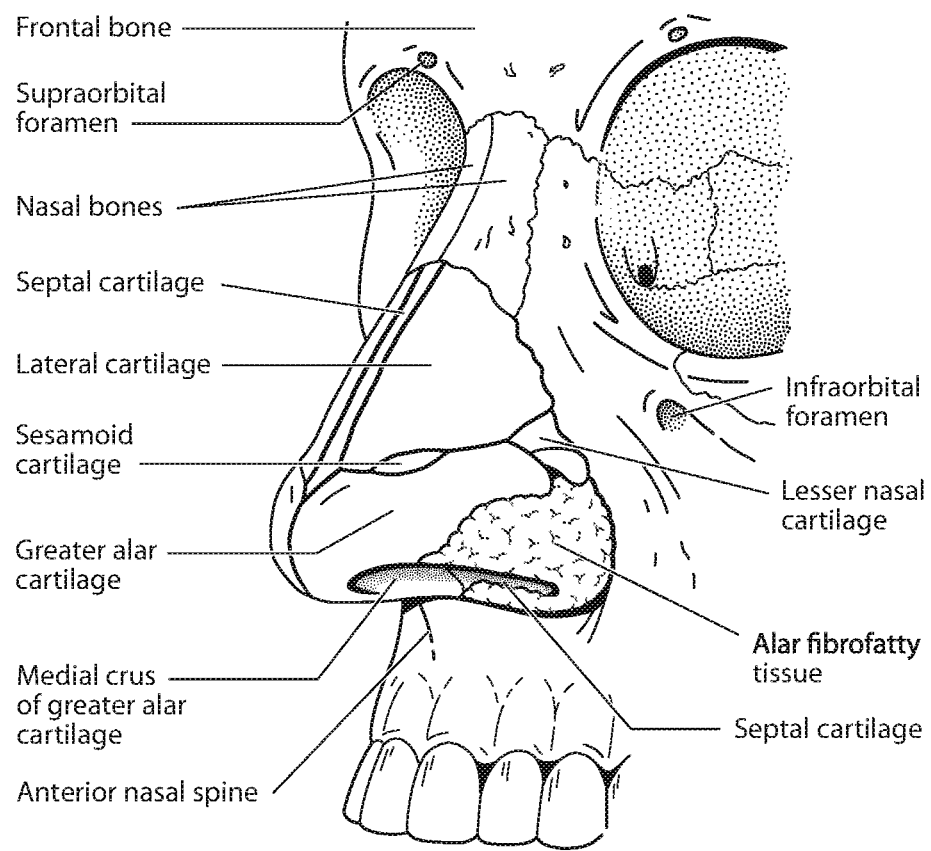

FIG. 2L shows an anterolateral view of a nose.

4.3 Patient Interface

Figure 3A:
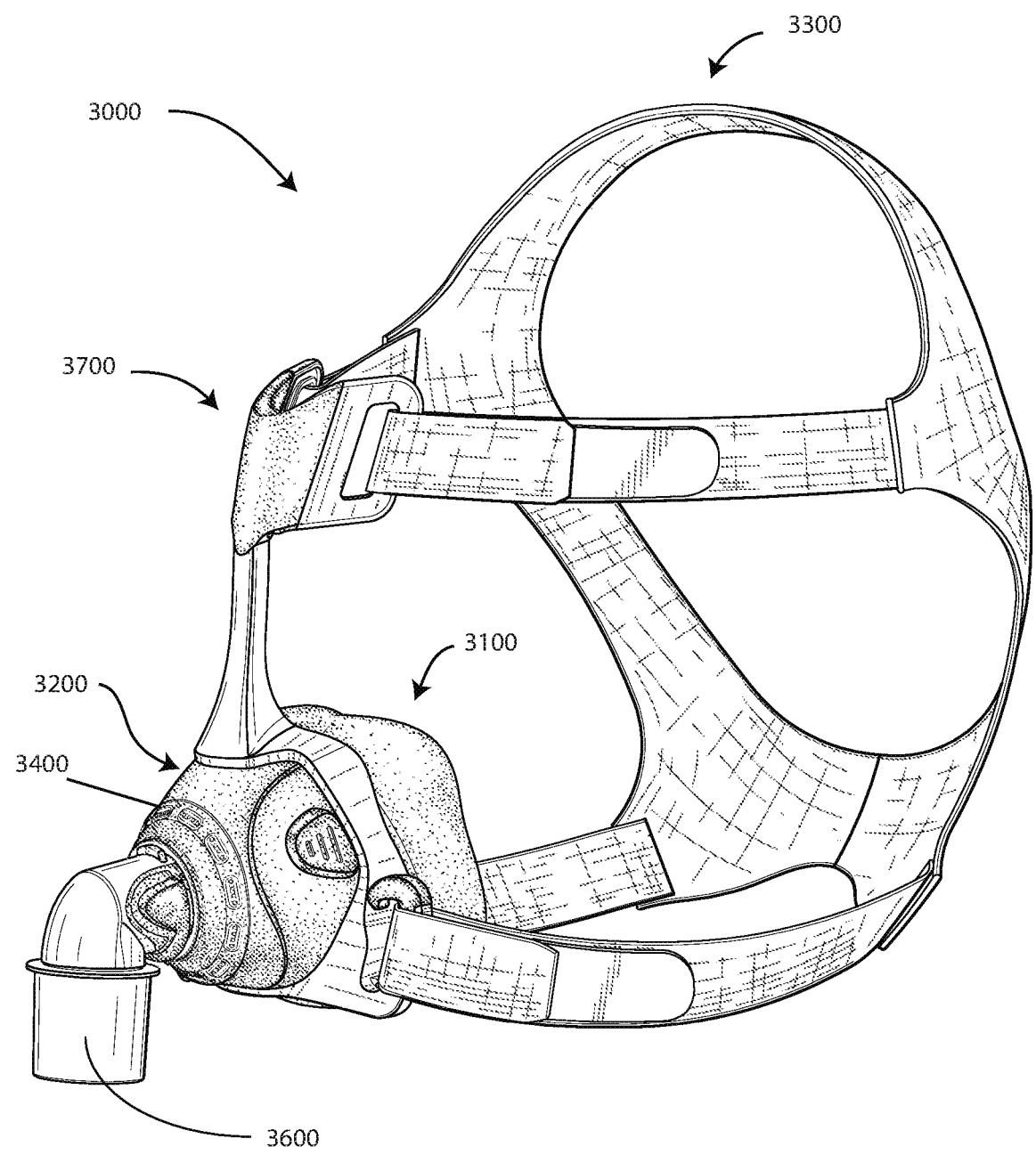

FIG. 3A shows a patient interface in the form of a nasal mask in accordance with one form of the present technology.

Figure 3B:
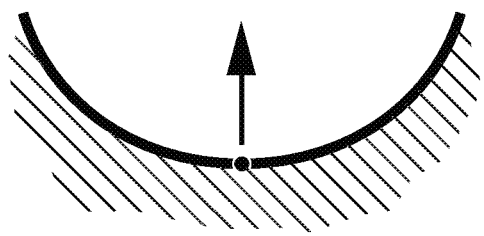

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
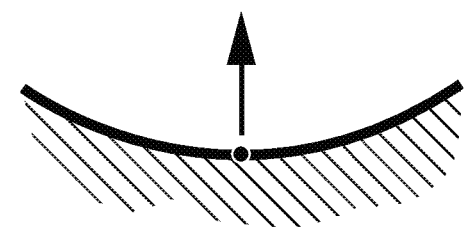

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
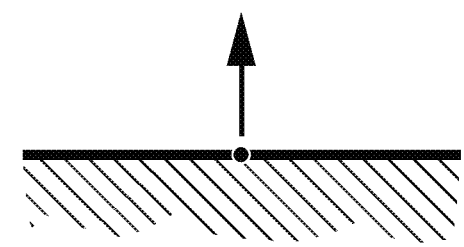

FIG. 3D shows a schematic of a cross-section through a structure at a point. An outward normal at the point is indicated. The curvature at the point has a value of zero.

Figure 3E:
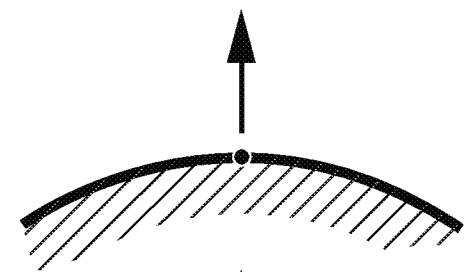

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
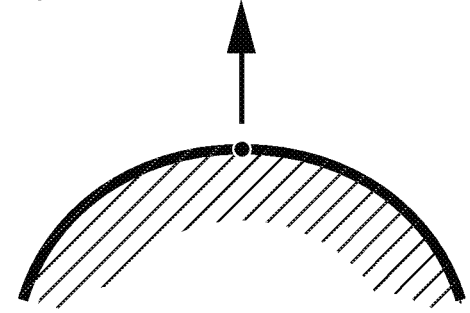

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
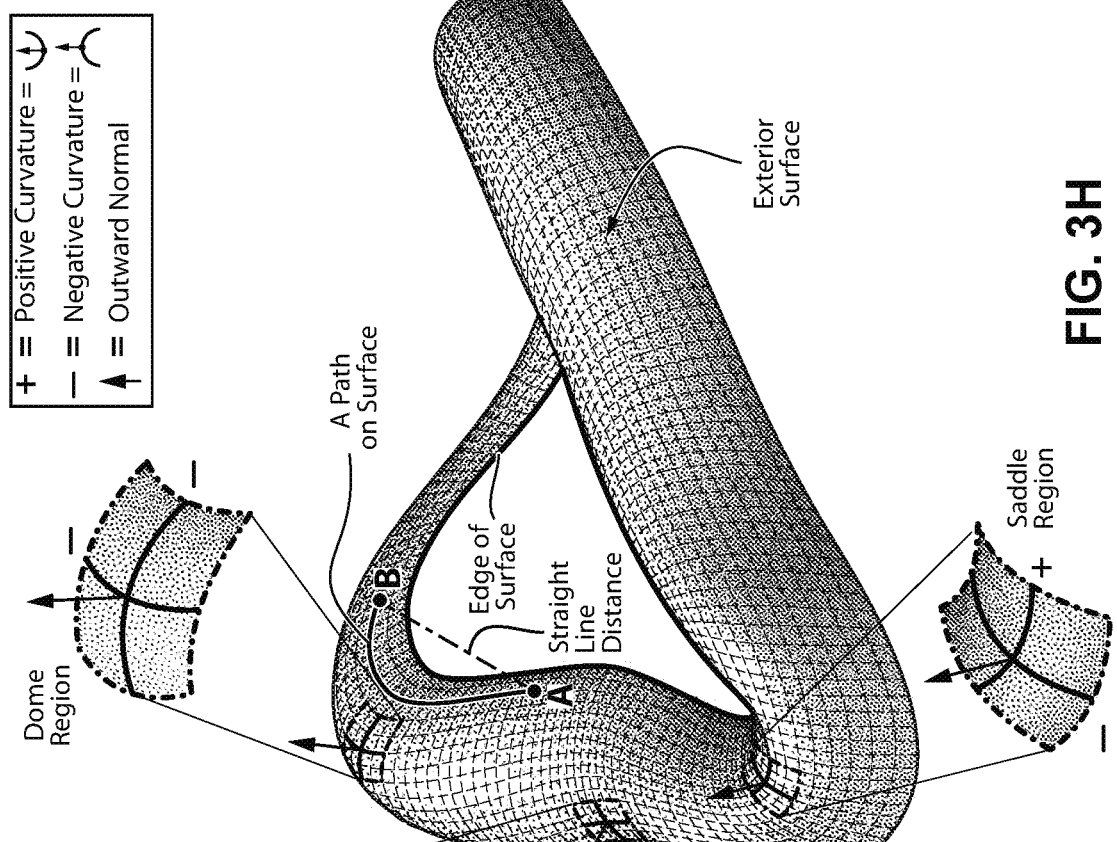
Figure 3G:
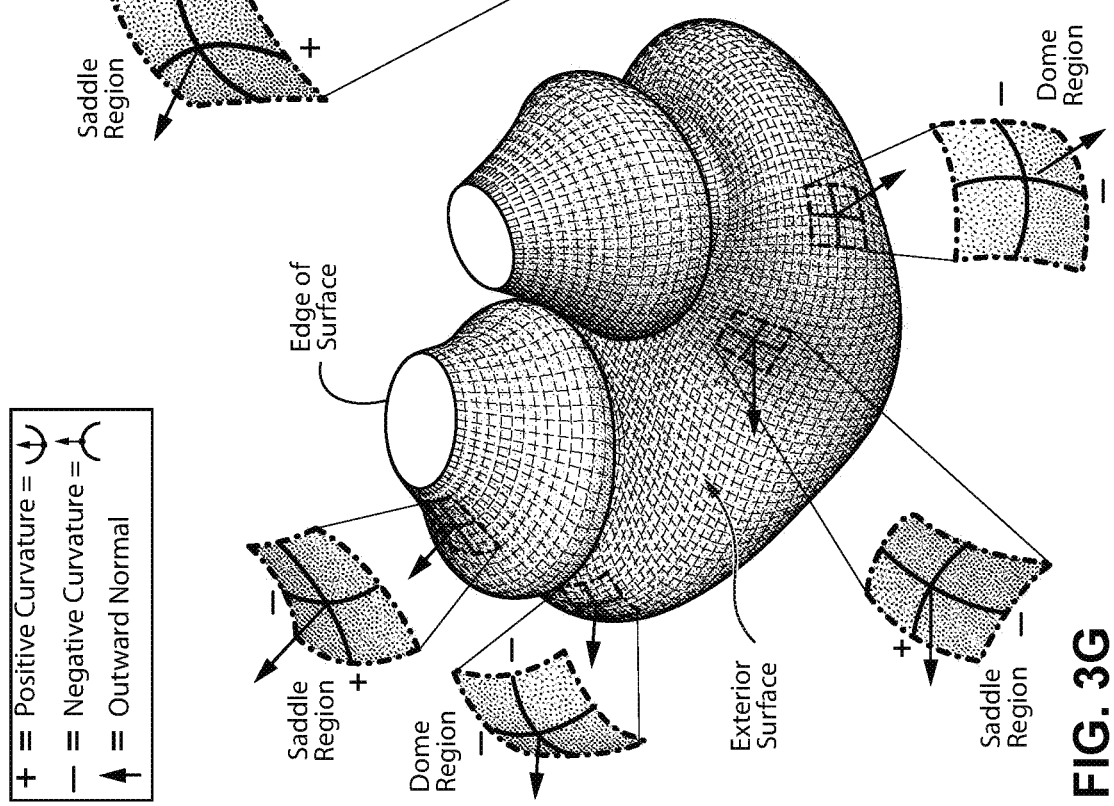

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
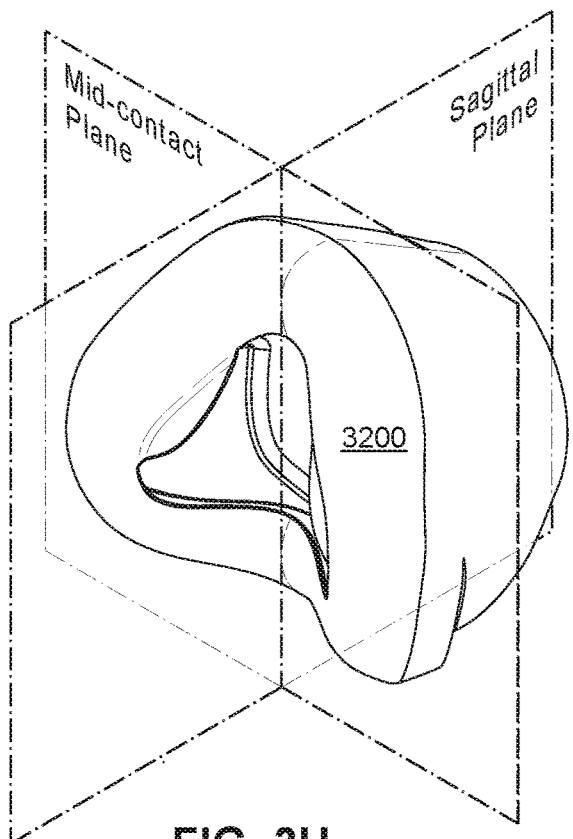

FIG. 3U shows a view of a plenum chamber 3200 showing a sagittal plane and a mid-contact plane.

Figure 3V:
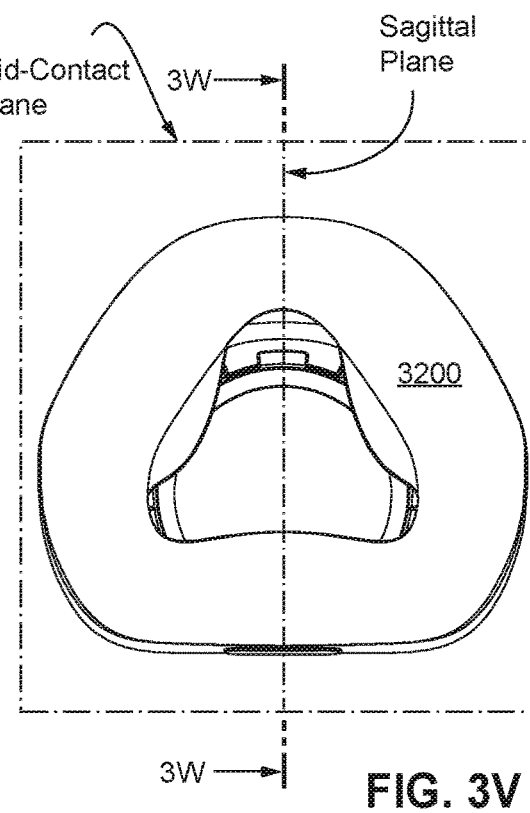

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
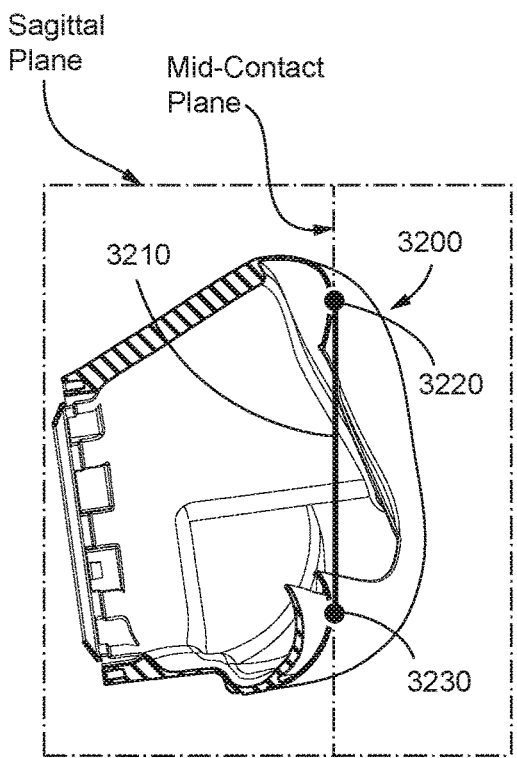

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
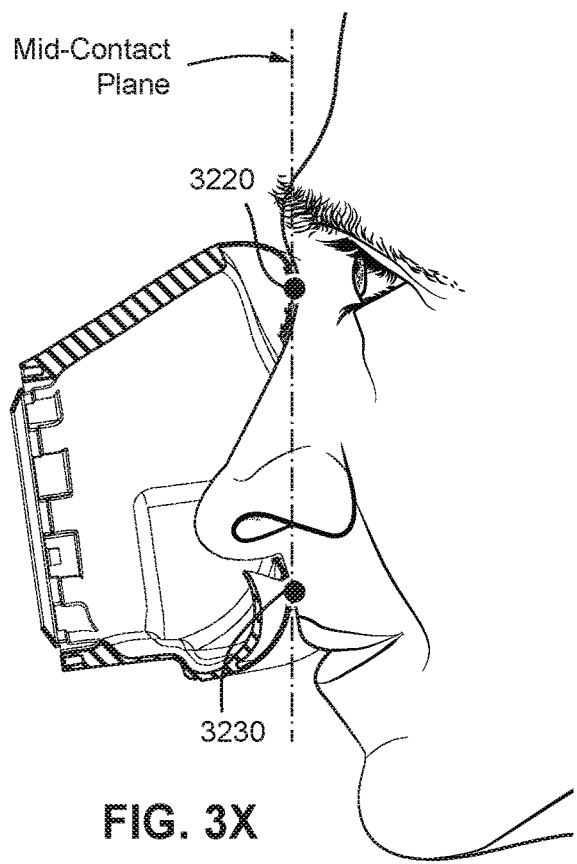

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
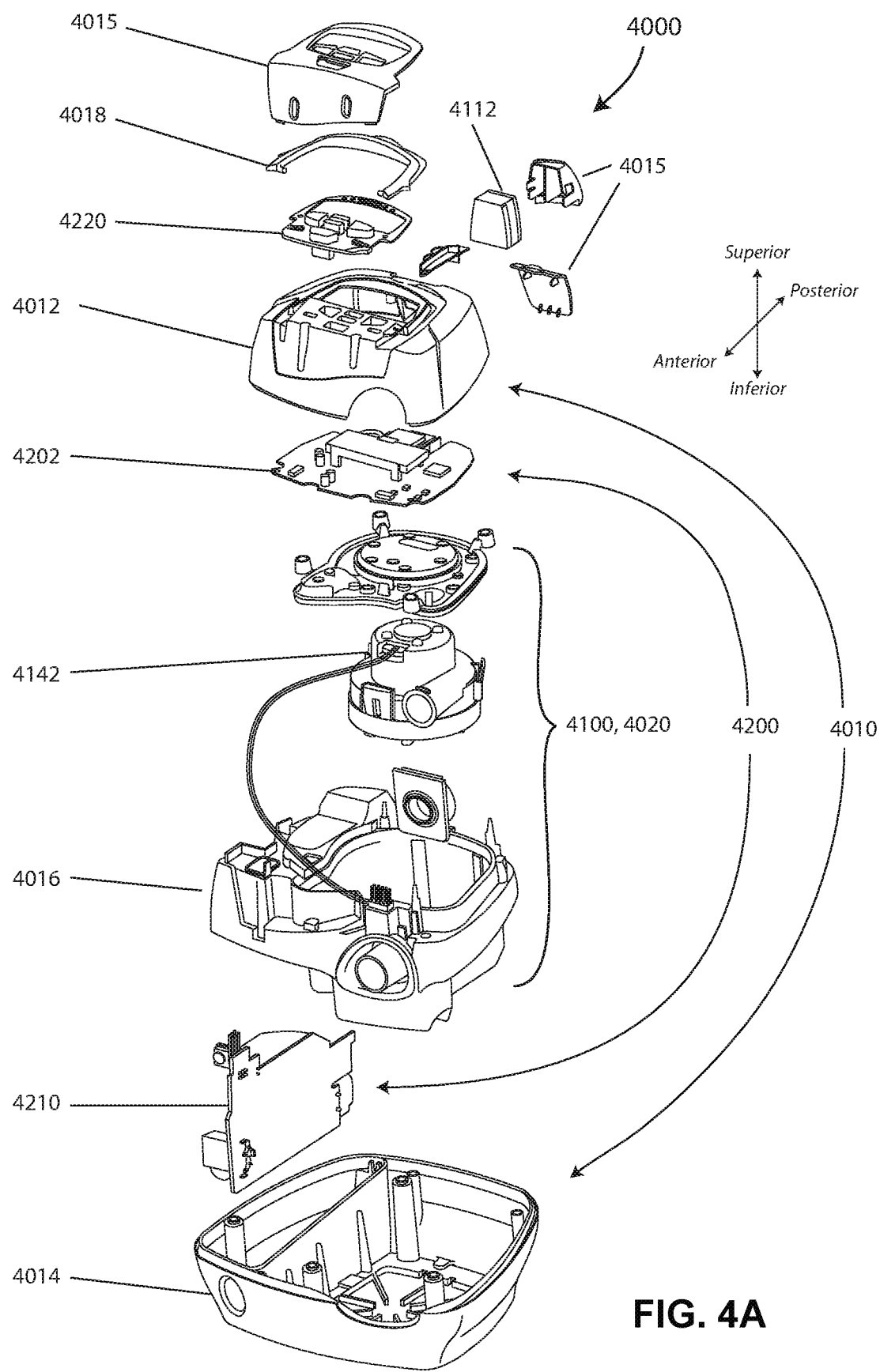

FIG. 4A shows an RPT device in accordance with one form of the present technology.

Figure 4B:
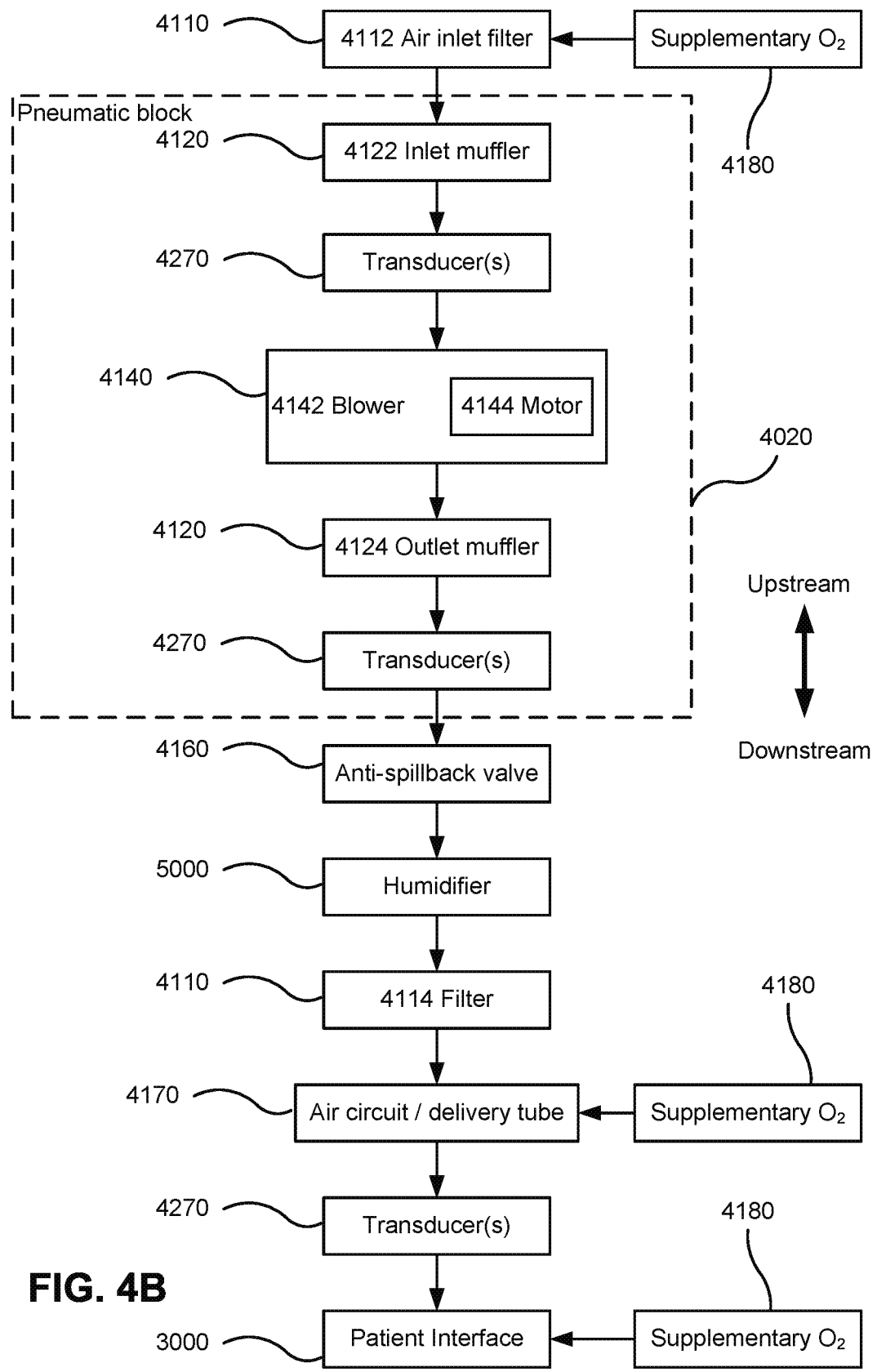

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
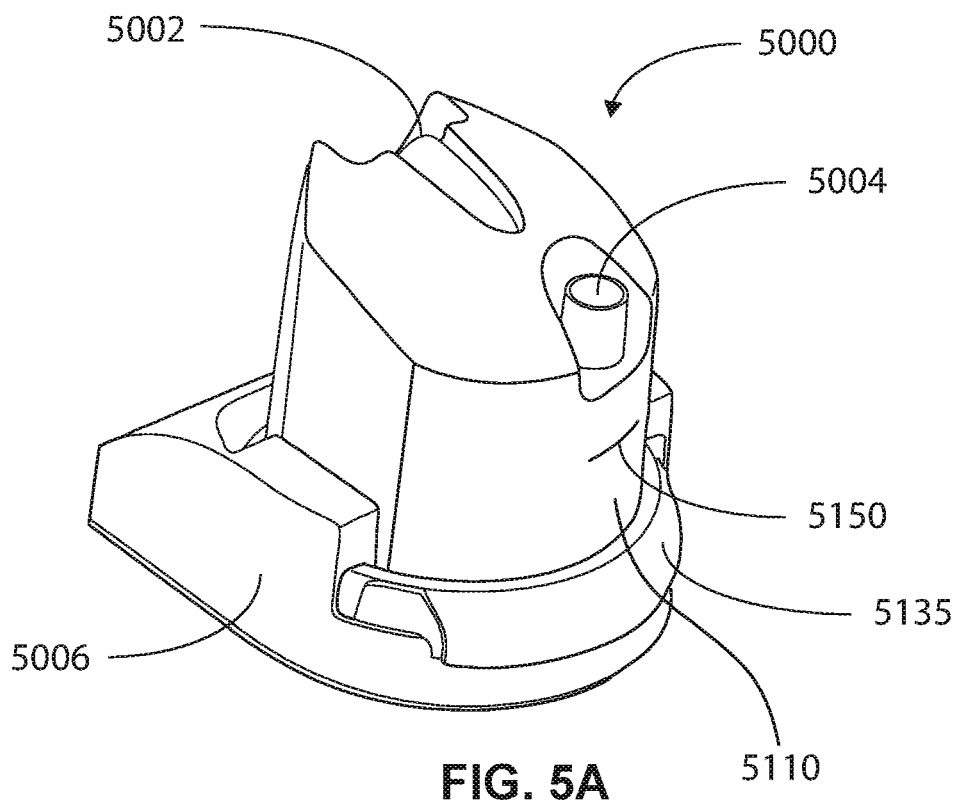

FIG. 5A shows an isometric view of a humidifier in accordance with one form of the present technology.

Figure 5B:
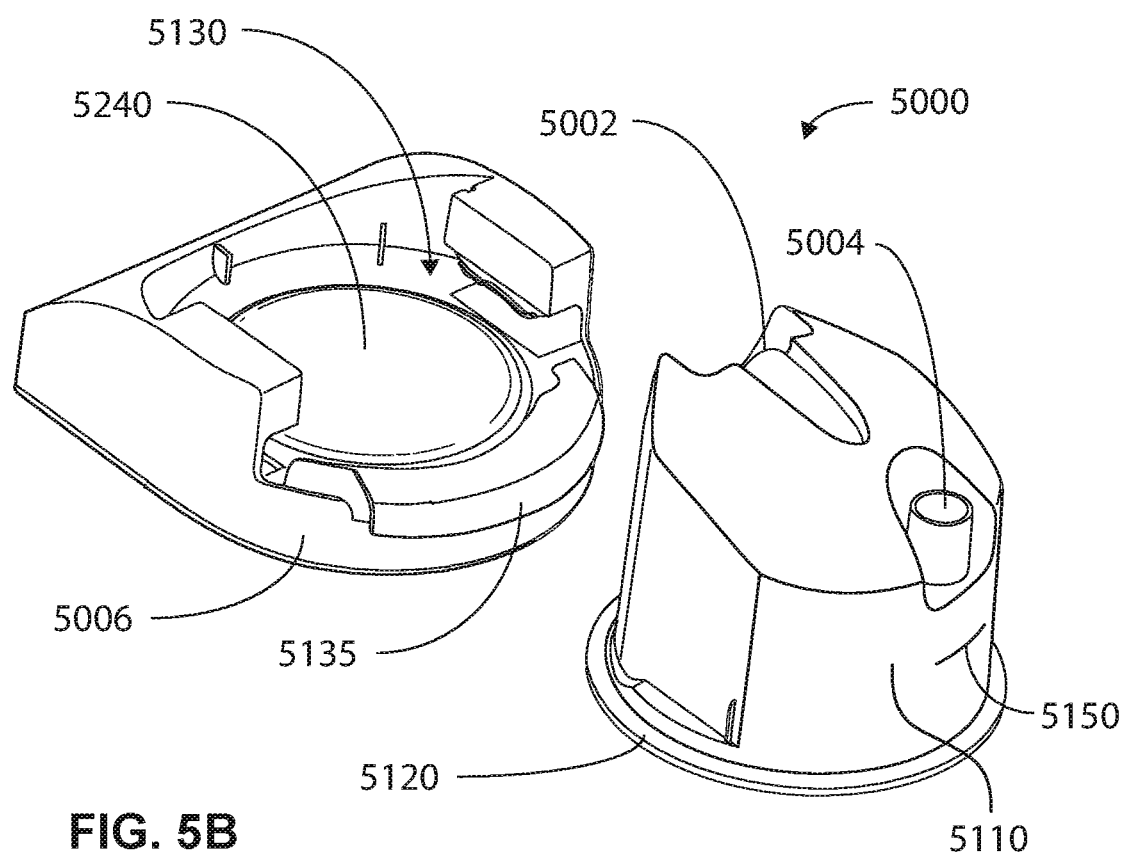

FIG. 5B shows an isometric view of a humidifier in accordance with one form of the present technology, showing a humidifier reservoir 5110 removed from the humidifier reservoir dock 5130.

4.6 Breathing Waveforms

Figure 6:
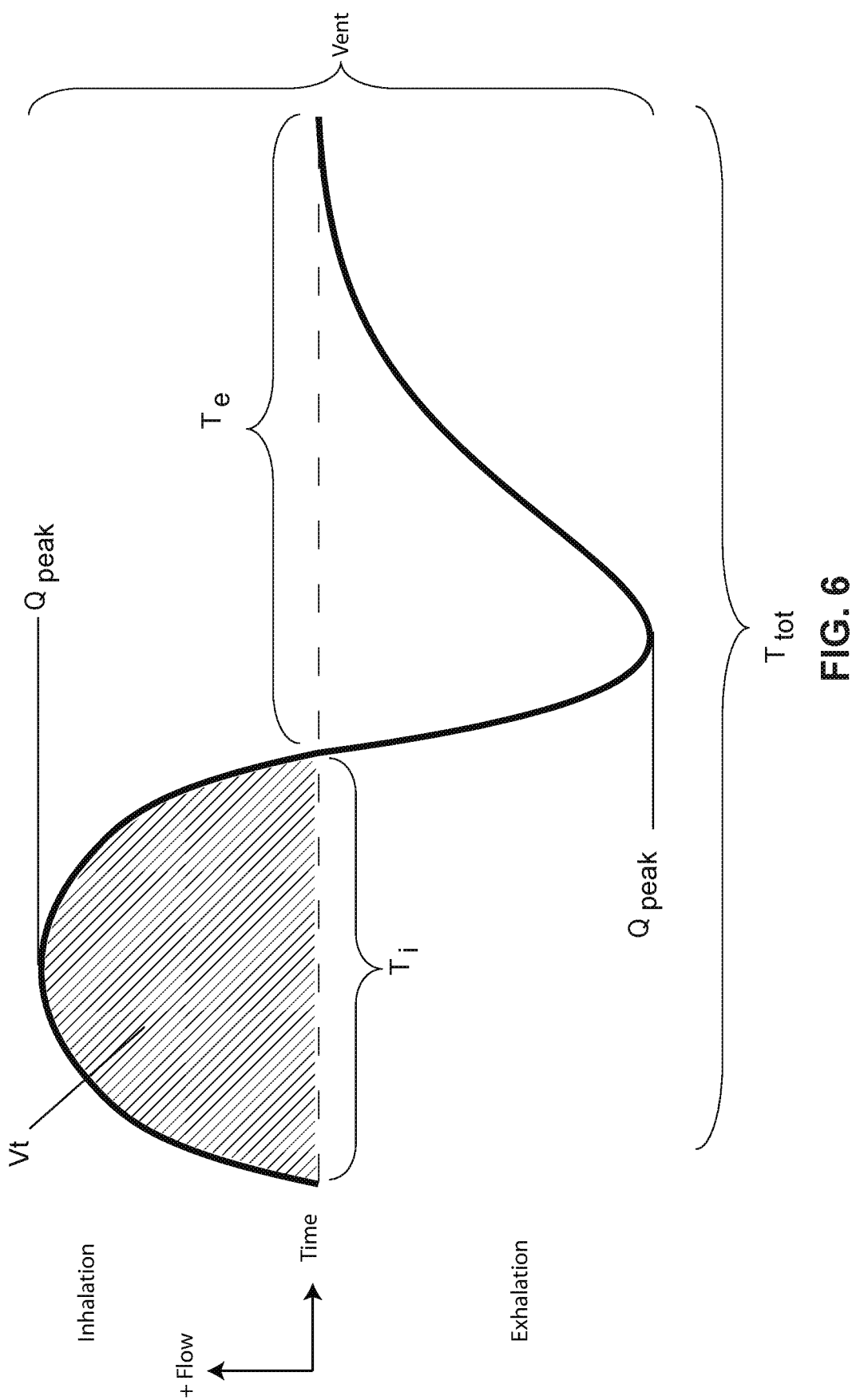

FIG. 6 shows a model typical breath waveform of a person while sleeping.

4.7 Particular Examples of the Present Technology

Figure 7:
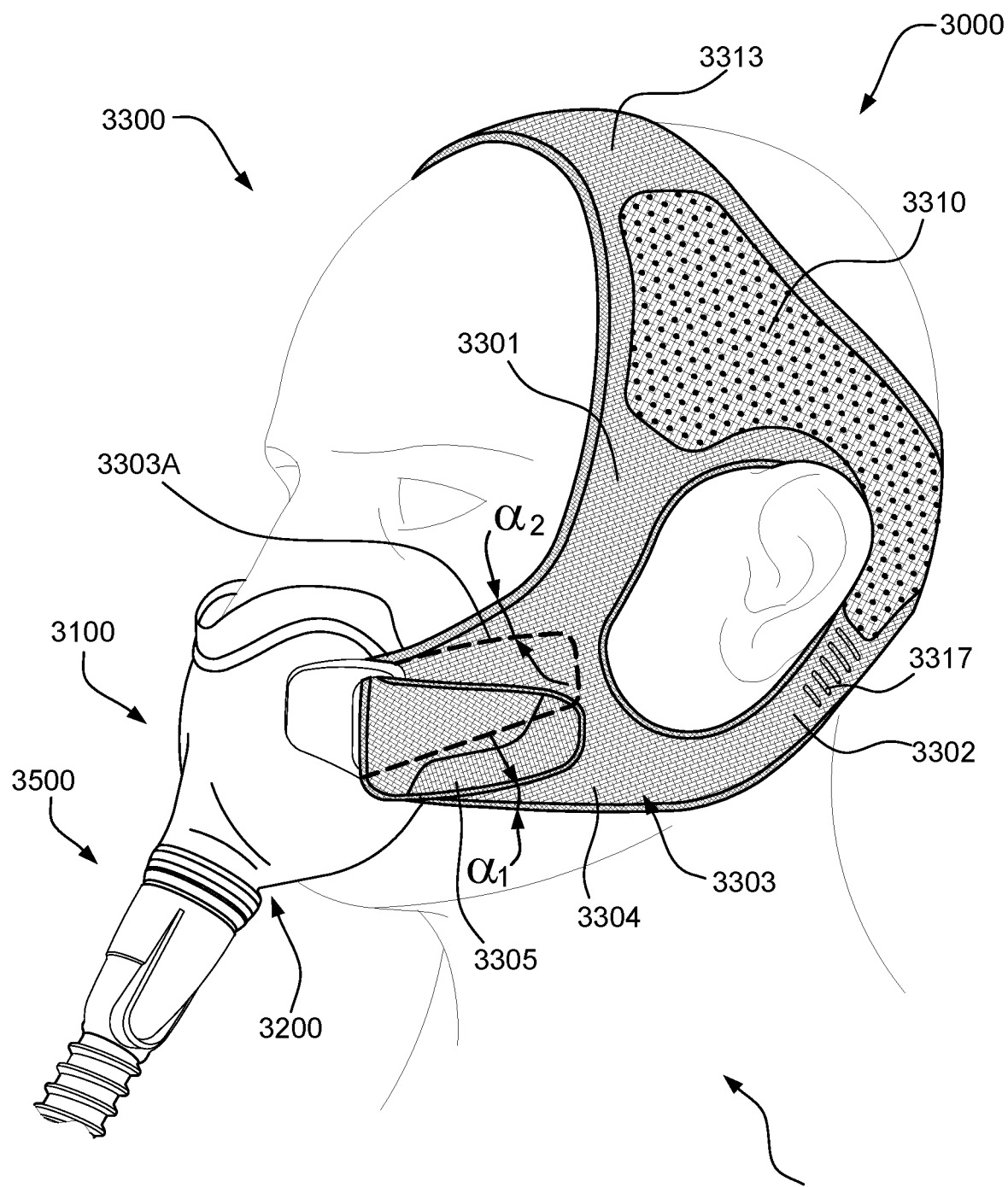

FIG. 7 shows a side perspective view of a patient wearing a patient interface according to one example of the present technology, with an engagement of the anterior strap attachment portion and the strap receiving portion at a second possible angular position shown in dashed lines.

Figure 8:
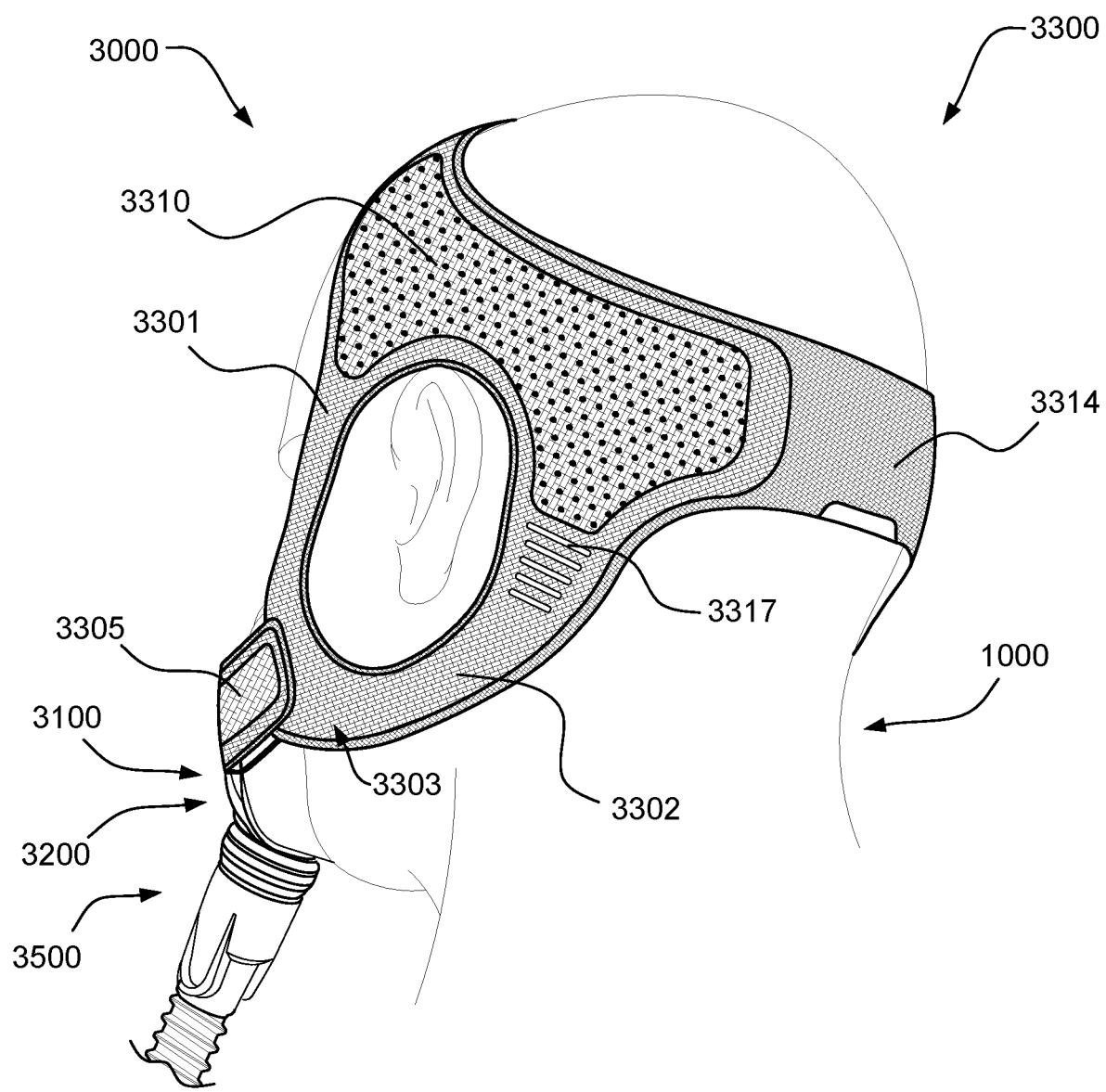

FIG. 8 shows a back perspective view of the patient interface of FIG. 7.

Figure 9:
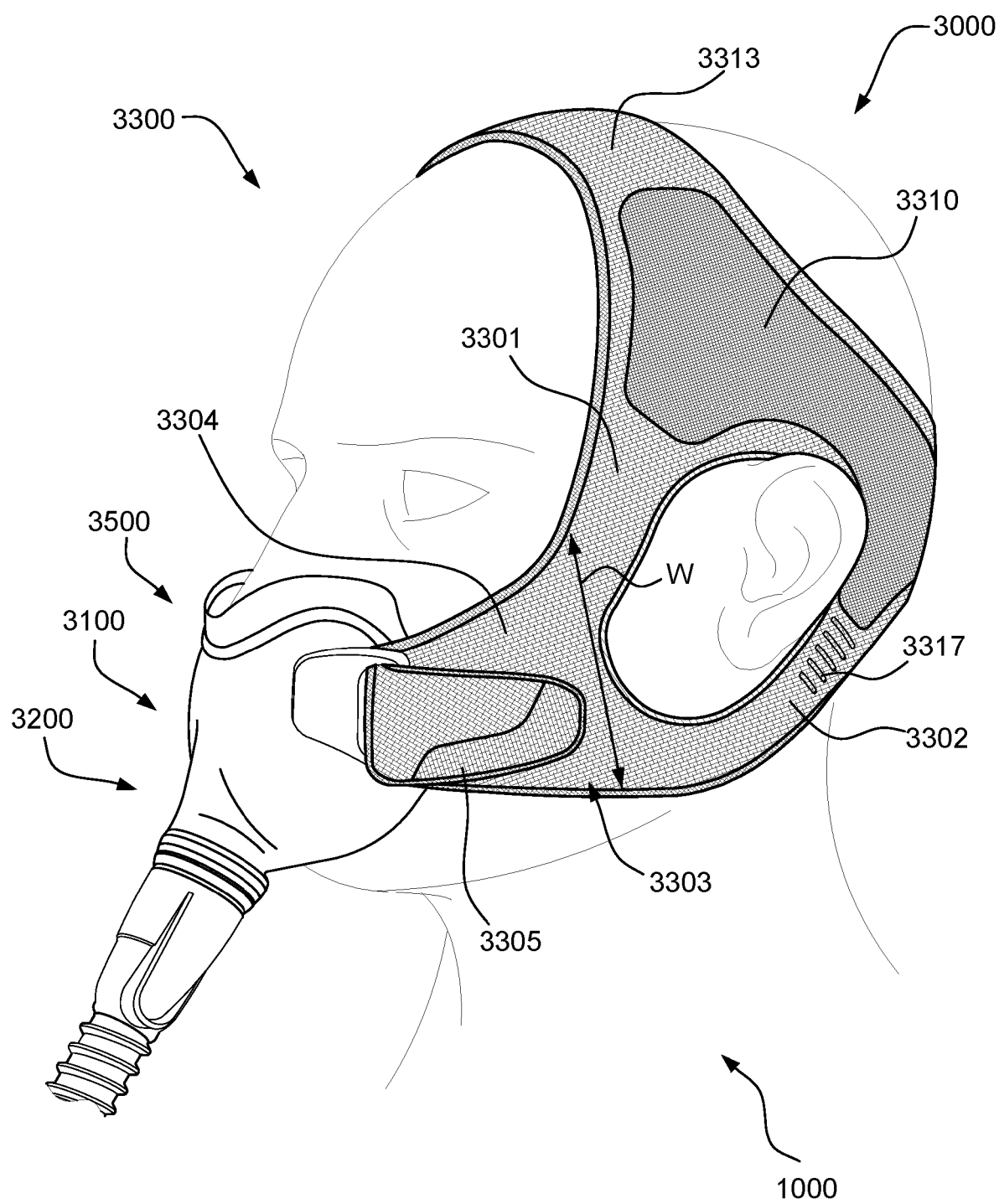

FIG. 9 shows a side perspective view of a patient wearing the patient interface according to another example of the present technology.

Figure 10:
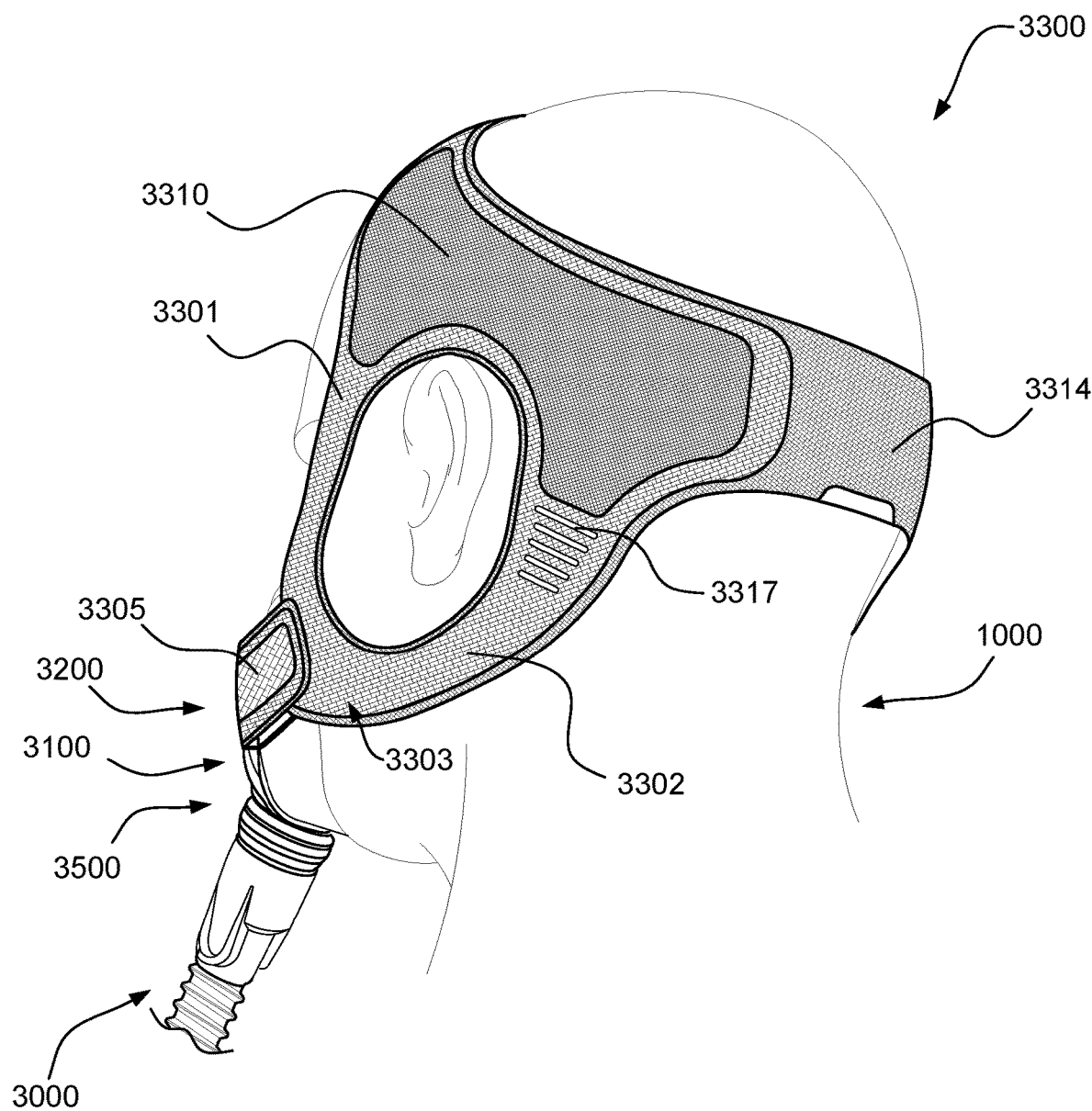

FIG. 10 shows a back perspective view of the patient interface of FIG. 9.

Figure 11:
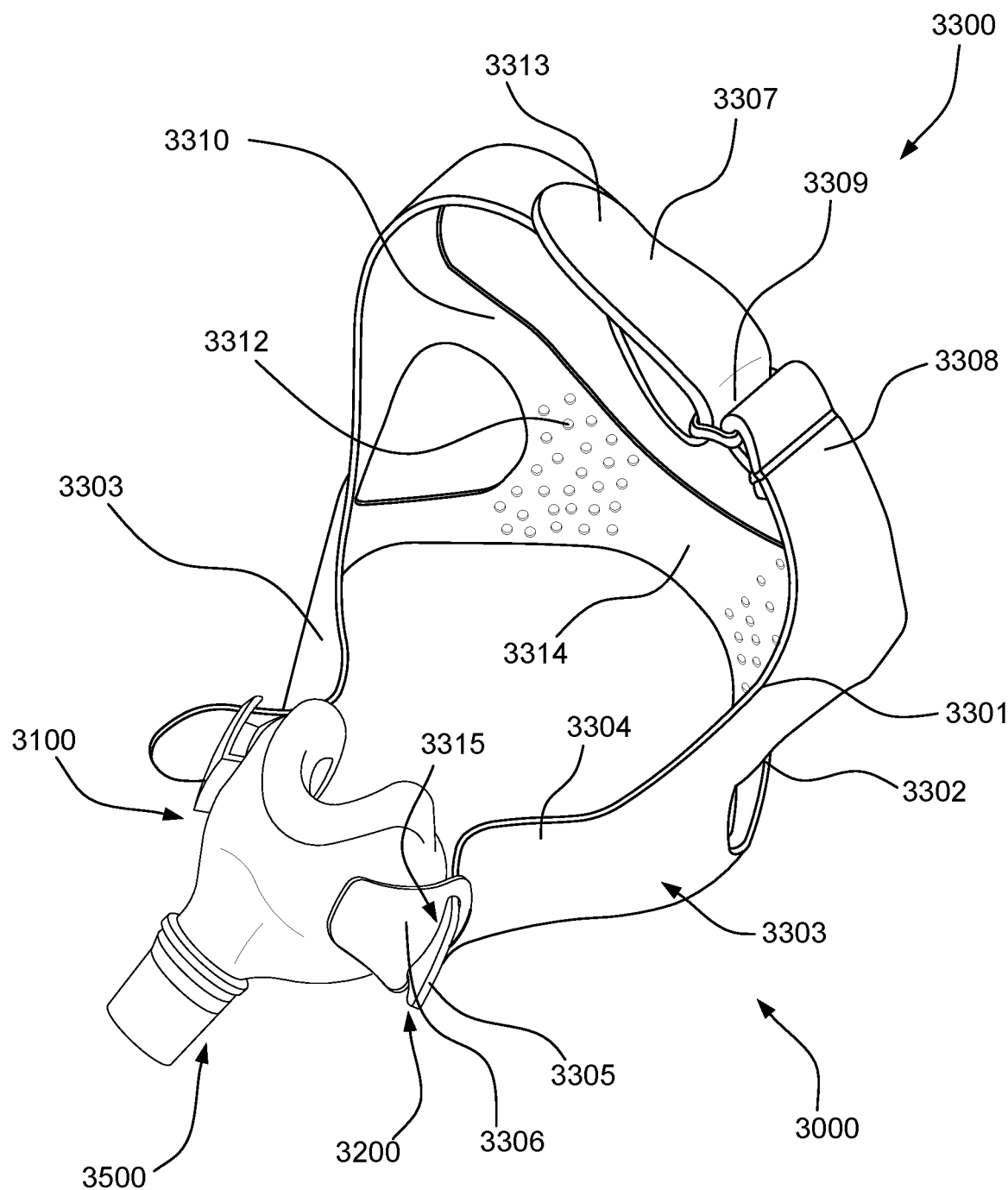

FIG. 11 shows a top perspective view of a patient interface according to another example of the present technology.

Figure 12:
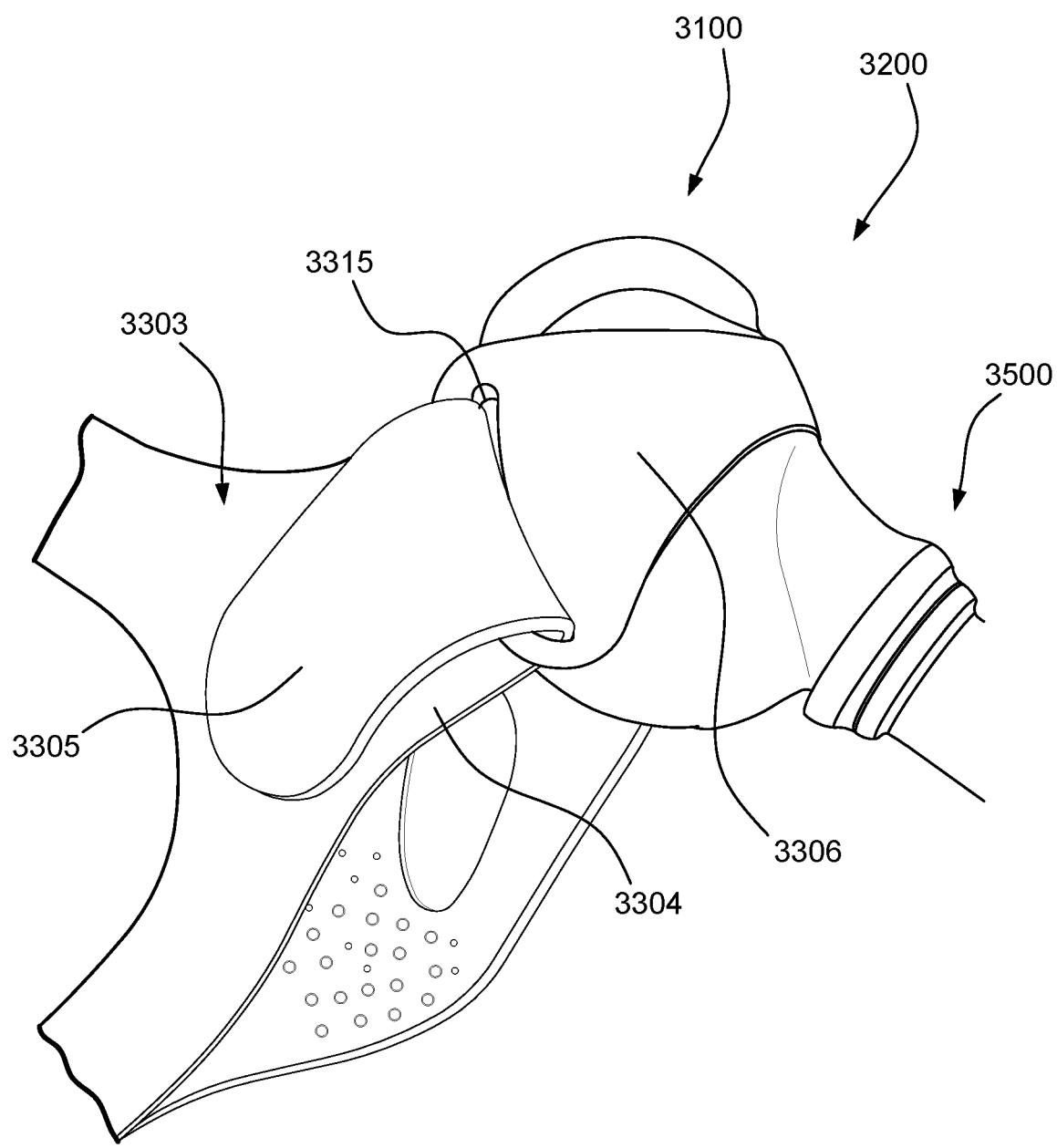

FIG. 12 shows an enlarged right hand side perspective view of a patient interface with a connecting portion according to another example of the present technology connected to the positioning and stabilising structure of FIG. 11.

Figure 13:
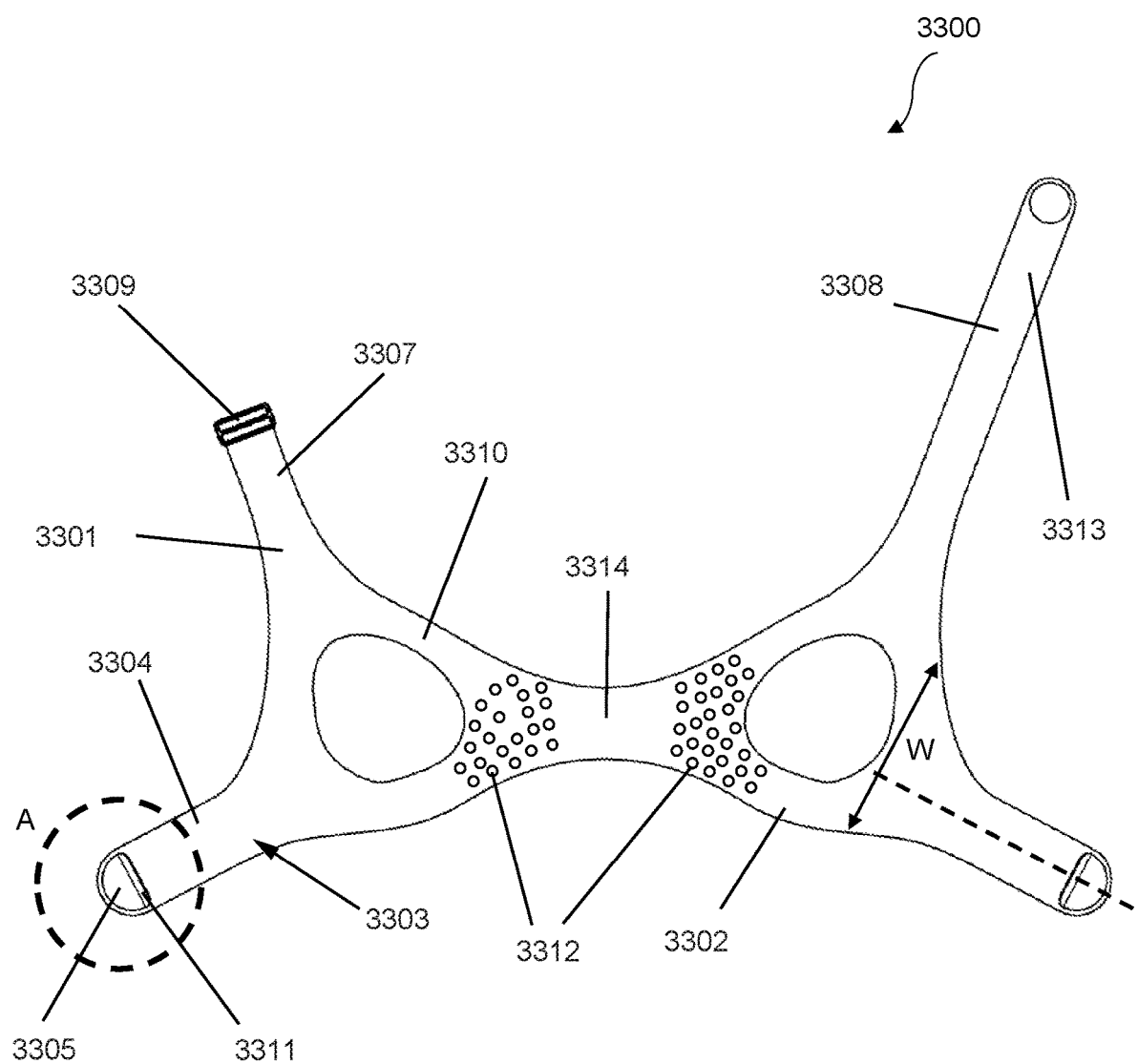

FIG. 13 shows a back view of the positioning and stabilising structure of FIG. 11 in a flattened configuration.

Figures 1, 13:
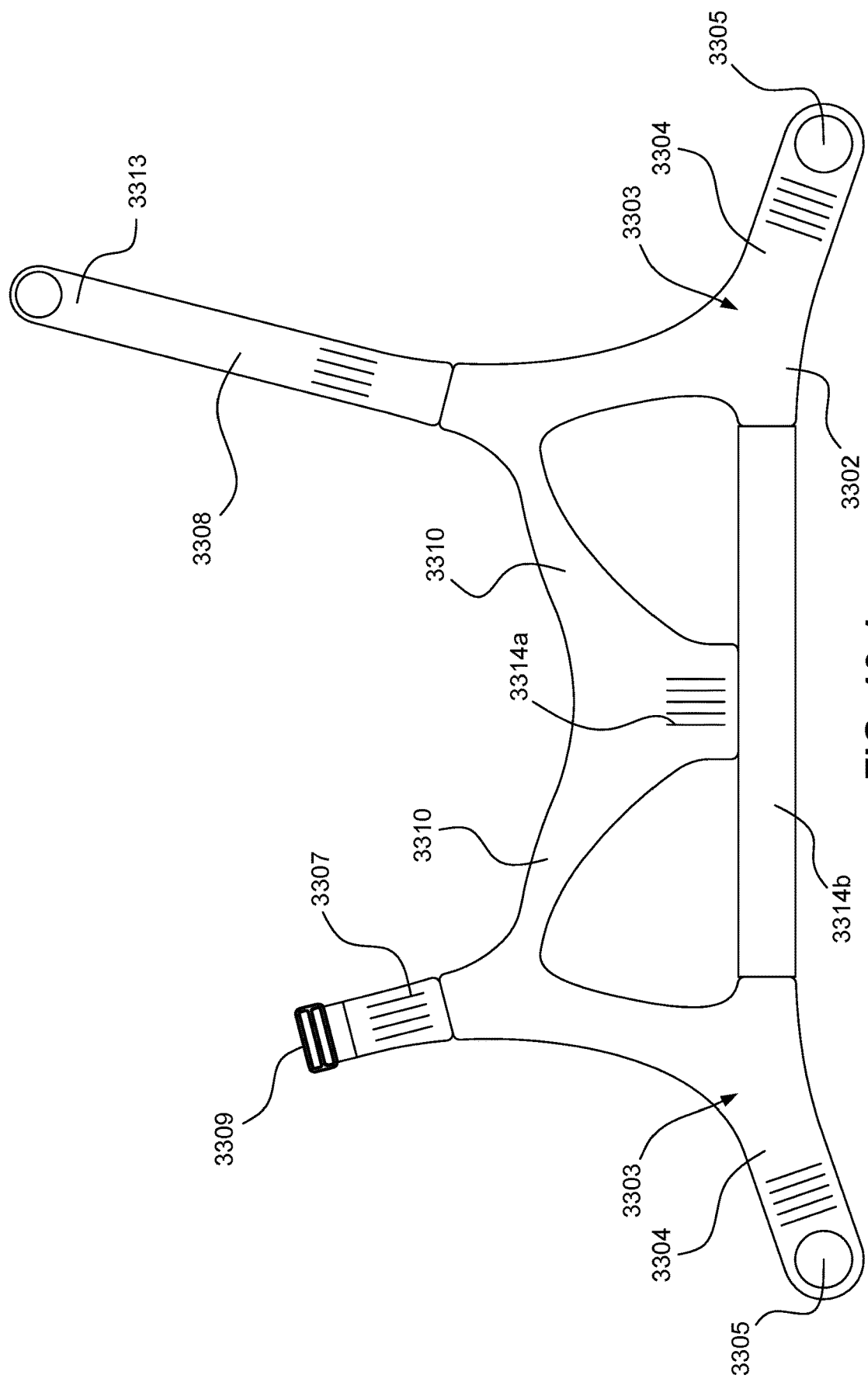

FIG. 13-1 shows a back view of the positioning and stabilizing structure of a flattened patient interface according to another configuration.

Figure 14:
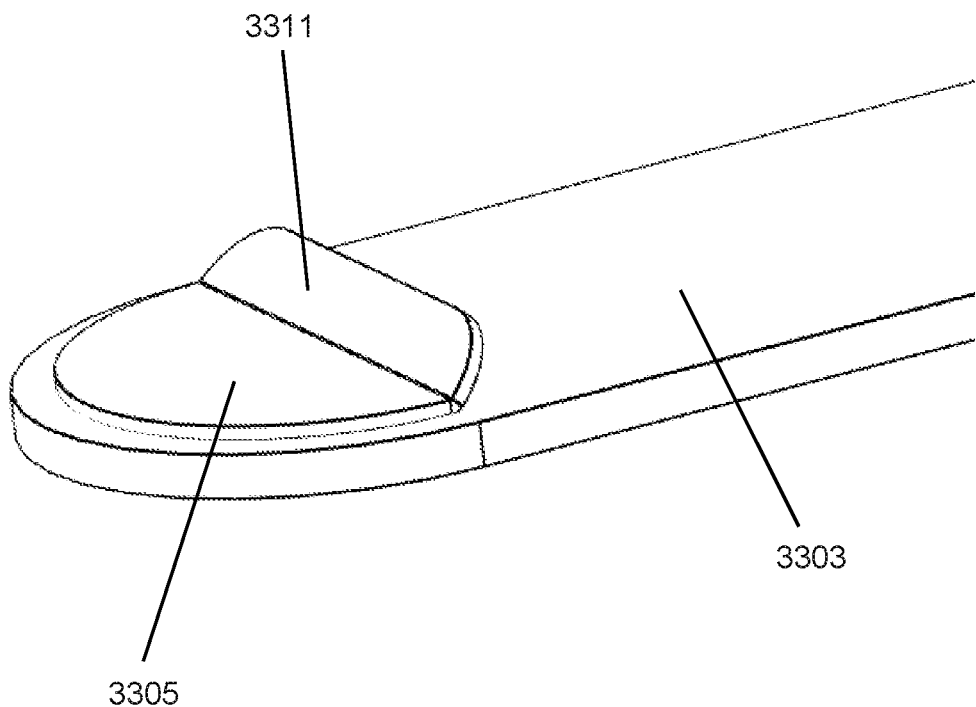

FIG. 14 shows an enlarged perspective view of region A of FIG. 13 from one side and below.

Figure 15:
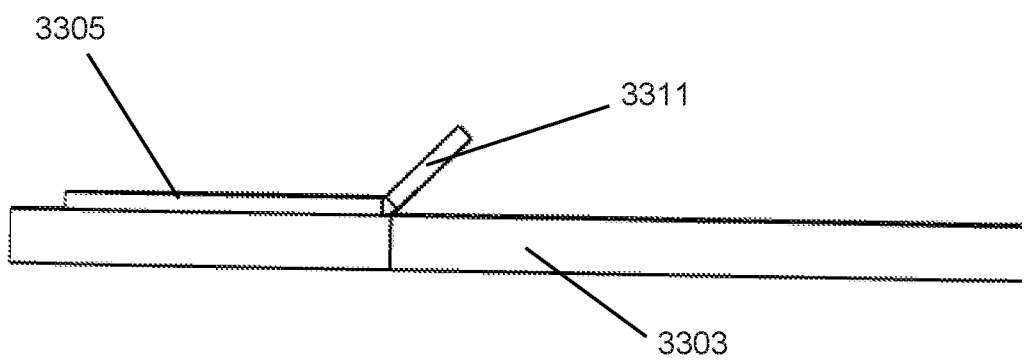

FIG. 15 shows an enlarged bottom view of region A of FIG. 13.

Figure 16:
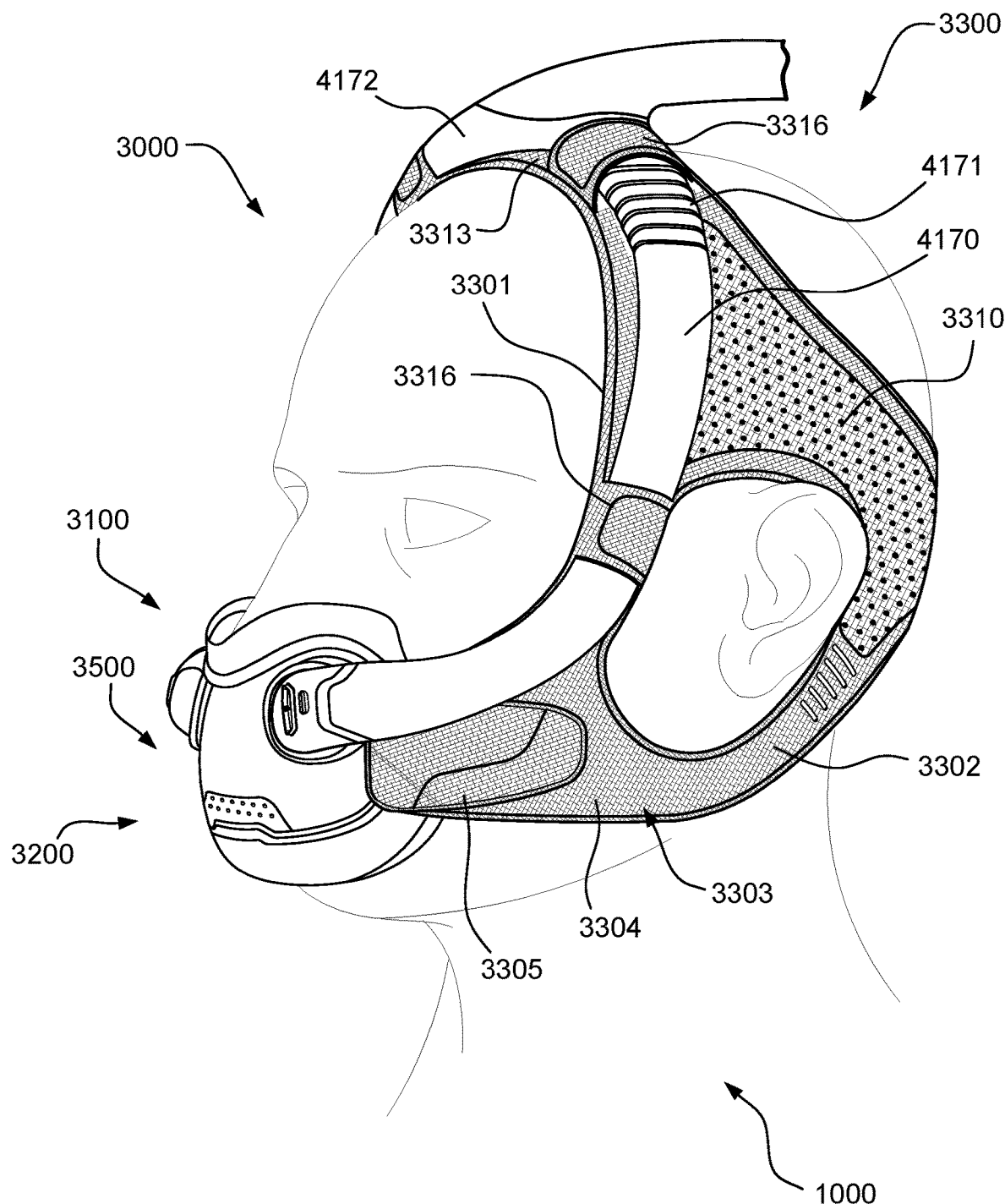

FIG. 16 shows a side perspective view of a patient wearing a patient interface according to one example of the present technology.

Figure 17:
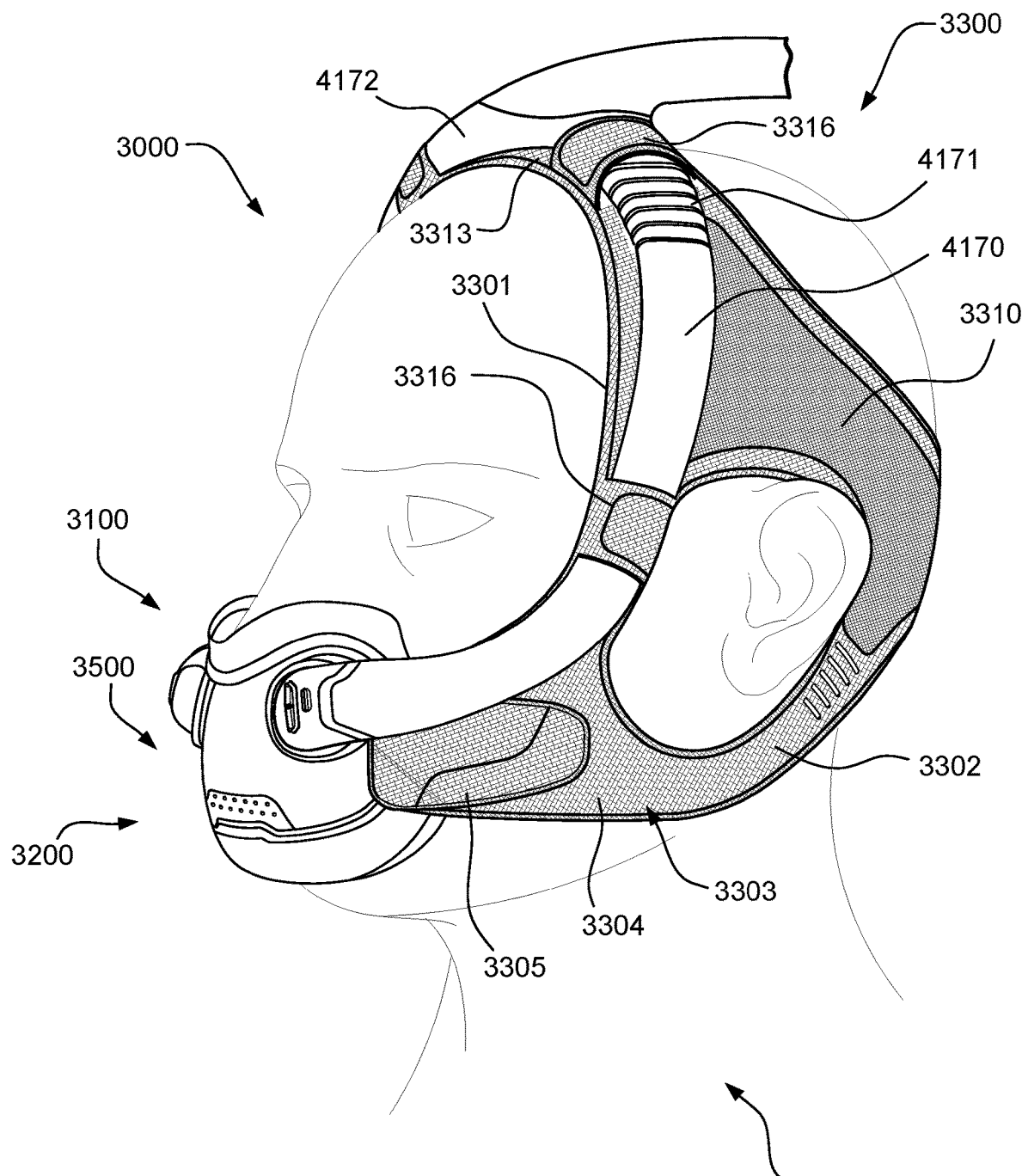

FIG. 17 shows a side perspective view of a patient wearing a patient interface according to one example of the present technology.

Figure 18:
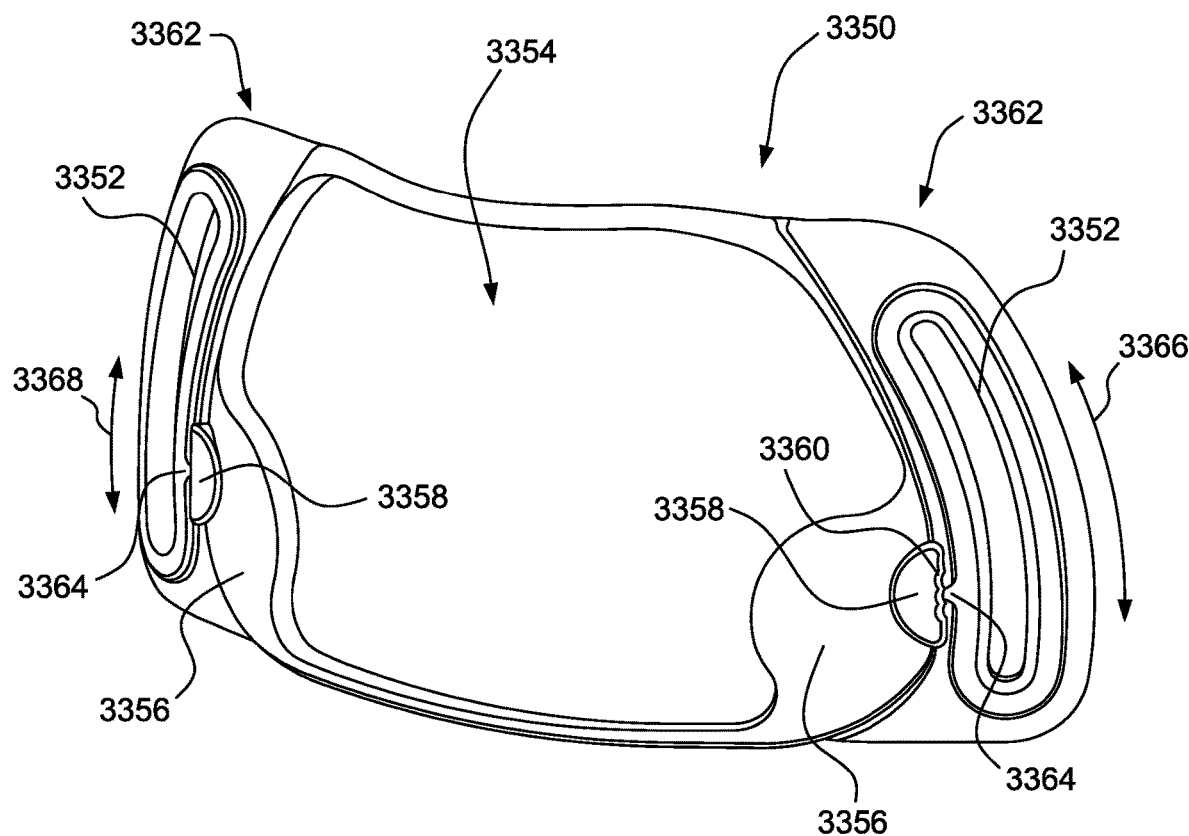

FIG. 18 shows a perspective view of a frame for use with one example of the present technology.

Figure 19:
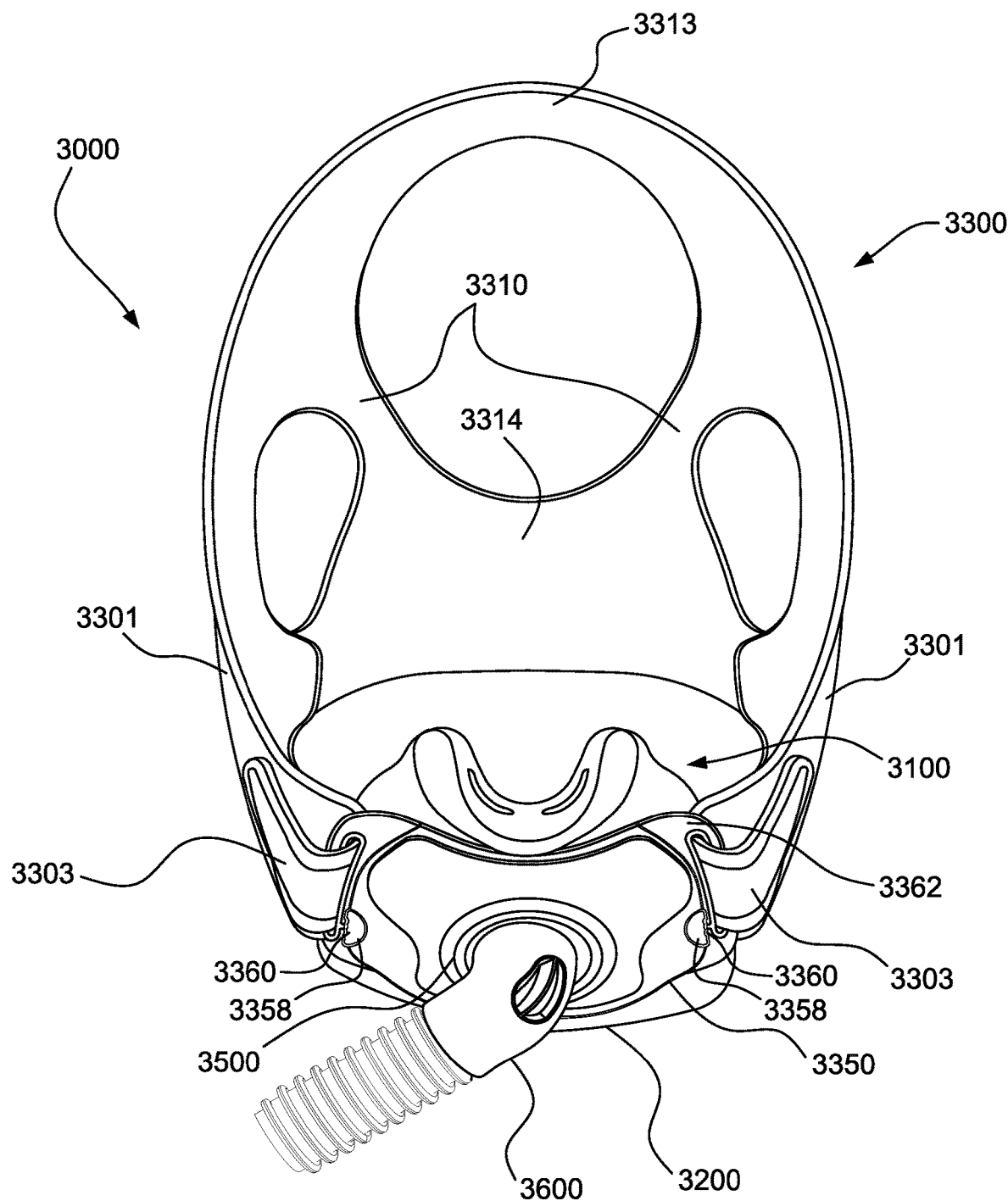

FIG. 19 shows a perspective view of a patient interface according to one example of the present technology, with the frame of FIG. 18.

Figure 20:
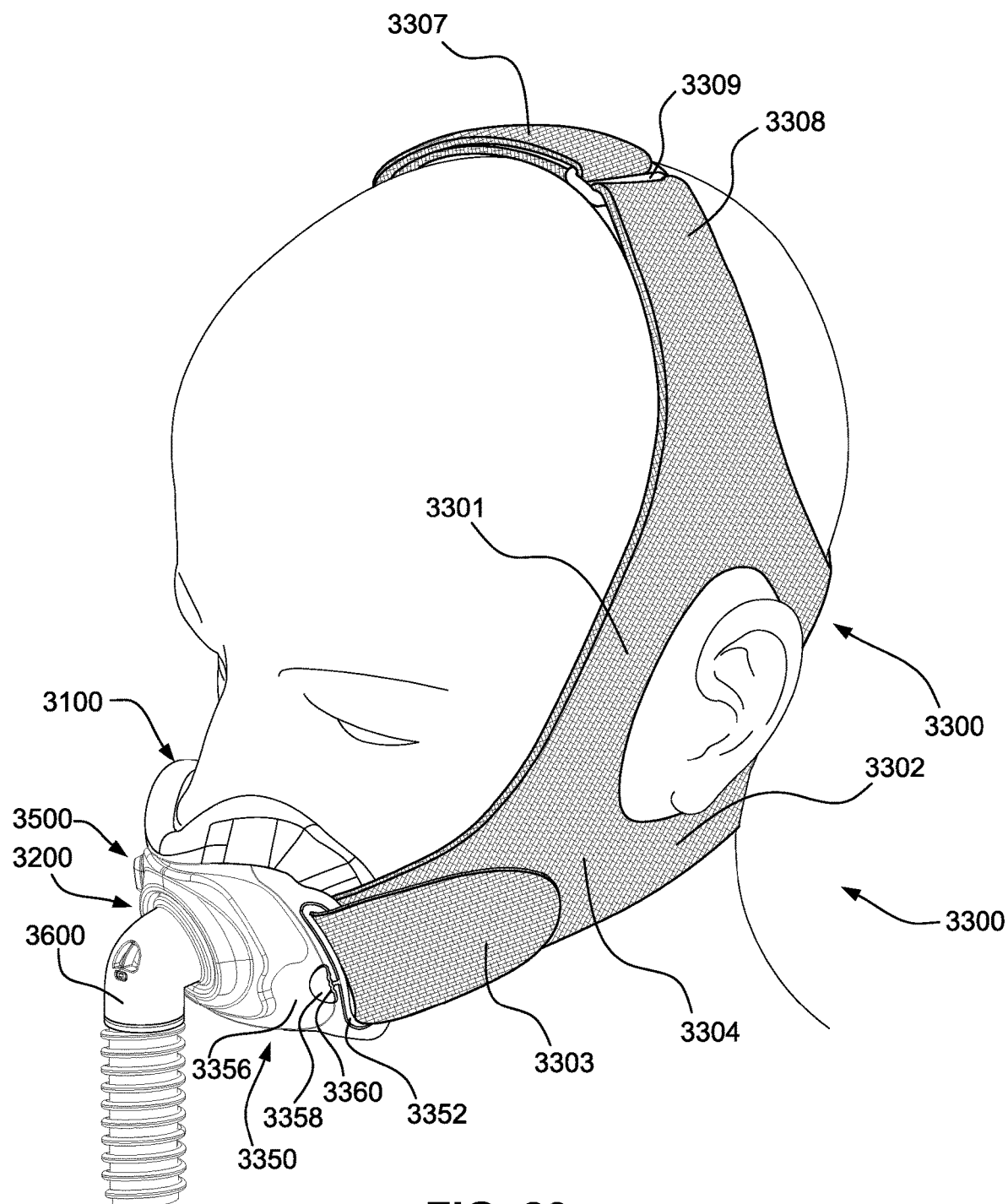

FIG. 20 shows a perspective view of the patient interface of FIG. 19 that is worn by a patient.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. A flow of pressurized air can flow into the plenum chamber 3200 in order to pressurize it to a therapeutic pressure (e.g., 6 cmH2O above ambient air pressure). In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material. The seal-forming structure 3100 can create a seal with the patient's face in order to maintain the therapeutic pressure within the plenum chamber 3200, and limit leaks of the pressurized air to the ambient.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material.

The use of a translucent material can reduce the obtrusiveness of the patient interface, and help improve compliance with therapy.

In certain forms of the present technology, the plenum chamber 3200 comprises a cushion module. The cushion module comprising a shell. In some examples of the technology the cushion module is directly connectable to a headgear connection portion as described herein. An advantage of having the headgear connection integrated directly into the cushion module is a reduction in parts, as a separate frame component to connect the headgear with the plenum chamber is no longer necessary. This may make the patient interface easier to use, easier to clean and/or less costly to manufacture.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with their head on a pillow.

In one form of the present technology, a positioning and stabilising structure 3300 is provided that is configured so as not to be too large and bulky to prevent the patient from lying in a side sleeping position with their head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.3.1 Two-Point Connection Headgear

In one example of the present technology, the positioning and stabilising structure 3300 comprises a headgear formed of multiple headgear strap portions. FIGS. 7 and 8 show the headgear according to one example of the present technology. FIGS. 9 and 10, and 11 to 15 show slightly modified embodiments of the headgear of FIGS. 7 and 8.

The headgear comprises at least one superior strap portion 3301. The superior strap portion 3301 may be configured to overlie the cheek region of the patient's face, preferably the upper cheek region, and extends between the top of the patient's ear and the patient's eye. The headgear further comprises at least one inferior strap portion 3302. The inferior strap portion 3302 may overlie a region of the patient's head below and behind the patient's ear. The superior strap portion 3301 and the inferior strap portion 3302 are connected to an anterior strap portion 3303. The superior strap portion 3301 and the inferior strap portion 3302 join the anterior strap portion 3303 anterior to the patient's ear, in use. In the embodiment shown the headgear comprises two superior strap portions 3301, two inferior strap portions 3302, and two anterior strap portions 3303, one of each located on each of the left and right hand sides of the patient's skull. The two anterior strap portions 3303 may each be formed integrally with one end of the superior strap portion 3301 and one end of the inferior strap portion 3302. In the embodiments shown the two superior strap portions 3301 attach to a crown strap portion 3313 and the two inferior strap portions 3302 attach to a back strap portion 3314.

Each anterior strap portion 3303 is connected or connectable to a connection portion 3306 (shown in FIGS. 11 and 12) which engages an interfacing portion 3500 of the patient interface 3000. In the embodiment shown in FIGS. 7 to 12 the interfacing portion 3500 comprises an ultra-compact full-face mask, which is configured to seal with the mouth and the nose of the patient. The ultra-compact full-face mask seals under the nose to the nares of the patient. In other embodiments the interfacing portion 3500 may comprise a full-face mask or other mask configured to create a seal with the patient's airways and provide a flow of air. The seal-forming structure of the full-face mask forms a seal with the nasal bridge of the patient.

In one example, the anterior strap portion 3303 comprises a strap receiving portion 3304 and a strap attachment portion 3305 (as best seen in FIGS. 13 and 13-1). The strap attachment portion 3305 is releasably connectable to the strap receiving portion 3304 such that the anterior strap portion 3303 forms a loop. The loop engages the connection portion 3306 which engages the interfacing portion 3500. In some forms of the technology the connection portion 3306 forms part of the interfacing portion 3500 (as shown in FIGS. 11 and 12).

The strap receiving portion 3304 is configured to engage the strap attachment portion 3305 in a selected one of a plurality of possible positions. Each one of the plurality of possible positions is entirely on the strap receiving portion. In other words, the strap attachment portion 3305 is entirely within a boundary of the strap receiving portion 3304 while engaged to the strap attachment portion 3305. The strap attachment portion 3305 is sufficiently wide to allow for a wide range of adjustments, and also limit contact between the strap attachment portion 3305 and the patient's skin (e.g., the patient's cheek). The strap attachment portion 3305 may have a rough and/or abrasive surface and the width of the strap receiving portion may allow for multiple adjustment positions without the strap attachment portion 3305 extending outside of the boundary of the strap receiving portion 3304. The plurality of possible positions comprises a plurality of possible angular positions of the strap attachment portion 3305 relative to the strap receiving portion 3304 (e.g., as described in AU 2019902272, which is incorporated by reference herein in its entirety). As shown in FIG. 7, engaging the strap attachment portion 3305 in one of the plurality of angular positions forms an angle $\alpha_1$ between a first and second part of a bottom edge of the anterior strap portion loop. The possible positions can vary from each other in both the superior-inferior and the anterior-posterior directions. For example, a bottom edge of the strap attachment portion 3305 may be displaced from a bottom edge of the strap receiving portion 3304 so that the two bottom edges are not collinear. In any of the plurality of angular positions, bottom edge of the strap attachment portion 3305 remains more superior than the bottom edge of the strap receiving portion 3304. Dashed lines 3303A of FIG. 7 show the anterior strap attachment portion 3305 engaging the strap receiving portion 3304 at a superior one of the plurality of angular positions forming a smaller angle $\alpha_2$ between the first and second parts of the top edge of the anterior strap portion loop.

By varying which of the plurality of possible positions on the strap receiving portion 3304 to engage the strap attachment portion 3305 in, the patient can adjust the direction and/or magnitude of the headgear vector. The phrase "headgear vector" is used herein to denote the magnitude and direction of the force applied by the headgear to the interfacing portion 3500. In the embodiment shown in FIGS. 7 to 15 the headgear vector is applied by the anterior strap portion loops to the connection portions 3306. In general, adjusting the position of the strap attachment portion 3305 in the superior-inferior direction will adjust the direction of the headgear vector. Adjusting the position of the strap attachment portion 3305 in the anterior-posterior direction will adjust the magnitude of the headgear vector by increasing or decreasing the size of the anterior strap portion loop. Increasing the size of the anterior strap portion loop increases the magnitude of the force applied by the headgear. Similarly, decreasing the size of the anterior strap portion loop decreases the magnitude of the force applied by the headgear.

Referring next to FIGS. 9 and 13 in particular, the width W of the strap receiving portion 3304 (measured orthogonal to the longitudinal midline of the rectangular surface of the anterior end of the strap receiving portion 3304, shown as a dashed line in FIG. 13) decreases from a posterior end to an anterior end thereof. In examples of the technology the width W is in the range of 40 to 100 mm. The widest portion of the strap receiving portion 3304 is substantially wider than the width of the strap attachment portion 3305 (e.g., two, three, or four times wider). The superior and inferior strap portions 3301, 3302 join the strap receiving portion 3304 adjacent the wider posterior end of the strap receiving portion 3304. In other words, the superior and inferior strap portions 3301, 3302 join the strap receiving portion 3304 posterior to the widest width W. The superior and inferior strap portions 3301, 3302 may continue to increase in width more posterior to the widest width W (e.g., the widest width W of the strap receiving portion 3304 may not be the widest portion of the positioning and stabilizing structure 3300). In the embodiment shown in FIGS. 7 to 15 the posterior end of the strap receiving portion 3304 has a generally triangular surface. One side of the triangular surface is the widest width W, and the triangular surface narrows in the anterior direction toward the strap attachment portion 3305. The superior and inferior strap portions 3301, 3302 are connected to respective superior and inferior corners of the triangular posterior end of the strap receiving portion 3304. The generally rectangular surface of the anterior end of the strap receiving portion 3304 is adjacent to the remaining corner of the triangular posterior end of the strap receiving portion 3304, as best seen in FIG. 13. The anterior end of the strap receiving portion 3304 may have a width approximately equivalent to the width of the strap attachment portion 3305. In some examples, the width of the anterior end may be equivalent to the width of the strap attachment portion 3305. In other examples, the width of the anterior end may be greater than the width of the strap attachment portion 3305. This may allow the strap attachment portion 3305 the ability to adjust to a greater plurality of angular positions while remaining within the boundaries of the strap receiving portion 3305.

The strap attachment portion 3305 may engage the posterior end of the strap receiving portion 3304 when in one or more of its possible positions. The posterior end of the strap receiving portion 3304 may overlie the cheek of the patient's face and preferably overlies the upper cheek region. The posterior end of the strap receiving portion 3304 is preferably relatively large, in some examples around 20 cm$^2$, to provide a large number of possible positions for engaging the strap attachment portion 3305 and therefore a greater range of possible headgear vectors. In other words, the area of the posterior end of the strap receiving portion 3304 is greater than the area of the strap attachment portion 3305, and can accommodate the strap attachment portion 3305 in a plurality of positions.

In the embodiment shown the strap attachment portion 3305 comprises a hook material. The strap receiving portion 3304 has a patient facing surface and an opposite non-patient facing surface. The non-patient facing surface is provided with an unbroken loop material to engage the hook material of the strap attachment portion 3305. In other embodiments the strap attachment portion 3305 may comprise an unbroken loop material and the non-patient facing surface of strap receiving portion 3304 comprises a hook material.

In some embodiments (shown in FIGS. 11 and 12) the connection portion 3306 comprises a slot 3315 through which the anterior strap portion 3303 passes. The slot 3315 is fully formed and bounded within the connection portion 3306. In other words, the perimeter of the slot 3315 is completely formed by the connection portion 3306. In other embodiments (not shown) the connection portion 3306 may comprise a hook formation which the anterior strap portion loop can engage. In other words, the hook represents a slot that is not fully formed. In this way the anterior strap portion 3303 can be removed from the connection portion 3306 without removing the strap attachment portion 3305 from the strap receiving portion 3304. This may enable the strap attachment portion 3305 to maintain substantially the same position relative to the strap receiving portion 3304. Thus the anterior strap portion 3303 may be removed from and reattached to the connection portion 3306 without substantially altering a headgear force vector provided by the anterior strap portion 3303.

FIG. 11 shows an embodiment wherein a connection portion 3306 is provided on each side of the interfacing portion 3500. The connection portions 3306 attach directly to the cushion module. In an example the connection portions 3306 are bonded permanently to the cushion module. In alternative examples the connection portion 3306 may be overmoulded to the cushion module. FIG. 12 shows an alternative embodiment comprising a single connection portion 3306 that attaches to the cushion module. The single connection portion 3306 is bonded to the cushion module on both the left and right hand sides and has slots 3315 on each of the left and right hand sides that engage the respective anterior strap portion loops.

Each of the connection portions 3306 comprise a slot 3315 which engages the anterior strap portion loop. To don or doff the patient interface 3000 the patient 1000 may detach the anterior strap attachment portion 3305 and feed the anterior strap portion 3303 through the slot 3315. However, as described further below, in examples of the technology selected portions of the headgear, for example some or all of the inferior strap portions 3302, can be stretched sufficiently to allow donning and doffing without detaching or adjusting either anterior strap portion 3303. In this way, the patient may not have to detach the anterior strap attachment portion 3305 from the strap receiving portion 3304, which helps to ensure that any adjustment made by the patient (e.g., positioning the strap attachment portion at an angle $\alpha_1$) is maintained for successive uses. In other words, the headgear can be adjusted once by the patient, and then remains appropriately adjusted whether or not the headgear is worn by the patient. This may be beneficial because the patient may be better assured that the seal-forming structure 3100 will be in the proper location on each successive use after they adjust the strap attachment portion 3305 to a preferred location (e.g., at a preferred angle $\alpha_1$) on an initial use.

In some embodiments (not shown) the connection portion 3306 attaches to a frame which connects to the cushion module. In some examples, the connection portion 3306 connects by a removable connection. In some examples this may comprise a magnetic catch. In other examples the connection may be through a clip attachment.

The ability to modify the direction and the magnitude of the headgear vector enables the patient to better create a seal between the seal-forming structure and the patient's face.

The connection portion 3306 may be rotationally fixed relative to the interfacing portion 3500 when the two are couple together. The cushion module (i.e., the seal-forming structure 3100 and/or the plenum chamber 3200) and the connection portion 3306 may therefore move together when the position of the strap attachment portion 3305 changes. If the strap attachment portion 3305 is attached substantially parallel to or at a relatively small angle relative to the inferior strap portion 3302 (i.e. such that two portions of the bottom edge of the anterior strap portion loop are substantially parallel or at a relatively small angle, for example an angle $\alpha_1$ less then 5°), the cushion module will pivot such that the superior portion of the cushion module moves in the posterior direction. For example, this may occur if the bottom edge of the strap attachment portion 3305 is collinear with or within approximately 5° from a bottom edge of the inferior strap portion 3302 and/or the bottom edge of the strap receiving portion 3304. If the strap attachment portion 3305 is attached at a larger angle, for example aligned with the superior strap portion 3301, (i.e. such that two portions of the bottom edge of the anterior strap portion loop are at a relatively large angle, for example angle $\alpha_2$ less than 5°), this causes the cushion module to pivot such that the superior portion of the cushion module moves in the anterior direction. For example, this may occur if a top edge of the strap attachment portion 3305 is collinear with or within approximately 5° from a top edge of the superior strap portion 3301 and/or a top edge of the strap receiving portion 3304. By adjusting the position of the strap attachment portion(s) 3305 the patient can achieve personalised sealing forces optimised for seal, stability and comfort.

In some embodiments the crown strap portion 3313 may overlie the parietal bone of the patient's skull, on or near the intersection of the parietal and frontal bones. In the embodiment shown in FIGS. 11 to 13 the crown strap portion 3313 comprises left 3307 and right 3308 crown strap portions, one portion having a buckle 3309 through which the end of the other portion can pass and be looped back and secured onto itself with hook and loop material or any other suitable attachment means. The length of the crown strap portion 3313 can then be changed to appropriately fit the particular size of the patient's head. For example, a greater portion of the left crown strap portion 3307 may be doubled back on itself through the buckle 3309 so that the length of the crown strap portion 3313 may be increased for a patient with a smaller head (e.g., so that the crown strap portion 3313 is not too loose on the patient's head). Alternatively, a lesser portion of the left strap portion 3307 may be doubled back on itself through the buckle 3309 so that the length of the crown strap portion 3313 may be decreased for a patient with a larger head (e.g., so that the crown strap portion 3313 is not too snug on the patient's head).

The left crown strap portion 3307 may also be completely removed from the buckle 3309 so that the crown strap portion 3313 is no longer continuous. This may assist the patient in donning or doffing the headgear. For example, the patient may be more easily capable of readjusting the length of the left crown strap portion 3307, because the crown strap portion 3313 has a lower effect on the seal-forming structure 3100 than the length and angle of the strap attachment portion 3305. By undoing the left crown strap 3307 from the buckle, the patient may maintain the strap attachment portion 3305 in a desired portion (e.g., supplying a desired headgear vector).

In the embodiments shown in FIGS. 7 to 15, crown strap portion 3313 is connected to back strap portion 3314 by two posterior connecting strap portions 3310 and/or each of the superior strap portions 3301 are joined to the inferior strap portions 3302 by the posterior connecting strap portions 3310. The back strap portion 3314 overlies, or lies inferior to, the occipital bone of the patient. The crown strap portion 3313, the back strap portion 3314 and the posterior connecting strap portions 3310 form a substantially loop shape (when viewed from above) and/or to define a substantially circular aperture through which the rear of the upper part of the patent's head protrudes.

In some embodiments (not shown) the headgear may comprise more than two anterior strap portions 3303. In alternate embodiments the anterior strap portion 3303 may be connected to only one of the superior or inferior strap portions 3301, 3302. The anterior strap may connect to an alternative strap or straps that form part of the headgear. In alternative embodiments the left superior and inferior strap portions 3301, 3302 may extend around the patient's head and attach to the respective right side superior and inferior strap portions 3301, 3302.

The two-point headgear increases modularity. Many different headgear styles are possible. A plurality of different headgear designs can include the anterior strap portions 3303 with the strap receiving and strap attachment portions 3304, 3305 and the plurality of possible positions. Additionally, provided the interfacing portion 3500 includes suitable connection portions 3306 the patient can choose the most comfortable or stable headgear from the different headgear styles.

In some embodiments the entire headgear may be formed from a single piece of material rather than separate pieces stitched or otherwise joined together. Alternatively, the headgear may comprise separate strap portions which are stitched or otherwise permanently joined to each other. Any one or more of the anterior, superior, inferior, crown and back strap portions defined above may be formed separately and subsequently connected to other headgear portions forming the headgear.

In the embodiment shown in FIGS. 13 to 15 the anterior strap portions 3303 further comprise a tab 3311 that projects outwardly from the anterior strap portion 3303 and helps prevent the anterior strap portion 3303 from accidentally slipping through the slot 3315 of connection portion 3306. This allows the anterior strap portions 3303 to be loosened substantially without completely slipping out of the slot 3315. In one embodiment the tab 3311 is formed from the material which forms the strap attachment portion 3305. In the example shown in FIG. 11 to FIG. 13 the posterior end of the strap attachment portion 3305 projects outwardly from the anterior strap portion 3303 to form tab 3311.

As shown in FIGS. 14 and 15, the tab 3311 is inclined and formed at an obtuse angle with respect to the strap attachment portion 3305. In other words, the tab 3311 is formed at an acute angle with respect to the remainder of the anterior strap portion 3303. The material used to construct the tab 3311 may also allow the tab 3311 to flex relative to the strap attachment portion 3305. The tab 3311 is also formed on the same side of the anterior strap portion 3303 as the strap attachment portion 3305.

The tab 3311 may flex as the strap attachment portion 3305 is inserted into the connection portion 3306. In other words, the tab 3311 may be larger than an opening in the connection portion 3306. As the strap attachment portion 3305 is inserted, the tab 3311 is pressed toward the anterior strap portion 3303 (e.g., toward the strap receiving portion 3304) so that the tab 3311 may fit through the connection portion 3306. Once the tab 3311 is completely through the connection portion 3306, the tab 3311 returns to its original position.

The tab 3311 may be coupled to the strap attachment portion 3305 using a one-way hinge. The tab 3311 may be permitted to flex toward the anterior strap portion 3303 (e.g., toward the strap receiving portion 3304), but cannot flex toward the strap attachment portion 3305 beyond the original position. In other words, the original position represents the smallest angle between the tab 3311 and the strap attachment portion 3305. Since the tab 3311 is larger than the opening to the connection portion 3306 in the original position, the tab 3311 cannot be removed from the connection portion 3306 simply by pulling in the opposite direction. In this way, the tab 3311 limits the strap attachment portion's 3305 ability to slip out of the connection portion 3306. To remove the strap attachment portion 3305, the patient may have to manually move the tab 3311 (e.g., press the tab 3311 toward the anterior strap portion 3303) in order to allow the tab 3311 to fit through the connection portion 3306. The tab 3311 may assist in preventing the various straps of the headgear from becoming tangled because the strap attachment portion 3305 remains connected (e.g., threaded) to the connection portion 3306.

When the strap attachment portion 3305 is connected to the strap receiving portion 3304, the tab 3311 is in contact with the strap receiving portion 3304. The strap attachment portion 3305 and the tab 3311 are disposed on an outer surface of the positioning and stabilizing structure 3300 when donned by the patient. In other words, the attachment portion 3305 and the tab 3311 are not ordinarily in contact with the patient's skin. After forming a loop, the tab 3311 may flex toward the anterior strap portion 3303 in order to facilitate the connection of the strap receiving portion 3304 and the strap attachment portion 3305. In other words, the tab 3311 may be substantially parallel with the strap attachment portion 3305 so that both contact the strap receiving portion 3304, and the tab 3311 does not obstruct the strap attachment portion 3305. The tab 3311 may include the same hook material as the strap receiving portion 3305, in order to increase the overall strength of the connection. Once the strap attachment portion 3305 is disconnected from the strap receiving portion 3304, the tab 3311 returns to the relaxed position. In other examples, the tab 3311 may be on the opposite side of the anterior strap portion 3303 than the strap attachment portion 3305 (e.g., the inner side), so that the tab 3311 is exposed and not in contact with the strap receiving portion 3304 when the loop is formed.

A benefit of a two-point headgear connection which maintains control of both the magnitude and direction of the headgear vector is that the patient may only need to adjust the two anterior strap portions 3303, rather than needing to adjust four connection points as is common with many examples of prior art headgear. Changing the direction of the headgear vector is also easier since it only requires adjustment of the position of the strap attachment portion(s) 3305. Many examples of prior art headgear require adjustment of both upper/superior and lower/inferior straps. The headgear of the present invention may therefore be easier to adjust. Additionally, if connecting portions are used that are releasably engageable with the interfacing portion 3500 then only initial setup may be required. Once adjusted, the headgear can be removed from the mask and so the patient can easily don and doff the patient interface 3000 without readjusting the headgear strap portions.

The two-point headgear may be less complicated than many examples of prior art headgear, and requires only two pieces of hook material and two connector portions. This may lead to an improved manufacturability and may result in easier, quicker, and/or cheaper manufacture of the headgear. The two-point headgear connection to the interfacing portion 3500 may also improve the manufacture of the interfacing portion 3500, as the interfacing portion 3500 only requires the capability to attach to two connection portions 3306. This will lead to a less complicated design and may result in easier, quicker, and/or cheaper manufacture of the headgear.

5.3.3.2 Stretch Capabilities

In one form of the technology, different regions of the headgear may comprise different properties. The headgear may comprise a textile or textile laminate material. The headgear may be in the form of a two-point connection headgear as described herein.

In examples the crown strap portion 3313 may comprise relatively limited stretch capabilities or stretchability in order to provide stability on and around the crown of the patient's skull. Preferably the crown strap portion 3313 has less stretchability (i.e. the amount of elongation per unit force) compared to some other portions of the headgear. The superior strap portion 3301, and anterior strap portions 3303 may also have limited stretch capabilities and preferably have less stretchability compared to some other portions of the headgear. The superior strap portion 3301 may have limited stretch capabilities in order to provide stability on and around the crown of the patient. The anterior strap portions 3303 may have limited stretch capabilities in order to hold the adjustment or provide stability at the interfacing portion. In other words, the crown strap portion 3313, the superior strap portion 3301, and the anterior strap portion 3303 may be relatively rigid compared to other straps of the headgear in order to maintain the shape of the headgear and assist in providing appropriate forces and comfort to the patient's head. Thus, the distance of elongation per unit force for the crown strap portion 3313, the superior strap portion 3301, and the anterior strap portion 3303 is less than other strap portions that comprise the headgear. The headgear may come in a variety of sizes (e.g., small, medium, large) in order to conform to patients with a variety of head sizes. In this way, the crown strap portion 3313, the superior strap portion 3301, and the anterior strap portion 3303 may not need to stretch, or otherwise deform, in order to meet size requirements for different patients. Instead, the crown strap portion 3313, the superior strap portion 3301, and the anterior strap portion 3303 may provide stability and/or rigidity regardless of the size of the individual patient's head.

The back strap portion 3314 may comprise a greater stretchability compared to the crown, superior and anterior strap portions. A greater stretchability in this area of the headgear allows the headgear to adjust to patients with different sized heads. The inferior strap portions 3302 may have relatively greater stretch capabilities (e.g., as compared to the superior and anterior strap portions 3301, 3303, the back strap portion 3314, etc.), preferably the most stretch compared to other portions of the headgear. Together, the inferior and back strap portions 3302, 3314 provide anterior/posterior flexion to the headgear, although the inferior strap portion 3302 may also provide some superior/inferior flexion (e.g., because the inferior strap portion 3302 extends in both the anterior/posterior and superior/inferior directions along the patient's head). In some embodiments, the headgear has sufficient elasticity to allow the headgear to be donned and doffed without undoing the strap attachment portion(s) 3305 or releasing the connection portions from the interfacing portion 3500. To don and doff the headgear the patient may pull the back of the headgear up and over the crown of the patient's head whilst the headgear is still connected to the interfacing portion 3500. The greater stretch capabilities of the back strap portion 3314 and the inferior strap portions 3302 may assist the patient in donning and doffing the headgear. In other words, the headgear (e.g., specifically the back strap portion 3314) may be pulled in the posterior direction, so that it does not directly apply tension to the patient's head. The gab created between the back strap portion 3314 and the patient's head permits the back strap portion 3314 to move in the superior direction along the patient's head, and eventually off of the patient's head. Stretching the back strap portion 3314 may also apply tension to the inferior strap portions 3302 (e.g., cause them to stretch). The stretching of the inferior strap portions 3302 may assist in maneuvering the headgear around the patient's ears in order to minimize discomfort. Since the superior strap portion 3301 and the anterior strap portion 3303 may have little to no stretch capabilities (e.g., as compared to the inferior strap portion 3302), the opening for the ear will not completely deform and pinch the patient's ear as the patient is removing the headgear.

The posterior connecting strap portions 3310 may have a stretch capability between that of the inferior strap portion 3302 and the superior strap portion 3301. The posterior connecting strap portions 3310 may be disposed in the anterior/posterior and the superior/inferior directions, and may be able to provide extension in both directions. The posterior connecting strap portions 3310 are preferably stiff enough to provide stability around the crown. Some or all of the posterior connecting strap portions 3310 may have a slightly greater stretch capability than the superior strap portion 3301 as these portions may need to stretch to assist when the patient is donning and doffing the headgear if the stretch of the inferior strap portion 3302 and/or the back strap portion 3314 is not enough to enable the headgear to clear the patient's head. In particular, the posterior connecting strap portions 3310 may provide extension mainly in the vertical direction, in order to provide additional extension to the mainly horizontal extension from the inferior and back strap portions 3314. In some embodiments, an inferior region of the posterior connecting strap portions 3310 comprises the greater stretch capability (e.g., than the rest of the posterior connecting strap portions 3310).

In some examples the region of the headgear with the greatest stretch capability is the area where the posterior connection strap portions 3310, inferior strap portions 3302 and the back strap portion 3314 join. The combined stretch capabilities of these straps may provide this area with the ability to stretch to the greatest length. In other words, the confluence of the three stretchable straps allows the headgear to achieve the greatest amount of total combined length extension (e.g., in both the anterior/posterior and superior/inferior directions). The holes 3312 also permit the posterior connection strap portions 3310 greater stretchability in both the anterior/posterior direction and in the superior/inferior direction.

In some embodiments, the headgear may be formed of different segments with different stretch capabilities. The different segments are joined together, for instance by stitching. The different segments may be formed of different materials. In other embodiments, the headgear may be formed from a single piece of material. The different strap portions may be formed, for example by knitting or weaving, to have different stretching capabilities. This may be done by knitting different structures in different regions. For example, rigidized threads may be added to portions of the headgear proximate to the superior strap portion 3301, the anterior strap portion 3303, and/or the crown strap portion 3313 in order to provide these regions with less stretchability than the remaining regions of the headgear.

In the example shown in FIGS. 11 to 13, this region is provided with a plurality of holes 3312 to increase the ability of the headgear to stretch. In particular, the holes 3312 may be concentrated on the posterior connecting strap portion 3310, although the holes 3312 may also be disposed on the inferior strap portion 3302 and the back strap portion 3314. The holes 3312 may be arranged in a particular pattern (e.g., in rows and columns, diagonal, etc.) or may be randomly disposed on the headgear. In other examples the stretchability of other regions of the headgear may be increased by providing similar holes. This feature may also increase the breathability of the region.

In the example shown in FIG. 13-1, the posterior connecting strap portion 3310 may be continuous, and not include holes 3312 or other discontinuities. Increased stretchability may instead be provided by the back strap portion 3314, which may be formed in two parts. For example, the back strap portion 3314 may comprise a first or upper back strap 3314a and a second or lower back strap 3314b.

In some forms, the upper back strap 3314a may be formed continuously with the posterior connecting strap portions 3310. In other words, a single piece of material may be used to form the upper back strap 3314a and the posterior connecting strap portions 3310. The end of each posterior connecting strap portion 3310 may be connected (e.g., stitched, thermally welded, etc.) to the respective side of the crown strap portion 3313 (e.g., the left crown strap portion 3307 or the right crown strap portion 3308).

In some forms, the upper back strap 3314a may be wider than the posterior connecting strap portions 3310. The width of the upper back strap 3314a may not be symmetrical with respect to the connecting strap portions 3310. Instead, the upper back strap 3314a may be flush with the posterior connecting strap portions 3310 on one side, and may protrude beyond the posterior connecting strap portions 3310 on the opposite side. The resulting shape of the combined upper back strap 3314a and the posterior connecting strap portions 3310 may be a T-shape. Each posterior connecting strap portion 3310 may be longer than the upper back strap 3314a.

In some forms, the lower back strap 3314b may be formed from a continuous piece of material, and may extend between each of the inferior strap portions 3302. Each end of the lower back strap 3314b may be connected (e.g., stitched, thermally welded, etc.) to the respective side of the inferior strap portion 3302.

In some forms, the upper back strap 3314a may be formed as a separate piece from the lower back strap 3314b. The two back strap portions 3314 may be connected (e.g., stitched, thermally welded, etc.) to one another. Specifically, the upper back strap 3314a may be coupled to the lower back strap 3314b along its entire length. An opening (e.g., sized to receive one of the patient's ears) may therefore be formed between each posterior connecting strap portion 3310, the upper back strap 3314a, and the lower back strap 3314b.

In some forms, the lower back strap 3314b is constructed from an elastic material, which may provide stretchability to the positioning and stabilizing structure 3300. Stretching the lower back strap 3314b may increase the distance between each inferior strap portion 3302, and/or a diameter of the opening. In either case, stretching the lower back strap 3314b may assist in allowing patient's with different sized heads comfortably don and doff the positioning and stabilizing structure 3300. The elastic material is configured to return to substantially its original length when a force is no longer applied so that the positioning and stabilizing structure 3300 remains substantially snug on the patient's head (e.g., automatic adjustments), and can be worn repeatedly without damaging (e.g., permanently deforming) the elastic material.

In some forms, the upper back strap 3314a may not be constructed from an elastic material, and may instead be constructed from an inextensible or substantially inextensible material. Thus, the upper back strap 3314a may not be capable of stretching or extending the same amount as the lower back strap 3314b. In particular, the inextensibility of the upper back strap 3314a may limit the stretchability of the lower back strap 3314b (e.g., since they are connected together). For example, the connection means between the upper and lower back straps 3314a, 3314b, along the length of the upper back strap 3314a, limits the stretchability of the connected portion of the lower back strap 3314b to being no greater than that of the upper back strap 3314a. Accordingly, a central section (e.g., positioned to contact the patient's head proximate the occiput) of the back strap portion 3314 may stretch less than sides of the back strap portion 3314.

In certain forms, the outer regions of the lower back strap 3314b may be able to stretch, while the central region of the lower back strap 3314b is held relatively stiff by the connection to the upper back strap 3314a. The total length of extension may be less (e.g., as compared to an unconnected lower back strap 3314b), but the lower back strap 3314b may still be able to stretch to accommodate various sizes of heads.

In some forms, the elasticity of the lower back strap 3314b may allow a patient to don and/or doff the positioning and stabilizing structure 3300 without removing the strap attachment portions 3305 from the respective connection portion 3306. By removing the positioning and stabilizing structure 3300 without removing the strap attachment portions 3305, the patient may not have to readjust the strap attachment portion 3305 each use, and so that that seal-forming structure 3100 may have substantially the same sealing force with each use.

In the examples shown in FIGS. 9 and 10, the posterior connecting strap portions 3310 comprise a mesh material, which may be used in place of the holes 3312. In other words, as opposed to manufacturing holes 3312 into the material of the posterior connecting strap portion 3310, the posterior connecting strap portion 3310 is constructed from a material already containing holes. Additionally, the mesh material may be used along the entire length of the posterior connecting strap portions 3310, as opposed to concentrating the holes in a particular location. This may provide the entire posterior connecting strap portion 3310 with a uniform stretchability (e.g., as opposed to having a greater stretchability proximate to the inferior strap portion 3302 and the back strap portion 3314).

As shown in FIG. 9, the mesh material used to construct the posterior connecting strap portions 3310 may be similar to the material used for the remainder of the headgear, and may approximate the texture and/or feel of the other textile sections of the headgear. The mesh material may also approximate the texture and/or feel of ordinary bedclothes. The headgear may have a visually continuous look, so that a transition between the mesh and non-mesh materials may be less apparent. Additionally, the mesh material may be substantially flush with the remainder of the headgear. The continuous look and/or flush construction may also lead to increased patient comfort, as there may not be obtrusive joints connecting different materials, and/or materials with substantially the same feel contact the patient across the headgear.

In the illustrated example, the holes in the mesh material may be smaller than the holes 3312. Although in other examples, the holes in the mesh material may be larger, and more spaced apart, as compared to the holes 3312. The headgear may be constructed with mesh material having different sized holes in order to vary the feel and/or comfort of the patient.

As shown in FIG. 10, the mesh material used to construct the posterior connecting strap portions 3310 may be visually and/or tactilely distinct for the material used for the remainder of the headgear. For example, the mesh material may be recessed with respect to the rest of the headgear, and/or the mesh material may include a number of closely spaced holes (e.g., closer together than the mesh material shown in FIG. 9). The smaller sized holes in the mesh material may allow for less total length extension. However, the posterior connecting strap portions 3310 in FIG. 10 may be thinner and/or lighter than the posterior strap portions 3310 in FIG. 9. This may make the overall headgear lighter and more flexible, which may increase patient compliance.

This mesh increases the breathability of the posterior connecting strap portions 3310. Increasing the breathability in the headgear may assist in limiting moisture (e.g., sweat) that may otherwise become trapped (e.g., soak into) into the posterior connecting strap portions 3310 (or other areas of the headgear that use a mesh material). Increasing the breathability allows moisture to more easily evaporate while the patient is wearing the headgear. This may help to limit frequency that the patient overheats from wearing the patient interface 3000, and/or may assist in reducing moisture build-up caused by wearing the headgear. Additionally, breathability may limit the material from becoming waterlogged, which increases the weight, and possibly the discomfort, of the patient. Any of these reasons (or any other similar reason) may improve patient compliance, because the headgear may more closely approximate the feel and wearability of clothing, as opposed to a medical device, which the patient may associate with a feeling of discomfort.

The mesh material used in FIG. 10 may provide the most breathability, since it is lighter and thinner than the mesh material of FIG. 9. Thus, airflow throughout a room (e.g., a bedroom) may more easily reach the patient's skin beneath the headgear (e.g., the mesh material of FIG. 10 may offer less impedance). Additionally, a more breathable material (e.g., like the thinner mesh material of FIG. 10) may decrease the amount a patient sweats, and/or may be able to more effectively evaporate sweat because of the low impedance of the mesh material. While the mesh material of FIG. 9 (e.g., a thicker mesh material), may not offer an impedance as low as the mesh material of FIG. 10, it may still assist a patient in reducing sweat and/or remaining comfortable while wearing the headgear.

In other examples other portions of the headgear may also comprise a mesh or other breathable fabric. For example, any of the straps in the headgear may be constructed from a mesh material, up to, and including, constructing the entire headgear from one or more mesh materials. Constructing additional straps of the headgear from a mesh material may further reduce the overall weight and/or thickness of the headgear. Additionally, constructing straps that contact locations on the patient's head that produce more sweat from a mesh material may be beneficial, as these locations may require more airflow, and therefore would benefit from a more breathable material. Alternatively or in addition, it may be beneficial to use mesh material in straps that overlap the patient's hair, as hair may be wet (e.g., because of showering) prior to a patient donning the headgear.

Some patient's may not sweat as much, and may not require the additional breathability provided by the mesh material of FIG. 10. Additionally, some patient's may prefer the more uniform feel provided by the inclusion of the mesh material in FIG. 9, and may prefer the added comfort provided by the mesh material of FIG. 9, as compared to the added breathability provided by FIG. 10.

In some examples, multiple types of mesh material may be used in constructing the headgear. For example, some straps may be constructed from a thicker mesh material (see e.g., FIG. 9), and some straps may be constructed from a thinner mesh material (see e.g., FIG. 10). In addition, mesh materials not explicitly illustrated in these examples may also be included in the headgear. For example, a mesh material may be used to construct the anterior strap portion 3303 and/or the crown strap portion 3313. All of these factors, like breathability and/or comfort, may be specific to an individual patient, and headgear could be individually designed and tailored to a specific patient.

In the examples shown in FIGS. 7 to 10, the inferior strap portion 3302 comprises stretchability indicator lines 3317. These lines act as a visual cue to indicate the stretchability of these portions. In other words, the lines 3317 may not assist the inferior strap portion 3302 in stretching, but may simply indicate to a patient where the inferior strap portion 3302 does stretch. The stretchability indicator lines 3317 may also assist a patient in determining a proper size for the headgear. For example, if the indicator lines 3317 are spaced too far apart when the headgear is worn (e.g., sizes of the patient's head is stretching the inferior strap portion 3302 beyond its limit), the patient may be alerted to choose a different sized headgear. This may help to maintain generally elastic deformation when the inferior strap portion 3302 (or any other strap portion of the headgear) stretches, so that the proper fit and application of tension may be applied to the patient during each successive use. If the inferior strap portion 3302 stretches too far (e.g., as indicated by the indicator lines 3317), the inferior strap portion 3302 may experience plastic deformation, and may be unable to apply the necessary tensile forces on successive nights. In other words, the inferior strap portion 3302 may stretch beyond its limit, and may be unable to return to its initial shape when removed from the patient's head.

In other examples (not shown) these lines may be cut out of the fabric and/or may comprise a mesh material that adds to the stretchability and breathability of this region. For example, holes 3312 (see e.g., FIG. 11) may replicate the lines, and provide both visual indication as well as added stretchability. Thus, the lines 3317 may serve an additional, functional purpose to provide the inferior strap portion 3302 with additional length extension. By cutting out holes and/or spacing the mesh material apart, the inferior strap portion 3302 (and/or other strap portions), the contrasting regions (e.g., opening and/or materials) replicate the lines 3317 that act purely as a visual cue.

5.3.3.3 Shape Holding Capabilities

In some embodiments the headgear may have shape holding capabilities such that when not in use the headgear still maintains the 3D shape and structure of when the headgear is in use. In other words, the headgear may be able to stand vertically upright on a table, and not fall over when not supported. This ability makes it easier to don and doff the headgear. This also has the advantage of preventing tangling of the headgear when it is not in use and prior to putting it on. For example, the headgear may stay upright and the various strap portions will remain spaced apart. The tabs 3311 may further assist with preventing the tangling of the headgear, since the free ends (e.g., the strap attachment portions 3305) may not be removed from the connection portion 3306.

The shape holding capability may be achieved by increasing the rigidity in one or more portions of the headgear material. In some examples most of the headgear has a high rigidity except for the inferior strap portion 3302, the back strap portion 3314, and/or the posterior connecting strap portions 3310. In examples where the headgear comprises a foam in the textile laminate, an increase in the foam stiffness can be used to increase the rigidity of that headgear portion. In other examples, stitching containing rigidized threads may be added to provide increased stiffness to the strap portions. In any example, increasing the rigidity of the headgear is done without substantially adding unnecessary weight (and therefore reducing patient compliance).

In one example, increasing the stiffness in the superior strap portions 3301 may allow them to retain their spacing from the inferior strap portion 3302 when the headgear has been removed. Although the posterior connecting strap portions 3310 may be unable to support the weight of the crown strap portion 3313 (e.g., because the mesh material is not stiffened to provide stretchability), the superior strap portions 3301 may retain some vertical support so that while the crown strap portion and the posterior connecting strap portions fold toward the ground. By providing stiffness to the superior strap, at least some of the straps of the positioning and stabilizing structure 3300 may remain separate, therefore reducing the likelihood of tangling, and simplifying the process of donning the headgear on a successive use.

The shape holding capabilities and the rigidity of the headgear will depend on the specific design and material choices of the headgear.

5.3.3.4 Conduit Attachment to the Headgear

FIGS. 16 and 17 show a further embodiment of the headgear wherein the headgear is connected to air circuit 4170. In the embodiment shown in FIGS. 16 and 17 the air circuit 4170 comprises two conduits 4171, 4172 that attach to the respective left and right hand sides of the patient interfacing portion 3500. The two conduits 4171, 4172 join to form a single conduit that connects to the RPT device 4000. The two conduits 4171, 4172 of the air circuit 4170 are configured to connect to the headgear in use. In some embodiments (not shown) the air circuit 4170 may comprise a single conduit that attaches to either the left or right hand side of the headgear.

In the embodiment shown the air circuit 4170 does not contribute to the positioning and stabilising structure and does not assist in maintaining the seal of the cushion module with the patient's face. Movement of the air circuit 4170 or patient interface 3000 may cause forces to be applied by the air circuit 4170 to the interfacing portion 3500. These forces may be decoupled from the mask in order to not affect the stabilising forces, or headgear vectors, provided by the headgear. In some examples, each conduit 4171, 4172 has a concertina type arrangement 4173 adjacent the connection to the interfacing portion 3500 in order to decouple forces between the air circuit 4170 and the interfacing portion 3500. The concertina arrangement may also enable the conduit 4171, 4172 to change length in this region to shorten or lengthen as required when the headgear is adjusted. For example, when the anterior strap portion loop increases in size the concertina arrangement of the conduit 4171, 4172 may decrease in length. Similarly, when the anterior strap portion loop decreases in size the concertina arrangement of the conduit 4171, 4172 may increase in length. In other words, when the patient has a smaller head (i.e., a greater length of the strap attachment portion 3305 is threaded through the connection portion 3306), the conduit 4171, 4172 has less distance to travel in order to reach the plenum chamber 3200, as opposed to when the patient has a larger head (i.e., a smaller length of the strap attachment portion 3305 is threaded through the connection portion 3306).

The concertinas 4173 may also move independently of the positioning and stabilizing structure 3300. In other words, extension or stretching of one of the strap portions (e.g., the posterior connecting strap portion 3310), does not necessarily equate to extension or stretching of the concertinas 4173. If the concertinas 4173 and the posterior connecting strap portions 3310 both stretch, they do not necessarily stretch the same amount. For example, the conduits 4171, 4172 may be constructed to be used with a wide variety of sizes of patient heads, while the positioning and stabilizing structure 3300 may only be constructed for a smaller variety of heads. Thus, the headgear of the positioning and stabilizing structure 3300 and the conduits 4171, 4172 need to be able to move separately (e.g., stretch different distances and in different directions).

FIGS. 16 and 17 show left conduit 4171 passing through respective loops 3316 located on the superior strap portion 3301 and the crown strap portion 3313. In the embodiment shown there are two loops 3316 located on each side of the headgear, one located near the top of the crown strap portion 3313 and the other on the superior strap portion 3301 between the patient's eye and ear. In alternate embodiments there may be more than two loops or only a single loop. In embodiments with a single loop, the single loop may extend along a larger part of the length of the superior strap portion 3301 and/or the crown strap portion 3313.

In some examples the loops 3316 may be removably connected to the superior strap portion 3301 by a hook and loop attachment, a clip, Velcro, and/or a magnetic attachment. The conduits 4171, 4172 may be positioned against the superior strap portion 3301, and the loops may be connected once the conduits 4171, 4172 are in the desired location. Similarly, the conduits 4171, 4172 may be disconnected and removed from the positioning and stabilizing structure 3300 by undoing the loops 3316 and allowing the conduits 4171, 4172 the ability to move away from the positioning and stabilizing structure 3300.

In some examples, the loops 3316 may be permanently connected to the superior strap portion 3301. The conduits 4171, 4172 may be removably connected to the plenum chamber 3200, and may be threaded through the loops 3316 prior to being connected to the plenum chamber 3200. The positioning and stabilizing structure 3300 may be alternatively constructed around the conduits 4171, 4172, which may or may not be removably coupled to the plenum chamber 3200.

In the embodiment shown, the conduits 4171, 4172 are flexible enough to move if contacted during adjustment or donning/doffing of the headgear. In some embodiments (not shown) there may be a sufficiently large gap between the conduit 4171, 4172 and the strap receiving portion 3304 to avoid the conduit 4171, 4172 interfering with adjustment of the anterior strap portion 3303. In other embodiments (not shown) the position or angle of the conduit connection with the interfacing portion and/or the position or angle of the connection portion 3306 may be adjustable and/or may be selected such that the conduit does not overlie the strap receiving portion. The patient or technician may move the conduit away from the anterior strap portion 3303 when adjusting the anterior strap portion loop, and may move the conduit back into place once the headgear is properly adjusted. Provision of concertina arrangements, as described above, may assist in making the conduit easy to move in this way.

Having the air circuit attached to the headgear may improve the aesthetics of the mask. It may also reduce the risk of the air circuit 4170 interfering with the patient while they are sleeping.

5.3.3.5 Frame

As shown in FIGS. 18-20, some forms of the patient interface 3000 include a frame 3350 formed as part of the positioning and stabilizing structure 3300. The frame 3350 may assist in providing connection between the headgear and the interfacing portion 3500. The frame 3350 may be used in place of the connection portion 3306.

In some forms, the frame 3350 may be permanently coupled to the interfacing portion 3500. In other words, the frame 3350 may not be removable without causing damage to the interfacing portion 3500. In these forms, the connection portion 3306 may not be needed, as its function may be performed by the frame 3350. For example, the frame 3350 may include at least one slot 3352, which is similar to the slots 3315 of the connection portion 3306 described above.

In certain forms, the frame 3350 may be secured to the interfacing portion 3500 using an adhesive, a mechanical fastener, and/or a similar method, so that the frame 3350 permanently coupled to the cushion module, and may be unable to be removed from the cushion module.

In some forms, the frame 3350 may be removably coupled to the interfacing portion 3500. A patient may selectively couple the frame 3350 to the interfacing portion 3500 based on various factors like personal preference, seal optimization, or other similar reasons. For example, the connection portion 3306 and the frame 3350 may be used interchangeably, with the patient able to switch between either as they desire.

In certain forms, the frame 3350 may be removably secured to the interfacing portion 3500 using an adhesive, a mechanical fastener, a snap-fit, a friction fit, and/or a similar method, so that the frame 3350 may be repeatedly removed and reattached.

In some forms, the frame 3350 may be constructed from a rigid or semi-rigid material (e.g., hard plastic). The rigid construction of the frame 3350 may limit bending in the frame 3350. This may assist in maintaining the same orientation of the frame with respect to the interfacing portion 3500 (e.g., the slots 3352 may be limited from moving in the anterior-posterior direction as a result of bending in the frame 3350). The frame 3350 may also be more rigid than the interfacing portion 3500, and may assist in maintaining a shape of the plenum chamber 3200 (e.g., the frame 3350 may prevent excessive deformation, which may create leaks in the seal-forming structure 3100).

As shown in FIG. 18, the frame 3350 may have a central portion with an annular shape. In other words, the frame 3350 may have an opening 3354 formed at least partially within the perimeter of the frame 3350.

In certain forms, a connection port 3600 (e.g., an elbow) may connect to a central portion of the plenum chamber 3200. The opening 3354 of the frame 3350 is sized to extend beyond the footprint of the connection port 3600, so as to avoid contact with the connection port 3600 (e.g., when removing the frame 3350 from the cushion module).

In certain forms, the headgear is connected to air circuit 4170, including conduits 4171, 4172 (see e.g., FIGS. 16 and 17). In these forms, an elbow 3600 may not be coupled to the plenum chamber 3200. A front or anterior surface of the plenum chamber 3200 may be transparent and/or translucent. The opening 3354 of the frame 3350 may allow a patient, clinician, or other individual observe the inside of the plenum chamber 3200 (e.g., to check for debris, to examine fit of seal-forming structure 3100, etc.).

In some forms, the frame 3350 includes at least one mounting portion 3356. In the illustrated example, the frame 3350 includes two mounting portions 3356, one on either side of the frame 3350. The mounting portions 3356 may extend toward a center of the opening 3354. In the illustrated example, the mounting portions 3356 are disposed proximate a lower end of the frame 3350. The mounting portion 3356 may be part of the central portion of the frame 3350, and may be fixed when coupled to the interfacing portion 3500.

In some forms, a tab 3358 may be disposed proximate to the respective mounting portion 3356. Each tab 3358 may be biased in a direction away from the respective mounting portion 3356, and may be movable in a direction toward the mounting portion 3356 (e.g., via a patient's finger). Each mounting portion 3356 may act as a stop for the respective tab 3358 (e.g., to limit the movement of the tab 3358). The tabs 3358 may be cantilevered in order to permit movement. In a rest position, at least a portion of each tab 3358 is spaced apart from the respective mounting portion 3356 in an anterior direction (e.g., see FIGS. 19 and 20).

In some forms, each tab 3358 includes grooves 3360. For example, each illustrated tab 3358 includes three grooves 3360. The grooves 3360 may be evenly spaced along each of the tabs 3358.

In some forms, the frame 3350 also includes at least one movable portion 3362. The illustrated example includes two movable portions 3362, one on either side of the frame 3350. Each movable portion 3362 may include one slot 3352. Movement of each movable portion 3362 may change the position and/or orientation of the respective slot 3352.

In some forms, a projection 3364 extends from each of the slots 3352. The projections 3364 may have a generally triangular shape, and may extend toward the opening 3354. The projections 3364 may be sized to fit within the respective grooves 3360. Engagement between the projections 3364 and grooves 3360 may form a ratchet system, which may selectively allow movement of the slots 3352 (e.g., via the movable portion 3362).

In some forms, moving the tab 3358 toward the respective mounting portion 3356 (e.g., into a flexed position) moves the grooves 3360 away from the projection 3364. When the tab 3358 contacts the mounting portion 3356 (e.g., and is unable to move further in that direction), the projection 3364 may be completely out of any groove 3360, and the movable portion 3362 may be free to move. For example, each movable portion 3362 may move along a direction 3366, 3368 that substantially follows the contour of the central portion of the frame 3350 around the opening 3354. Each of the movable portions 3362 may be movable separately from one another (e.g., each tab 3358 is actuated separately).

While the projection 3364 is spaced apart from the grooves 3360, the movable portion 3362 may move (e.g., slide) in the superior-inferior direction (e.g., as seen in FIGS. 19 and 20), thereby moving the respective slot 3352 in the substantially same direction. The patient may move the movable portion 3362 so that one of the grooves 3360 is aligned with the projection 3364. Once the movable portion 3362 has been appropriately positioned (e.g., according to patient preference, clinician instructions, etc.), the patient may release the tab 3358, allowing it to return to its relaxed position (e.g., the tab 3358 may be biased toward the relaxed position). The selected groove 3360 receives the projection 3364, and selectively locks movement in the movable portion 3362.

As shown in FIGS. 19 and 20, the patient may adjust the position of each movable portion 3362 while wearing the patient interface 3000. As described above, there may be three grooves 3360 per tab 3358 (i.e., three different orientations for each movable portion 3362). The orientations may include a superior orientation (e.g., when the projection 3364 is in the upper groove 3360), a neutral orientation (e.g., when the projection 3364 is in the middle groove 3360), and an inferior orientation (e.g., when the projection 3364 is in the lower groove 3360). The patient may adjust each movable portion 3362 to the same orientation, so that the force provided by the positioning and stabilizing structure 3300 is in substantially the same direction on either side of the patient's head.

Moving the movable portions 3362 into the different orientations may affect the direction of the forces provided by the positioning and stabilizing structure 3300. For example, if the movable portions 3362 are moved to the superior orientation, the superior portion of the seal-forming structure 3100 pivots toward the patient's face (e.g., the patient's nose) and an inferior portion of the seal-forming structure 3100 pivots away from the patient's face (e.g., the patient's mouth). In this orientation, a portion of the force vector supplied by the straps of the positioning and stabilizing structure 3300 is directed in the inferior direction, and may assist in providing a stronger seal around the patient's nose. Alternatively, if the movable portions 3362 are moved to the inferior orientation, the superior portion of the seal-forming structure 3100 pivots away from the patient's face (e.g., the patient's nose) and the inferior portion of the seal-forming structure 3100 pivots toward the patient's face (e.g., the patient's mouth). In this orientation, a portion of the force vector supplied by the straps of the positioning and stabilizing structure 3300 is directed in the superior direction, and may assist in providing a stronger seal around the patient's mouth. Finally, in the neutral position, the force vector is directed substantially in the posterior direction.

Moving the movable portions 3362 may enable the seal-forming structure 3100 to rotate in the mid-sagittal plane, and may allow the seal-forming structure 3100 to seal with multiple facial profiles. In this way, a patient may not need to adjust an upper and/or a lower headgear strap to achieve a proper seal for the patient's specific face. In other words, the patient may move the movable portions 3362 between finite positions (i.e., the superior, neutral, and inferior orientations) in order to easily make adjustments, while still allowing for adjustments to fit the facial features of different patients.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components, including pneumatic components 4100, in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

5.4.1.4 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

5.5 Air Circuit

An air circuit 4170 in accordance with an aspect of the present technology is a conduit or a tube constructed and arranged to allow, in use, a flow of air to travel between two components such as RPT device 4000 and the patient interface 3000. Examples of an air circuit 4170 are described above.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Anatomy 5.8.2.1 Anatomy of the Face (nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Nares (Nostrils): Approximately ellipsoidal apertures forming the entrance to the nasal cavity. The singular form of nares is naris (nostril). The nares are separated by the nasal septum.

5.8.2.2 Anatomy of the Skull

Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.3 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.4 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.4.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.4.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.4.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.4.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

REFERENCE SIGNS LIST

1000 Patient
1100 Bed partner
3000 Patient interface
3100 Seal-forming structure
3200 Plenum chamber
3210 Chord 3220 Superior point
3230 Inferior point
3300 Positioning and stabilising structure
3301 Superior strap portion
3302 Inferior strap portion
3303 Anterior strap portion
3303A Anterior strap portion
3304 Strap receiving portion
3305 Strap attachment portion
3306 Connection portion
3307 Left crown strap portion
3308 Right crown strap portion
3309 Buckle
3310 Posterior connecting strap portion
3311 Tab
3312 Holes
3313 Crown strap portion
3314 Back strap portion
3314a Upper back strap
3314b Lower back strap
3315 Slot
3316 Loops
3317 Stretchability indicator lines
3350 Frame
3352 Slot
3354 Opening
3356 Mounting portion
3358 Tab
3360 Groove
3362 Movable portion
3364 Projection
3366 Direction
3368 Direction
3400 Vent
3500 Interfacing portion
3600 Connection port
3700 Forehead support
4000 RPT device
4010 External housing
4012 Upper portion
4014 Lower portion
4015 Panel(s)
4016 Chassis
4018 Handle
4020 Pneumatic block
4100 Pneumatic components
4110 Air filters
4112 Inlet air filter
4114 Outlet air filter
4120 Muffler
4122 Inlet muffler
4124 Outlet muffler
4140 Pressure generator
4142 Blower
4144 Brushless DC motor
4160 Anti-spill back valve
4170 Air circuit
4171 Left conduit
4172 Right conduit
4180 Supplemental oxygen
4200 Electrical components
4202 Printed Circuit Board Assembly (PCBA)
4210 Power Supply
4220 Input devices
4270 Transducers
5000 Humidifier
5002 Humidifier inlet
5004 Humidifier outlet
5006 Humidifier base
5110 Reservoir
5120 Conductive portion
5130 Humidifier reservoir dock
5135 Locking lever
5150 Water level indicator
5240 Heating element

The invention claimed is:
1. A patient interface comprising:
a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;
a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and
a positioning and stabilising structure to provide a force to hold the seal-forming structure in a therapeutically effective position on a patient's head, the positioning and stabilising structure comprising:
a superior strap portion configured to, in use, extend over at least a portion of the patient's cheek and between the patient's eye and ear, the superior strap portion having first and second lateral edges that define a width of the superior strap portion along at least a portion of the superior strap portion;
an inferior strap portion configured to, in use, extend over a region of the patient's head below and/or behind the patient's ear, the inferior strap portion having first and second lateral edges that define a width of the inferior strap portion along at least a portion of the inferior strap portion;
the first and second lateral edges of the superior strap portion being spaced from the first and second lateral edges of the inferior strap portion;
a posterior connecting strap portion connected to or formed integrally with the superior strap portion and the inferior strap portion;
an anterior strap portion connected to or formed integrally with the superior strap portion and the inferior strap portion, and spaced apart from the posterior connecting strap portion,
wherein the superior strap portion has a posterior end portion and an anterior end portion, and the inferior strap portion has a posterior end portion and an anterior end portion,
wherein the posterior connecting strap portion interconnects the posterior end portion of the superior strap portion and the posterior end portion of the inferior strap portion, and wherein the anterior strap portion interconnects the anterior end portion of the superior strap portion and the anterior end portion of the inferior strap portion,
wherein the anterior strap portion comprises:
a strap receiving portion; and a strap attachment portion which is releasably connectable to the strap receiving portion such that the anterior strap portion forms a loop, wherein in use the loop is configured to engage a connection portion coupled to the plenum chamber;

wherein the strap receiving portion is configured to engage the strap attachment portion in a selected one of a plurality of possible positions when the patient interface is worn, wherein the posterior connecting strap portion is constructed from a mesh material different than the material used to construct the superior strap portion and the inferior strap portion; and wherein the posterior connecting strap portion has: 1) a greater stretch capability than the superior strap portion and, 2) a lesser stretch capability than the inferior strap portion, wherein the stretch capabilities allow the positioning and stabilizing structure to be removable from the patient's head when the loop engages the connection portion.

2. The patient interface according to claim 1, wherein the positioning and stabilizing structure further comprises a back strap connected to or formed integrally with the posterior connecting strap portion, the back strap having a stretch capability greater than the superior strap portion.

3. The patient interface according to claim 2, wherein the inferior strap portion has a greater stretch capability than the back strap.

4. The patient interface according to claim 1, wherein the inferior strap portion includes indicator lines, which act as a visual cue to indicate stretch capability.

5. The patient interface according to claim 1, wherein the mesh material is flush with the superior strap portion and the inferior strap portion.

6. The patient interface according to claim 1, wherein the mesh material is recessed with respect to at least one of the superior strap portion and the inferior strap portion.

7. The patient interface according to claim 1, wherein the superior strap portion and the inferior strap portion are constructed at least partially from a textile material.

8. The patient interface according claim 7, wherein the superior strap portion is constructed from a foam within the textile material in order to provide increased rigidity to the positioning and stabilizing structure.

9. The patient interface according to claim 1, wherein the positioning and stabilizing structure further comprises a crown strap portion connected to or formed integrally with the posterior connecting strap portion, the crown strap portion having a stretch capability less than the posterior connecting strap portion.

10. The patient interface according to claim 9, wherein the crown strap portion and the superior strap portion are inextensible.

11. The patient interface according to claim 9, wherein the crown strap portion comprises a left crown strap portion and a right crown strap portion, wherein one of the left and right crown strap portions has a buckle through which the end of the other of the left and right crown strap portions can pass and be looped back and secured onto itself in order to couple the left crown strap portion to the right crown strap portion.

12. The patient interface according to claim 11, wherein the positioning and stabilizing structure is configured to be removed from the patient's head by decoupling the left crown strap portion and the right crown strap portion, and without disengaging the strap attachment portion from the strap receiving portion.

13. The patient interface according to claim 1, wherein the greatest stretch capability of the positioning and stabilising structure is in an area where the posterior connecting strap portion and the inferior strap portion join.

14. The patient interface according to claim 1, wherein the strap attachment portion includes a tab configured to allow engagement with the connection portion, and limit disengagement from the connection portion.

15. The patient interface according to claim 1, wherein when the strap receiving portion is connected to the strap attachment portion, the strap receiving portion has a width that is greater than a width of the strap attachment portion at least over a portion of the region where the strap receiving portion contacts the strap attachment portion.

16. The patient interface according to claim 1, wherein the superior strap portion, the inferior strap portion and the posterior connecting strap portion together at least partially form an opening to receive the patient's ear without extending over the patient's ear during use.

17. The patient interface according to claim 1, wherein the posterior connecting strap portion is configured to, in use, engage a portion of the patient's head posterior of the patient's ear.

18. A patient interface for treatment of sleep disordered breathing, comprising:
  a cushion module comprising:
    a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;
    a pair of connection portions coupled to the plenum chamber on respective sides thereof; and
    a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and
  a positioning and stabilising structure to provide a force to hold the cushion module in a therapeutically effective position on a patient's head, the positioning and stabilising structure comprising:
    a pair of a superior strap portions configured to, in use, extend over at least a portion of the patient's cheek and between the patient's eye and ear on respective sides of the patient's head;
    a pair of inferior strap portions configured to, in use, extend over a region of the patient's head below and/or behind the patient's ear on respective sides of the patient's head;
    a pair of a posterior connecting strap portions respectively connected to or formed integrally with a respective one of the superior strap portions and a respective one of the inferior strap portions;
    a pair of anterior strap portions respectively connected to or formed integrally with a respective one of the superior strap portions and a respective one of the inferior strap portions, the pair of anterior strap portions being spaced apart from the pair of posterior connecting strap portions;

wherein the positioning and stabilising structure has only two connection points with the cushion module, the connection points being provided at respective sides of the cushion module by respective attachment of the pair of anterior strap portions to the pair of connection portions, wherein each anterior strap portion comprises:
  a strap receiving portion; and
  a strap attachment portion which is releasably connectable to the strap receiving portion such that the anterior strap portion forms a loop, wherein in use the loop is configured to engage a respective one of the connection portions;
    wherein the strap receiving portion is configured to engage the strap attachment portion in a selected one of a plurality of possible positions when the patient interface is worn,
    wherein the posterior connecting strap portion has: 1) a greater stretch capability than the superior strap portion and, 2) a lesser stretch capability than the inferior strap portion, wherein the stretch capabilities allow the positioning and stabilizing structure to be removable from the patient's head when the loop engages the connection portion, and
  wherein the patient interface does not comprise a forehead support.

19. The patient interface according to claim 18, wherein the pair of posterior connecting strap portions comprise a mesh material different than the material used to construct the superior strap portions and the inferior strap portions.

20. The patient interface according to claim 18, wherein the positioning and stabilizing structure further comprises a back strap connected to or formed integrally with the pair of posterior connecting strap portions, the back strap having a stretch capability greater than a stretch capability of the superior strap portions.

21. The patient interface according to claim 20, wherein the inferior strap portions have a stretch capability that is greater than a stretch capability of the back strap.

22. The patient interface according to claim 18, wherein the superior strap portions and the inferior strap portions are constructed at least partially from a textile material.

23. The patient interface according claim 22, wherein the superior strap portions comprise a foam and textile laminate structure, the superior strap portions having increased rigidity as compared to the inferior strap portions.

24. The patient interface according to claim 18, wherein the positioning and stabilizing structure further comprises a crown strap portion connected to or formed integrally with the pair of posterior connecting strap portions, the crown strap portion having a stretch capability less than a stretch capability of the posterior connecting strap portions.

25. The patient interface according to claim 18, wherein each strap attachment portion includes a tab configured to allow engagement with a respective one of the connection portions, and limit disengagement from the connection portion.

26. The patient interface according to claim 18, wherein each superior strap portion has a posterior end portion and an anterior end portion, and each inferior strap portion has a posterior end portion and an anterior end portion, wherein each posterior connecting strap portion interconnects the posterior end portion of a respective one of the superior strap portions and the posterior end portion of a respective one of the inferior strap portions, and each anterior strap portion interconnects the anterior end portion of a respective one of the superior strap portions and the anterior end portion of a respective one of the inferior strap portions.

27. The patient interface according to claim 18, wherein when the strap receiving portion is connected to the strap attachment portion, the strap receiving portion has a width that is greater than a width of the strap attachment portion at least over a portion of the region where the strap receiving portion contacts the strap attachment portion.

28. The patient interface according to claim 18, wherein a corresponding one of the superior strap portions, a corresponding one of the inferior strap portions and a corresponding one of the posterior connecting strap portions together at least partially form an opening to receive the patient's ear without extending over the patient's ear during use.

29. The patient interface according to claim 18, wherein the posterior connecting strap portions are configured to, in use, engage portions of the patient's head posterior of the patient's ears.

30. The patient interface according to claim 18, wherein the pair of posterior connecting strap portions comprise a mesh material different than the material used to construct the superior strap portions and the inferior strap portions, wherein the positioning and stabilizing structure further comprises a back strap connected to or formed integrally with the pair of posterior connecting strap portions, the back strap having a stretch capability greater than a stretch capability of the superior strap portions, wherein the superior strap portions and the inferior strap portions are constructed at least partially from a textile material, wherein the positioning and stabilizing structure further comprises a crown strap portion connected to or formed integrally with the pair of posterior connecting strap portions, the crown strap portion having a stretch capability less than a stretch capability of the posterior connecting strap portions, wherein each superior strap portion has a posterior end portion and an anterior end portion, and each inferior strap portion has a posterior end portion and an anterior end portion, wherein each posterior connecting strap portion interconnects the posterior end portion of a respective one of the superior strap portions and the posterior end portion of a respective one of the inferior strap portions, and each anterior strap portion interconnects the anterior end portion of a respective one of the superior strap portions and the anterior end portion of a respective one of the inferior strap portions, wherein when the strap receiving portion is connected to the strap attachment portion, the strap receiving portion has a width that is greater than a width of the strap attachment portion at least over a portion of the region where the strap receiving portion contacts the strap attachment portion, wherein a corresponding one of the superior strap portions, a corresponding one of the inferior strap portions and a corresponding one of the posterior connecting strap portions together at least partially form an opening to receive the patient's ear without extending over the patient's ear during use, and wherein the posterior connecting strap portions are configured to, in use, engage portions of the patient's head posterior of the patient's ears.

* * * * *